(12) United States Patent
Harrington et al.

(10) Patent No.: US 10,518,061 B2
(45) Date of Patent: Dec. 31, 2019

(54) HUMIDIFIER FOR A RESPIRATORY THERAPY DEVICE

(71) Applicant: ResMed Pty Ltd, Bella Vista, New South Wales (AU)

(72) Inventors: Matthew Rolf Harrington, Gosford (AU); Dmitri Anatolievich Doudkine, Sydney (AU); Roger Mervyn Lloyd Foote, Sydney (AU); Ronald James Huby, Sydney (AU); Zhuo Ran Tang, Sydney (AU); Nan Hai Wu, Sydney (AU); Quangang Yang, Sydney (AU); Andrew Roderick Bath, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 517 days.

(21) Appl. No.: 15/125,761

(22) PCT Filed: Mar. 13, 2015

(86) PCT No.: PCT/AU2015/050102
§ 371 (c)(1),
(2) Date: Sep. 13, 2016

(87) PCT Pub. No.: WO2015/135040
PCT Pub. Date: Sep. 17, 2015

(65) Prior Publication Data
US 2017/0000968 A1    Jan. 5, 2017

(30) Foreign Application Priority Data

Mar. 13, 2014  (AU) .................................. 2014900869
Mar. 24, 2014  (AU) .................................. 2014901035
Nov. 11, 2014  (AU) .................................. 2014904513

(51) Int. Cl.
*A61M 16/16*    (2006.01)
*A61M 16/10*    (2006.01)
(Continued)

(52) U.S. Cl.
CPC .......... *A61M 16/16* (2013.01); *A61M 16/026* (2017.08); *A61M 16/06* (2013.01);
(Continued)

(58) Field of Classification Search
CPC ............ A61M 11/042; A61M 16/0003; A61M 16/0057; A61M 16/0066; A61M 16/06;
(Continued)

(56) References Cited

U.S. PATENT DOCUMENTS 4,086,305 A     4/1978  Dobritz
4,225,542 A *   9/1980  Wall .................. A61M 16/1075
                                                         128/203.12

(Continued)

FOREIGN PATENT DOCUMENTS

EP         0391814        10/1990
GB         600987         4/1948
(Continued)

OTHER PUBLICATIONS

Further Examination Report issued in related New Zealand Application No. 724538 dated Oct. 26, 2017, 5 pages.
(Continued)

*Primary Examiner* — Annette Dixon
(74) *Attorney, Agent, or Firm* — Nixon & Vanderhye P.C.

(57) ABSTRACT

A humidifier for humidification of air to be delivered to a patient's airways may include a humidification chamber, a reservoir and a water delivery mechanism. The humidification chamber may include a water retention feature such as a wick that encloses part of the flow path, a heating element for heating the humidification chamber, and an air flow baffle configured to promote humidification. The humidifier may be further configured to execute one or more algorithms, for example to determine a condition of the wick or to detect condensation in the flow path. In some forms, the
(Continued)

humidifier may also comprise algorithms for controlling one or more components of the humidifier such as to control the build up of foreign matter on the wick.

20 Claims, 31 Drawing Sheets

(51) Int. Cl.
  *A61M 16/06* (2006.01)
  *A61M 16/14* (2006.01)
  *A61M 16/00* (2006.01)
  *A61M 11/04* (2006.01)

(52) U.S. Cl.
  CPC ........ *A61M 16/109* (2014.02); *A61M 16/142* (2014.02); *A61M 11/044* (2014.02); *A61M 16/107* (2014.02); *A61M 16/1055* (2013.01); *A61M 16/161* (2014.02); *A61M 2205/3368* (2013.01); *A61M 2205/3379* (2013.01); *A61M 2205/3389* (2013.01); *A61M 2205/6018* (2013.01); *A61M 2205/70* (2013.01); *A61M 2205/707* (2013.01); *A61M 2206/14* (2013.01)

(58) Field of Classification Search
  CPC .......... A61M 16/0816; A61M 16/0825; A61M 16/0833; A61M 16/0875; A61M 16/1045; A61M 16/1075; A61M 16/108; A61M 16/1085; A61M 16/109; A61M 16/1095; A61M 16/142; A61M 16/147; A61M 16/16; A61M 16/161; A61M 16/162; A61M 16/164; A61M 16/167; A61M 16/168; A61M 16/202; A61M 2016/0027; A61M 2205/14; A61M 2205/3334; A61M 2205/3368; A61M 2205/3375; A61M 2205/3653; A61M 2205/6018; A61M 2205/6054; A61M 2205/7518; A61M 2205/7527; A61M 2205/8206; A61M 2209/10; A61M 2230/04; A62B 9/003; B01F 3/022; B01F 3/0407; F24F 11/56; F24F 2006/125; F24F 6/08; F24F 6/10; F24F 6/12; G05D 9/12; Y02B 30/80; Y10S 128/909; Y10S 261/15; Y10S 261/34; Y10S 261/46; Y10S 261/48; Y10S 261/65; Y10T 137/7358
  See application file for complete search history.

(56) References Cited

U.S. PATENT DOCUMENTS

| | | | |
|---|---|---|---|
| 4,303,601 A | 12/1981 | Grimm et al. | |
| 4,441,027 A | 4/1984 | Richardson et al. | |
| 4,489,015 A | 12/1984 | Petersen et al. | |
| 4,676,237 A | 6/1987 | Wood et al. | |
| 4,708,831 A * | 11/1987 | Elsworth | A61M 16/0051 261/130 |
| 4,753,887 A * | 6/1988 | Bellare | G01N 1/42 435/1.3 |
| 4,782,832 A | 11/1988 | Trimble et al. | |
| 4,944,310 A | 7/1990 | Sullivan | |
| 4,968,457 A | 11/1990 | Welch | |
| 5,148,801 A | 9/1992 | Douwens et al. | |
| 5,309,726 A | 5/1994 | Asbridge | |
| 5,336,156 A | 8/1994 | Miller et al. | |
| 5,349,946 A | 9/1994 | McComb | |
| 5,715,698 A | 2/1998 | Calton | |
| 5,775,580 A | 7/1998 | Sizemore | |
| 5,800,741 A | 9/1998 | Glenn et al. | |
| 5,916,493 A | 6/1999 | Miller | |
| 6,000,684 A | 12/1999 | Pasch et al. | |
| 6,095,505 A * | 8/2000 | Miller | A61M 16/1075 128/203.27 |
| 6,367,277 B1 | 4/2002 | Kinkel | |
| 6,510,848 B1 | 1/2003 | Gibertoni | |
| 6,532,959 B1 | 3/2003 | Berthon-Jones | |
| 6,581,594 B1 | 6/2003 | Drew et al. | |
| 6,581,917 B2 | 6/2003 | Mulvaney | |
| 6,796,550 B2 | 9/2004 | Mulvaney | |
| 6,824,126 B2 | 11/2004 | Keller et al. | |
| 6,895,803 B2 | 5/2005 | Seakins et al. | |
| 7,866,944 B2 | 1/2011 | Kenyon et al. | |
| 8,636,479 B2 | 1/2014 | Kenyon et al. | |
| 8,638,014 B2 | 1/2014 | Sears et al. | |
| 8,733,349 B2 | 5/2014 | Bath et al. | |
| 2002/0050656 A1 | 5/2002 | Offir et al. | |
| 2006/0012057 A1 | 1/2006 | Anthony | |
| 2007/0107879 A1 | 5/2007 | Radomski et al. | |
| 2009/0044808 A1 | 2/2009 | Guney et al. | |
| 2009/0050156 A1 | 2/2009 | Ng et al. | |
| 2009/0250055 A1 | 10/2009 | Radomski et al. | |
| 2009/0320840 A1 | 12/2009 | Klasek et al. | |
| 2010/0000534 A1 | 1/2010 | Kooij et al. | |
| 2010/0024816 A1 | 2/2010 | Weinstein et al. | |
| 2010/0313584 A1 | 12/2010 | Lopez et al. | |
| 2013/0081619 A1 | 4/2013 | Seakins et al. | |
| 2013/0133651 A1 | 5/2013 | Barker et al. | |
| 2013/0186611 A1 | 7/2013 | Schneider et al. | |
| 2013/0239966 A1 | 9/2013 | Klasek et al. | |
| 2018/0056024 A1 * | 3/2018 | Harrington | A61M 16/109 |

FOREIGN PATENT DOCUMENTS

| | | |
|---|---|---|
| GB | 1485458 | 9/1977 |
| JP | 2-193680 | 7/1990 |
| JP | 02-225925 | 9/1990 |
| JP | 9-234247 | 9/1997 |
| JP | 2000-5314 | 11/2000 |
| JP | 2012-197971 | 10/2012 |
| WO | WO 98/004310 A1 | 2/1998 |
| WO | WO 98/034665 A1 | 8/1998 |
| WO | WO 2000/078381 A1 | 12/2000 |
| WO | 03/099367 A2 | 12/2003 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | WO 2008/055308 A1 | 5/2008 |
| WO | WO 2009/015410 | 2/2009 |
| WO | WO 2009/052560 A1 | 4/2009 |
| WO | WO 2010/135785 A1 | 12/2010 |
| WO | 2012/077052 A1 | 6/2012 |
| WO | WO 2012/098303 A1 | 7/2012 |
| WO | WO 2012/171072 A1 | 12/2012 |
| WO | WO 2013/020167 A1 | 2/2013 |
| WO | WO 2013/124803 A1 | 8/2013 |
| WO | WO 2015/135040 | 9/2015 |

OTHER PUBLICATIONS

First Office Action issued in related Chinese Application No. 201580024833.4 dated May 3, 2018, with English translation, 17 pages.
Further Examination Report issued in corresponding New Zealand Application No. 724538 dated Jul. 27, 2017, 8 pages.
International Search Report for PCT/IB2016/051262, dated Jul. 4, 2016, 8 pages.
Written Opinion of the ISA for PCT/IB2016/051262, dated Jul. 4, 2016, 11 pages.
International Search Report for PCT/AU2015/050102, dated Jul. 3, 2015, 15 pages.
Written Opinion of the ISA for PCT/AU2015/050102, dated Jul. 3, 2015, 11 pages.
Written Opinion of the IPE for PCT/AU2015/050102, dated Feb. 1, 2016, 11 pages.
International Preliminary Report on Patentability for PCT/AU2015/050102, dated Jun. 23, 2015, 27 pages.

(56) References Cited

OTHER PUBLICATIONS

"*Respiratory Physiology*", by John B. West, Lippincott Williams & Wilkins, 9$^{th}$ edition published 2012 (8 pages).
First Examination Report issued in corresponding New Zealand Application No. 716700 dated Feb. 23, 2016, 3 pages.
First Examination Report issued in corresponding New Zealand Application No. 7324099 dated Aug. 28, 2017, 2 pages.
First Office Action issued in related Japanese Application No. 2016-557038 dated Nov. 26, 2018, with English translation, (9 pages).
Second Office Action issued in related Chinese Application No. 201580024833.4 dated Jan. 30, 2019, with English translation, (5 pages).
First Examination Report issued in corresponding New Zealand Application No. 724538 dated Jan. 11, 2017, 5 pages.
Supplementary European Search Report issued in related European Application No. 15 76 0706.0 dated Nov. 22, 2017, 8 pages.
First Examination Report issued in corresponding New Zealand Application No. 630745 dated Sep. 22, 2014, 3 pages.

* cited by examiner

HUMIDIFIER FOR A RESPIRATORY THERAPY DEVICE

This application is the U.S. national phase of international Application No. PCT/AU2015/050102 filed 13 Mar. 2015, which designated the U.S. and claims priority to Australian Provisional Patent Application Nos. AU 2014900869, filed Mar. 13, 2014, AU 2014901035, filed Mar. 24, 2014, and AU 2014904513, filed Nov. 11, 2014, the entire contents of each of which are incorporated herein by reference.

1 CROSS-REFERENCE TO RELATED APPLICATIONS

This application claims the benefit of Australian Provisional Patent Application Nos. AU 2014900869, filed Mar. 13, 2014, AU 2014901035, filed Mar. 24, 2014, and AU 2014904513, filed Nov. 11, 2014, each of which is incorporated herein by reference in its entirety.

2 BACKGROUND OF THE TECHNOLOGY 2.1 Field of the Technology

The present technology relates to one or more of the detection, diagnosis, treatment, prevention and amelioration of respiratory-related disorders. In particular, the present technology relates to medical devices or apparatus, and their use.

2.2 Description of the Related Art
2.2.1 Human Respiratory System

The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2011.

A range of respiratory disorders exist.

Obstructive Sleep Apnea (OSA), a form of Sleep Disordered Breathing (SDB), is characterized by occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnea on exertion, peripheral oedema, orthopnea, repeated chest infections, morning headaches, fatigue, poor sleep quality and loss of appetite.

Otherwise healthy individuals may take advantage of systems and devices to prevent respiratory disorders from arising.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) provides ventilatory support to a patient through the upper airways to assist the patient in taking a full breath and/or maintain adequate oxygen levels in the body by doing some or all of the work of breathing. The ventilatory support is provided via a patient interface. NIV has been used to treat CSR, OHS, COPD, MD and Chest Wall disorders.

Invasive ventilation (IV) provides ventilatory support to patients that are no longer able to effectively breathe themselves and is provided using a tracheostomy tube.

Ventilators may control the timing and pressure of breaths pumped into the patient and monitor the breaths taken by the patient. The methods of control and monitoring patients typically include volume-cycled and pressure-cycled methods. The volume-cycled methods may include among others, Pressure-Regulated Volume Control (PRVC), Volume Ventilation (VV), and Volume Controlled Continuous Mandatory Ventilation (VC-CMV) techniques. The pressure-cycled methods may involve, among others, Assist Control (AC), Synchronized Intermittent Mandatory Ventilation (SIMV), Controlled Mechanical Ventilation (CMV), Pressure Support Ventilation (PSV), Continuous Positive Airway Pressure (CPAP), or Positive End Expiratory Pressure (PEEP) techniques.

2.2.3 Systems

A system may comprise a Respiratory Therapy Device (RPT) device, an air circuit, a humidifier, a patient interface, and data management.

2.2.4 Patient Interface

A patient interface may be used to interface respiratory equipment to its user, for example by providing a flow of air. The flow of air may be provided via a mask to the nose and/or mouth, a tube to the mouth or a tracheostomy tube to the trachea of the user. Depending upon the therapy to be applied, the patient interface may form a seal, e.g. with a face region of the patient, to facilitate the delivery of gas at a pressure at sufficient variance with ambient pressure to effect therapy, e.g. a positive pressure of about 10 cmH2O. For other forms of therapy, such as the delivery of oxygen, the patient interface may not include a seal sufficient to facilitate delivery to the airways of a supply of gas at a positive pressure of about 10 cmH2O.

The design of a patient interface presents a number of challenges. The face has a complex three-dimensional shape. The size and shape of noses varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. For example, masks designed solely for aviators, mask designed as part of personal protection equipment (e.g. filter masks), SCUBA masks, or for the administration of anaesthetics may be tolerable for their original application, but nevertheless be undesirably uncomfortable to be worn for extended periods of time, e.g. several hours. This is even more so if the mask is to be worn during sleep.

Nasal CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g. difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, masks for delivery of nasal CPAP during sleep form a distinct field.

2.2.5 Respiratory Pressure Therapy (RPT) Device

Examples of RPT devices include ResMed's S9 AutoSet™ PAP device and ResMed's Stellar™ 150 ventilator. RPT devices may comprise a pressure generator, such as a motor-driven blower or a compressed gas reservoir, and may be configured to supply a flow of air to the airway of a patient. In some cases, the flow of air may be supplied to the airway of the patient at positive pressure. The outlet of the RPT device is connected via an air circuit to a patient interface such as those described above. In some cases, RPT devices have been known to be referred to as flow generators.

RPT devices may include a pressure generator, an inlet filter, various sensors and a microprocessor-based controller. The pressure generator may include a servo-controlled motor, volute and an impeller. In some cases a brake for the motor may be implemented to more rapidly reduce the speed of the blower so as to overcome the inertia of the motor and impeller. The braking can permit the blower to more rapidly achieve a lower pressure condition in time for synchronization with exhalation despite the inertia. In some cases the pressure generator may also include a valve capable of discharging generated air to atmosphere as a means for altering the pressure delivered to the patient as an alternative to motor speed control. The sensors may measure, amongst other things, motor speed, air flow rate and outlet pressure, such as with a pressure transducer or the like. The controller may include data storage capacity with or without integrated data retrieval and display functions.

Table of noise output levels of prior devices (one specimen only, measured using test method specified in ISO3744 in CPAP mode at 10 cmH$_2$O).

| Device name | A-weighted sound power level dB(A) | Year (approx.) |
| --- | --- | --- |
| C-Series Tango | 31.9 | 2007 |
| C-Series Tango with Humidifier | 33.1 | 2007 |
| S8 Escape II | 30.5 | 2005 |
| S8 Escape II with H4i Humidifier | 31.1 | 2005 |
| S9 AutoSet | 26.5 | 2010 |
| S9 AutoSet with H5i Humidifier | 28.6 | 2010 |

2.2.6 Humidifier

Delivery of a flow of air without humidification may cause drying of airways. Medical humidifiers, or humidifiers for respiratory therapy devices, may be used to increase absolute humidity and/or temperature of the flow of air in relation to ambient air when required, for example, where the patient may be asleep or resting (e.g. at a hospital). As a result, a medical humidifier may be small for bedside placement, and it may be configured to only humidify and/or heat the flow of air delivered to the patient without humidifying and/or heating the patient's surroundings. Room-based systems (e.g. a sauna, an air conditioner, an evaporative cooler), for example, may also humidify air that is breathed in by the patient, however they would also humidify and/or heat the entire room, which may cause discomfort to the occupants.

The use of a humidifier with a pressure generator or RPT device and the patient interface produces humidified gas that minimizes drying of the nasal mucosa and increases patient airway comfort. In addition in cooler climates, warm air applied generally to the face area in and about the patient interface is more comfortable than cold air.

Respiratory humidifiers are available in many forms and may be a standalone device that is coupled to an RPT device via an air conduit, may be integrated with the RPT device, or may be configured to be directly coupled to the relevant RPT device. While known passive humidifiers can provide some relief, generally a heated humidifier may be used to provide sufficient humidity and temperature to the air so that the patient will be comfortable. Humidifiers may comprise a water reservoir or tub having a capacity of several hundred milliliters (ml), a heating element for heating the water in the reservoir, a control to enable the level of humidification to be varied, a gas inlet to receive gas from the RPT device, and a gas outlet adapted to be connected to an air circuit that delivers the humidified gas to the patient interface.

Heated passover humidification is one exemplary form of humidification used with an RPT device. In such humidifiers the heating element may be incorporated in a heater plate which sits under, and is in thermal contact with, the water tub. Thus, heat is transferred from the heater plate to the water reservoir primarily by conduction. The air flow from the RPT device passes over the heated water in the water tub resulting in water vapour being taken up by the air flow. The ResMed H4i™ and H5i™ Humidifiers are examples of such heated passover humidifiers that are used in combination with ResMed S8 and S9 RPT devices respectively.

Other humidifiers may also be used such as a bubble or diffuser humidifier or a jet humidifier. In a bubble or diffuser humidifier the air is conducted below the surface of the water and allowed to bubble back to the top. A jet humidifier produces an aerosol of water and baffles or filters may be used so that the particles are either removed or evaporated before leaving the humidifier.

An alternative form of humidification is provided by the ResMed HumiCare™ D900 humidifier that uses a Counter-Stream™ technology that directs the air flow over a large surface area in a first direction whilst supplying heated water to the large surface area in a second opposite direction. The ResMed HumiCare™ D900 humidifier may be used with a range of invasive and non-invasive ventilators.

One example of a prior art humidifier 5000 is shown in FIGS. 6A and 6B, and comprises a reservoir 5110 to retain a volume of liquid (e.g. water), a humidifier inlet 5002 to receive a flow of air, and a humidifier outlet 5004 to deliver a humidified flow of air. In some forms, as shown in FIG. 6A and FIG. 6B, an inlet and an outlet of the reservoir 5110 may be the humidifier inlet 5002 and the humidifier outlet 5004 respectively. The reservoir 5110 may be a removable component of the humidifier 5000. The humidifier 5000 may further comprise a humidifier dock 5130, which may be adapted to receive the reservoir 5110 and comprise a heating element 5220. The reservoir 5110 may comprise a conductive plate 5120 configured to allow efficient transfer of heat from the heating element 5220 to the volume of liquid in the reservoir 5110.

Thus, in such a form, the reservoir 5110 contains the entire volume of water to be used to humidify the flow of air, and receives the flow of air to pass over the water and delivers the humidified flow of air. Accordingly, such a humidifier configuration presents a number of challenges, including: risk of spillage of the volume of water (e.g. into the RPT device or to the patient), achieving adequate humidification output, high thermal mass of the volume of water and changes to thermal mass according to changes in water volume present in the reservoir 5110. Due to these challenges, many prior art humidifiers may suffer from one or more of: long warm-up time and cool-down time, slow response time (e.g. to a change in desired humidification output), change to response time throughout a therapy session and large size. The large size may manifest itself in terms of volume and/or footprint (i.e. surface area covered by the humidifier, or effectively covered by the humidifier as to become inaccessible), which may make the humidifier less suited for placement on a bedside table for example. A humidifier 5000 according to the present technology seeks to improve upon, or ameliorate, one or more of the above characteristics.

3 BRIEF SUMMARY OF THE TECHNOLOGY

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to an apparatus used in the diagnosis, amelioration, treatment or prevention of a respiratory disorder.

Another aspect of the present technology relates to methods used in the diagnosis, amelioration, treatment or prevention of a respiratory disorder.

One aspect of the present technology relates to a humidifier for increasing an absolute humidity of a flow of air to be delivered to a patient's airways by a respiratory therapy device. The humidifier may comprise a reservoir configured to retain a first volume of water, a humidifier chamber comprising an air inlet configured to receive the flow of air from a pressure device, an air outlet configured to deliver the flow of air to a patient interface from the humidifier chamber with added humidity, a flow path for the flow of air through the humidifier chamber, a humidifier wick configured to retain a second volume of water and the humidifier wick having a profiled shape to substantially enclose at least a portion of the flow path for the flow of air in an axial direction of the flow path, a heating element, and an air flow baffle configured to lengthen the flow path for the flow of air through the humidifier chamber, and a delivery mechanism configured to deliver a flow of water from the reservoir to the humidifier wick, wherein the heating element is configured to heat the humidifier wick to vaporise the second volume of water to add absolute humidity to the flow of air and the humidifier wick is removable from the humidifier chamber.

According to another aspect of the present technology, the humidifier wick may be anisotropically configured.

According to another aspect of the present technology, the humidifier wick may be further configured so that a rate of wicking is greater in a first direction than in a second direction.

According to another aspect of the present technology, the second direction may be a direction of the flow of air.

According to another aspect of the present technology, the path enclosed by the humidifier wick may be substantially cylindrical.

According to another aspect of the present technology, the humidifier wick may comprise one or more of: a corrugated, a dimpled, a perforated, a porous, a woven, a knitted, a textured, and a sintered surface.

According to another aspect of the present technology, the humidifier wick may comprise one or more of: paper, hydrophilic fibres, and cellulose fibres.

According to another aspect of the present technology, the humidifier wick may comprise a substrate for the heating element.

According to another aspect of the present technology, the humidifier wick may be configured to retain between 2-30 g of water.

According to another aspect of the present technology, the humidifier wick may comprise a heated region and an unheated region.

According to another aspect of the present technology, the unheated region may comprise an upstream unheated region located upstream of the heated region.

According to another aspect of the present technology, the upstream unheated region may comprise a faster wicking rate than the heated region.

According to another aspect of the present technology, a length of the upstream unheated region may be between approximately 5%-approximately 20% of the heated region.

According to another aspect of the present technology, the unheated region may comprise a downstream unheated region located downstream of the heated region.

According to another aspect of the present technology, a length of the downstream unheated region may be between approximately 20%-approximately 40% of the heated region.

According to another aspect of the present technology, the humidifier wick may be coupled to a frame.

According to another aspect of the present technology, the frame may be configured to be removably coupled to the humidifier chamber.

According to another aspect of the present technology, the frame may be configured to be removed from an exterior of the humidifier.

According to another aspect of the present technology, the frame may comprise a grip surface.

According to another aspect of the present technology, the frame may be configured to promote thermal contact between the humidifier wick and the heating element.

According to another aspect of the present technology, the frame may further comprise the air flow baffle.

According to another aspect of the present technology, the lengthened path may be helical.

According to another aspect of the present technology, the heating element may comprise a resistive electrical track.

According to another aspect of the present technology, the resistive electrical track may be disposed on a circuit board.

According to another aspect of the present technology, the circuit board may be a flexible circuit board.

According to another aspect of the present technology, the resistive electrical track may comprise one or more strands of resistive wire.

According to another aspect of the present technology, the one or more strands of resistive wire may form a plurality of loops around a surface of the humidifier chamber.

According to another aspect of the present technology, the heating element may further comprise an adhesive for securing the plurality of loops.

According to another aspect of the present technology, the delivery mechanism may be configured to deliver the flow of water to the humidifier wick through a plurality of fluid connections.

According to another aspect of the present technology, the delivery mechanism may be fluidly connected to the humidifier wick via a pre-delivery chamber.

According to another aspect of the present technology, at least one of the fluid connections may be a valve.

According to another aspect of the present technology, the delivery mechanism may comprise a pump.

According to another aspect of the present technology, the humidifier may further comprise one or more temperature sensors configured to measure one or more temperatures at the humidifier wick.

According to another aspect of the present technology, a plurality of temperature sensors may be located along a direction of the flow of air.

Another aspect of the present technology may further comprise a sensor configured to indicate a saturation condition of the humidifier wick.

According to another aspect of the present technology, a temperature sensor may be located at a periphery of the humidifier wick furthest from a water feed inlet to indicate the saturation condition.

Another aspect of the present technology may further comprise a controller configured to stop or slow delivery by the delivery mechanism upon indication of the saturation condition.

One aspect of the present technology relates to a humidifier chamber for a humidifier for increasing an absolute humidity of a flow of air to be delivered to a patient's airways by a respiratory therapy device. The humidifier chamber may comprise an air inlet configured to receive the flow of air from a pressure device, an air outlet configured to deliver the flow of air to a patient interface from the humidifier chamber with added humidity, a flow path through the humidifier chamber for the flow of air, and, a humidifier wick configured to retain a volume of water and the humidifier wick having a profiled shape to substantially enclose at least a portion of the flow path for the flow of air in an axial direction of the flow path.

According to another aspect of the present technology, the humidifier wick may be anisotropically configured.

According to another aspect of the present technology, the humidifier wick may be further configured so that a rate of wicking is greater in a first direction than in a second direction.

According to another aspect of the present technology, the second direction may be a direction of the flow of air.

According to another aspect of the present technology, the path enclosed by the humidifier wick may be substantially cylindrical.

According to another aspect of the present technology, the humidifier wick may comprise one or more of: a corrugated, a dimpled, a perforated, a porous, a woven, a knitted, a textured, and a sintered surface.

According to another aspect of the present technology, the humidifier wick may comprise one or more of: paper, hydrophilic fibres, and cellulose fibres.

According to another aspect of the present technology, the humidifier chamber may comprise a heating element.

According to another aspect of the present technology, the humidifier wick may comprise a substrate for the heating element.

According to another aspect of the present technology, the humidifier wick may be configured to retain between 2-30 g of water.

According to another aspect of the present technology, the humidifier wick may comprise a heated region and an unheated region.

According to another aspect of the present technology, the unheated region may comprise an upstream unheated region located upstream of the heated region.

According to another aspect of the present technology, the upstream unheated region may comprise a faster wicking rate than the heated region.

According to another aspect of the present technology, a length of the upstream unheated region may be between approximately 5%-approximately 20% of the heated region.

According to another aspect of the present technology, the unheated region may comprise a downstream unheated region located downstream of the heated region.

According to another aspect of the present technology, a length of the downstream unheated region may be between approximately 20%-approximately 40% of the heated region.

According to another aspect of the present technology, the humidifier wick may be coupled to a frame.

According to another aspect of the present technology, the frame may be configured to be removably coupled to the humidifier chamber.

According to another aspect of the present technology, the frame may be configured to be removed from an exterior of the humidifier.

According to another aspect of the present technology, the frame may comprise a grip surface.

According to another aspect of the present technology, the frame may be configured to promote thermal contact between the humidifier wick and the heating element.

According to another aspect of the present technology, the frame may further comprise an air flow baffle to lengthen the flow path.

According to another aspect of the present technology, the lengthened path may be helical.

According to another aspect of the present technology, the heating element may comprise a resistive electrical track.

According to another aspect of the present technology, the resistive electrical track may be disposed on a circuit board.

According to another aspect of the present technology, the circuit board may be a flexible circuit board.

According to another aspect of the present technology, the resistive electrical track may comprise one or more strands of resistive wire According to another aspect of the present technology, the one or more strands of resistive wire may form a plurality of loops around a surface of the humidifier chamber.

According to another aspect of the present technology, the heating element may further comprise an adhesive for securing the plurality of loops.

Another aspect of the present technology may further comprise one or more temperature sensors configured to measure one or more temperatures at the humidifier wick.

According to another aspect of the present technology, a plurality of temperature sensors may be located along the flow path of the flow of air.

Another aspect of the present technology may further comprise a sensor configured to indicate a saturation condition of the humidifier wick.

According to another aspect of the present technology, a temperature sensor may be located at a periphery of the humidifier wick furthest from a water feed inlet to indicate the saturation condition.

One aspect of the present technology relates to a method of determining suitability of a humidifier wick of a humidifier, e.g., a medical humidifier. The humidifier may comprise the humidifier wick and a controller configured to receive one more signals and/or generate one or more signals, and the humidifier wick may be configured to retain a volume of water. The method may comprise determining a set of input values with a controller, wherein the set of input values are indicative of a condition of a humidifier wick and the set of input values are provided to the controller by at least one of user input, at least one sensor, and a memory device, determining, based on the set of input values and a set of reference values, a condition set of the humidifier wick with the controller, and generating a signal with the controller based on the determined condition set to indicate a suitability of the humidifier wick for use in the humidifier.

According to another aspect of the present technology, the set of input values may comprise one or more of: wick type data, wick usage data, and measured wick condition data.

According to another aspect of the present technology, when the set of input values comprises the wick type data, the wick type data may comprise one or more of: wick model, date of manufacture, wick material, wick construction, wick dimensions, and initial water capacity.

According to another aspect of the present technology, when the set of input values comprises the wick usage data, the wick usage data may comprise one or more of: date of last replacement, time of use, quantity of water evaporated using the humidifier wick, and number of times that the humidifier wick has been washed.

According to another aspect of the present technology, when the set of input values comprises the measured wick condition data, the measured wick condition data may comprise one or more of: a measured temperature, a water capacity, and a water content.

According to another aspect of the present technology, the condition set may comprise one or more of: a water capacity, a water content, and a remaining useful life.

According to another aspect of the present technology, the set of reference values may comprise a temperature.

According to another aspect of the present technology, the set of reference values may comprise a temperature gradient.

According to another aspect of the present technology, the set of reference values may comprise a look-up table.

According to another aspect of the present technology, the method may further comprise communicating to a user the suitability of the humidifier wick with a visual and/or audible communication device in response to the signal generated by the controller.

One aspect of the present technology relates to a method of determining a water content of a humidifier wick of a humidifier, e.g., a medical humidifier. The humidifier may comprise the humidifier wick and a controller configured to receive one more signals and/or generate one or more signals, and the humidifier wick may be configured to retain a volume of water. The method may comprise providing a first temperature sensor in thermal contact with a first region of the humidifier wick and a second temperature sensor in thermal contact with a second region of the humidifier wick, applying a heat input to the humidifier wick, e.g., with a heating element, measuring a measured temperature set with the first temperature sensor and the second temperature sensor, determining a predicted temperature set at the first temperature sensor and the second temperature sensor, e.g., with a controller, and determining a water content of the humidifier wick based on a comparison of the measured temperature set received from the first temperature sensor and the second temperature sensor and the predicted temperature set.

According to another aspect of the present technology, the predicted temperature set may be determined based on one or more of a water flow rate to the humidifier wick and a rate of the heat input.

According to another aspect of the present technology, the first temperature sensor may be located at or near a periphery of the humidifier wick.

According to another aspect of the present technology, the first temperature sensor may be located at a periphery of the humidifier wick furthest from a water feed inlet to the humidifier wick.

According to another aspect of the present technology, the comparison may determine whether a temperature of the measured temperature set is outside of a threshold range of a corresponding temperature of the predicted temperature set.

One aspect of the present technology relates to a method of detecting occurrence of condensation in a flow path for a flow of air delivered by a humidifier, e.g., a medical humidifier. The method may comprise determining a first measure of a first property of the flow of air with a first sensor located in the flow path, determining a reference value of the first property of the flow of air with a second sensor located in the flow path, comparing the first measure with the reference value with a controller in communication with the first sensor and the second sensor, determining whether condensation has occurred in the flow path based on the comparison with the controller, and generating a signal with the controller indicating whether condensation has occurred in the flow path.

According to another aspect of the present technology, an occurrence of condensation may be determined with the controller upon a decrease in the first property from the reference value to the first measure.

According to another aspect of the present technology, the decrease in the first property from the reference value to the first measure may be above a predetermined threshold.

According to another aspect of the present technology, the reference value may be a second measure of the first property.

According to another aspect of the present technology, the second measure may be determined upstream of the first measure.

According to another aspect of the present technology, the reference value may be a prediction of the first property of the flow of air.

According to another aspect of the present technology, the prediction may be determined based on a steady-state condition.

According to another aspect of the present technology, the prediction may be determined based on one or more of: a pressure of the flow of air, a flow rate of the flow of air, an ambient temperature, an ambient humidity, an ambient pressure, a rate of heat transfer to the flow of air, and a rate of heat transfer between the flow of air and the ambient.

According to another aspect of the present technology, the first property of the flow of air is humidity, temperature, or rate of change of the temperature.

According to another aspect of the present technology, the prediction may be determined based on a steady-state condition.

One aspect of the present technology is directed to a method for controlling a location and/or a rate of foreign matter build-up on a humidifier wick of a humidifier. The humidifier may comprising the humidifier wick, a heating element to apply heat to the humidifier wick, a water delivery mechanism to deliver water to the humidifier wick, and a controller configured to receive one more signals and/or generate one or more signals, and the humidifier wick being configured to retain a volume of water. The method may comprise controlling a location and/or a pattern of a water boundary on the humidifier wick of the humidifier by varying, with the controller, at least one of: a heat output from the heating element onto the humidifier wick; a water flow rate from the water delivery mechanism onto the humidifier wick; and a water distribution pattern within the humidifier wick by adjusting the heat output from the heating element and/or the water flow rate from the water delivery, wherein controlling the location and/or the pattern of the water boundary causes foreign matter to build up at a predetermined region of the humidifier wick based on the location and/or the pattern of the water boundary.

According to another aspect of the present technology, the method may further comprise detecting a foreign matter content of the water with a sensor; and determining a quality of the water with the controller based on the foreign matter content detected by the sensor.

According to another aspect of the present technology, detecting the foreign matter content of the water with the sensor may further comprise measuring a conductivity of the water with the sensor.

According to another aspect of the present technology, detecting the foreign matter content of the water with the sensor may further comprise measuring resistivity of the water with electrodes in contact with the water.

According to another aspect of the present technology, the electrodes may be located in the humidifier wick and the water contained in the humidifier wick, and the resistivity measured by the electrodes may be directly correlated to a level of foreign matter build-up in the humidifier wick.

According to another aspect of the present technology, if the water flow rate from the water delivery mechanism is varied, then the water flow rate may be varied between a minimum water flow and a maximum water flow rate.

According to another aspect of the present technology, the water flow rate may be varied linearly or sinusoidally.

According to another aspect of the present technology, if the location of the water boundary is controlled, then the location of the water boundary may be varied in a reciprocating motion such that the water boundary moves between at least a first location and a second location.

According to another aspect of the present technology, if the heat output from the heating element onto the humidifier wick is varied, then the heat output may be varied between a minimum heat output and a maximum heat output.

According to another aspect of the present technology, the heat output may be varied linearly or sinusoidally.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

4.2 Therapy 4.2.1 Respiratory System

Figure 1A:
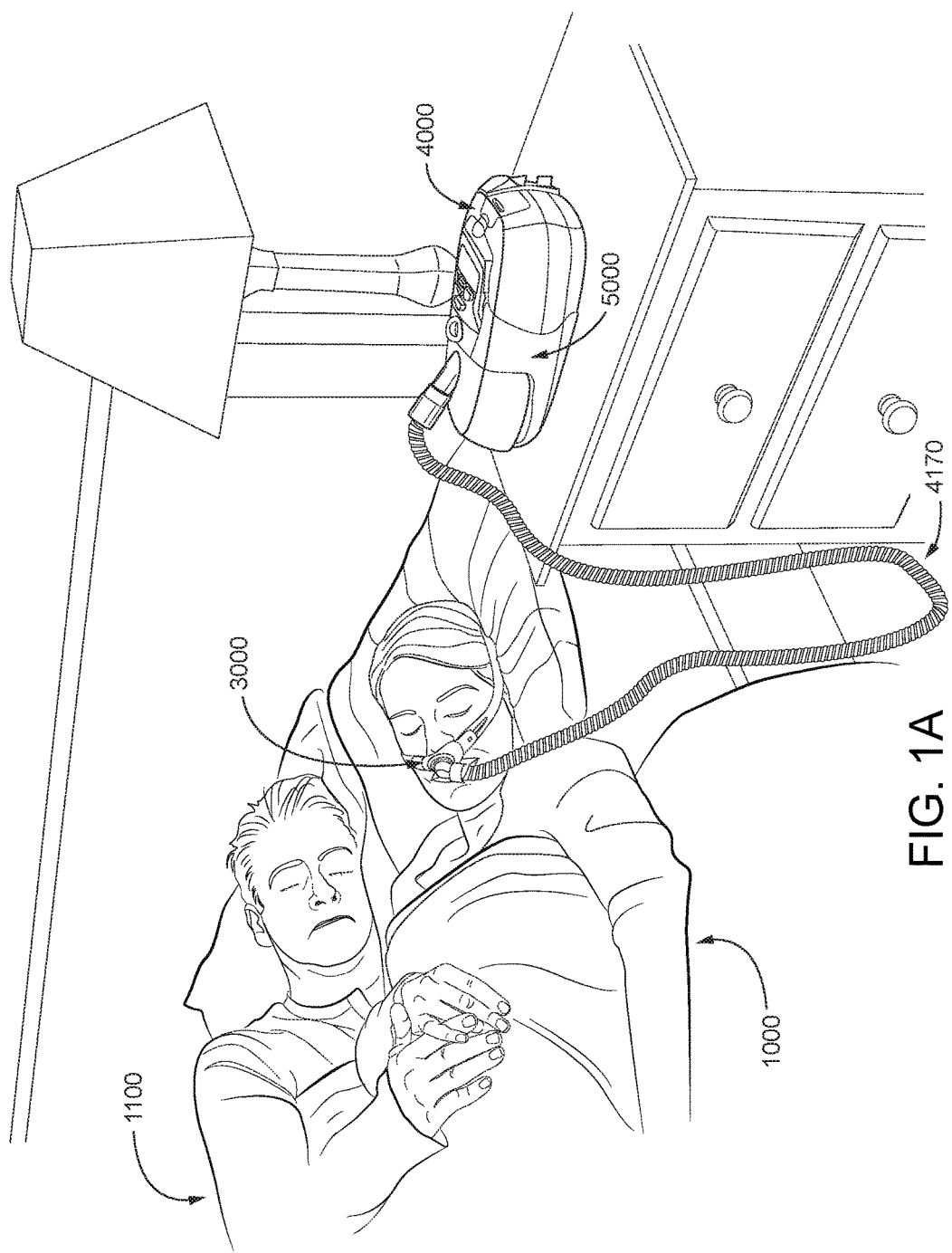
FIG. 1A shows a system including a patient 1000 wearing a patient interface 3000, in the form of a nasal pillows, receiving a supply of air at positive pressure from an RPT device 4000. Air from the RPT device is humidified in a humidifier 5000, and passes along an air circuit 4170 to the patient 1000, a bed partner 1100 is also shown.
Figure 1B:
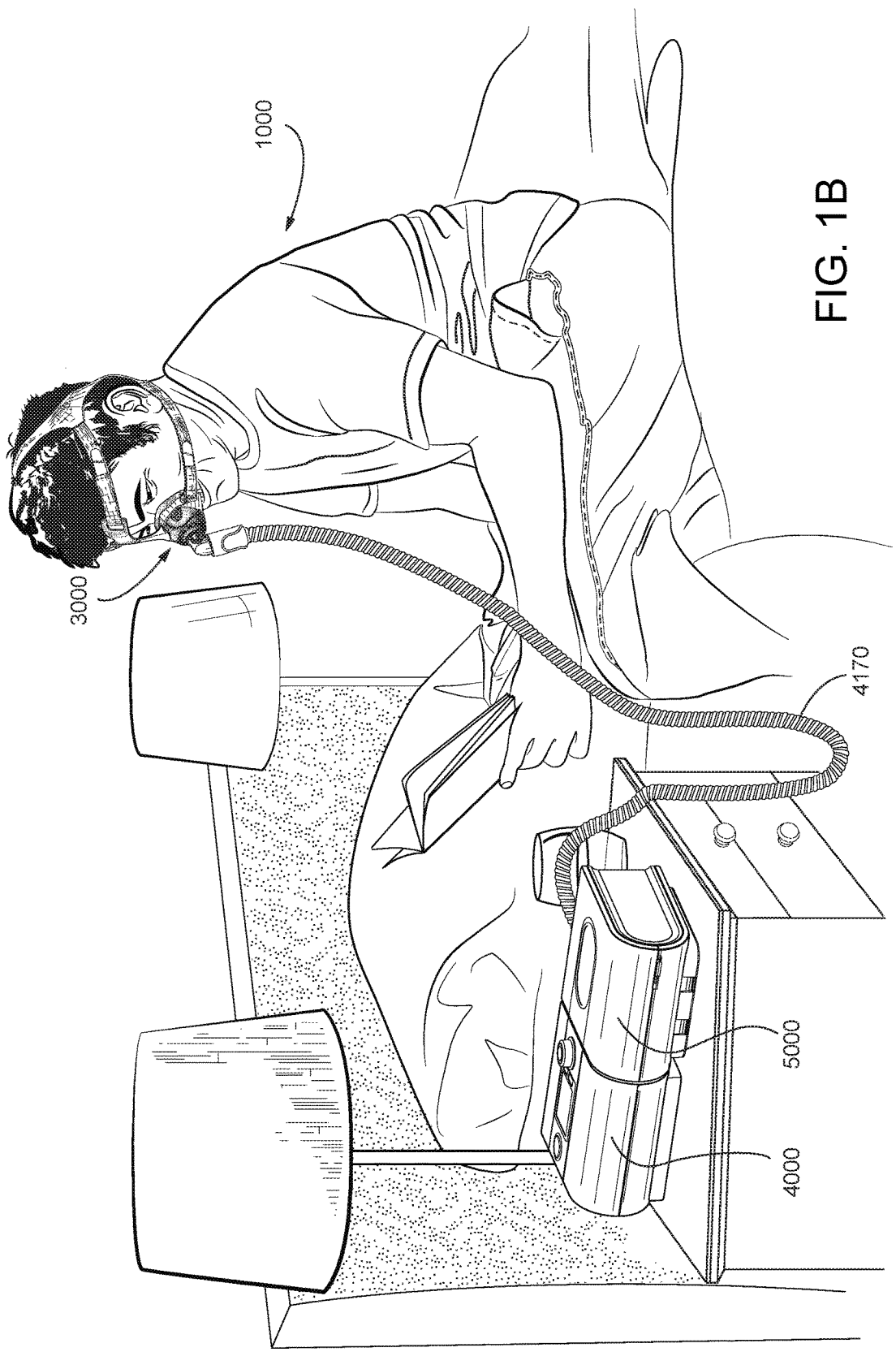
FIG. 1B shows a system including a patient 1000 wearing a patient interface 3000, in the form of a nasal mask, receiving a supply of air at positive pressure from an RPT device 4000. Air from the RPT device is humidified in a humidifier 5000, and passes along an air circuit 4170 to the patient 1000.
Figure 1C:
FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000.
Figure 2A:
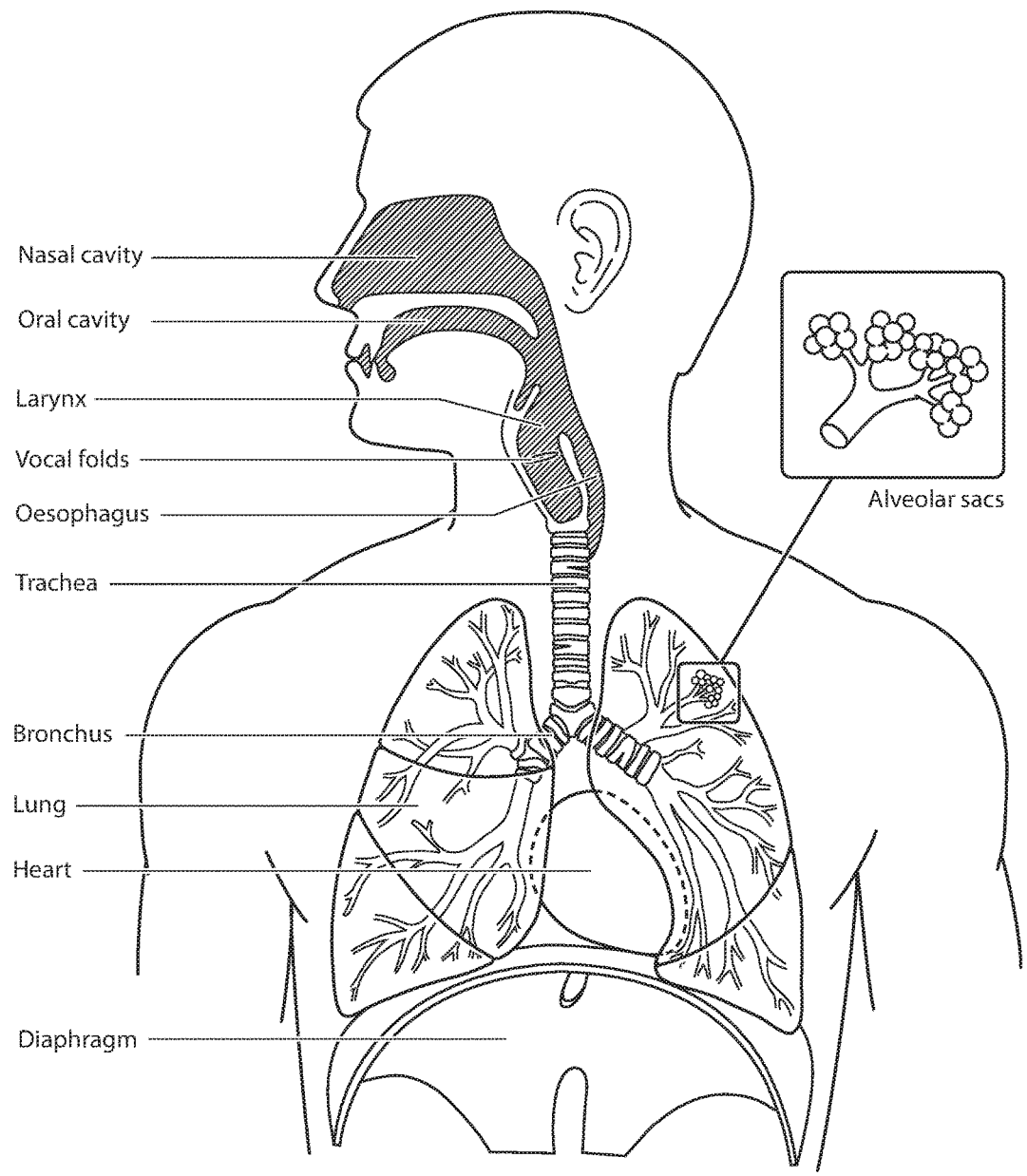

FIG. 2A shows an overview of a human respiratory system including the nasal and oral cavities, the larynx, vocal folds, oesophagus, trachea, bronchus, lung, alveolar sacs, heart, and diaphragm.

Figure 2B:
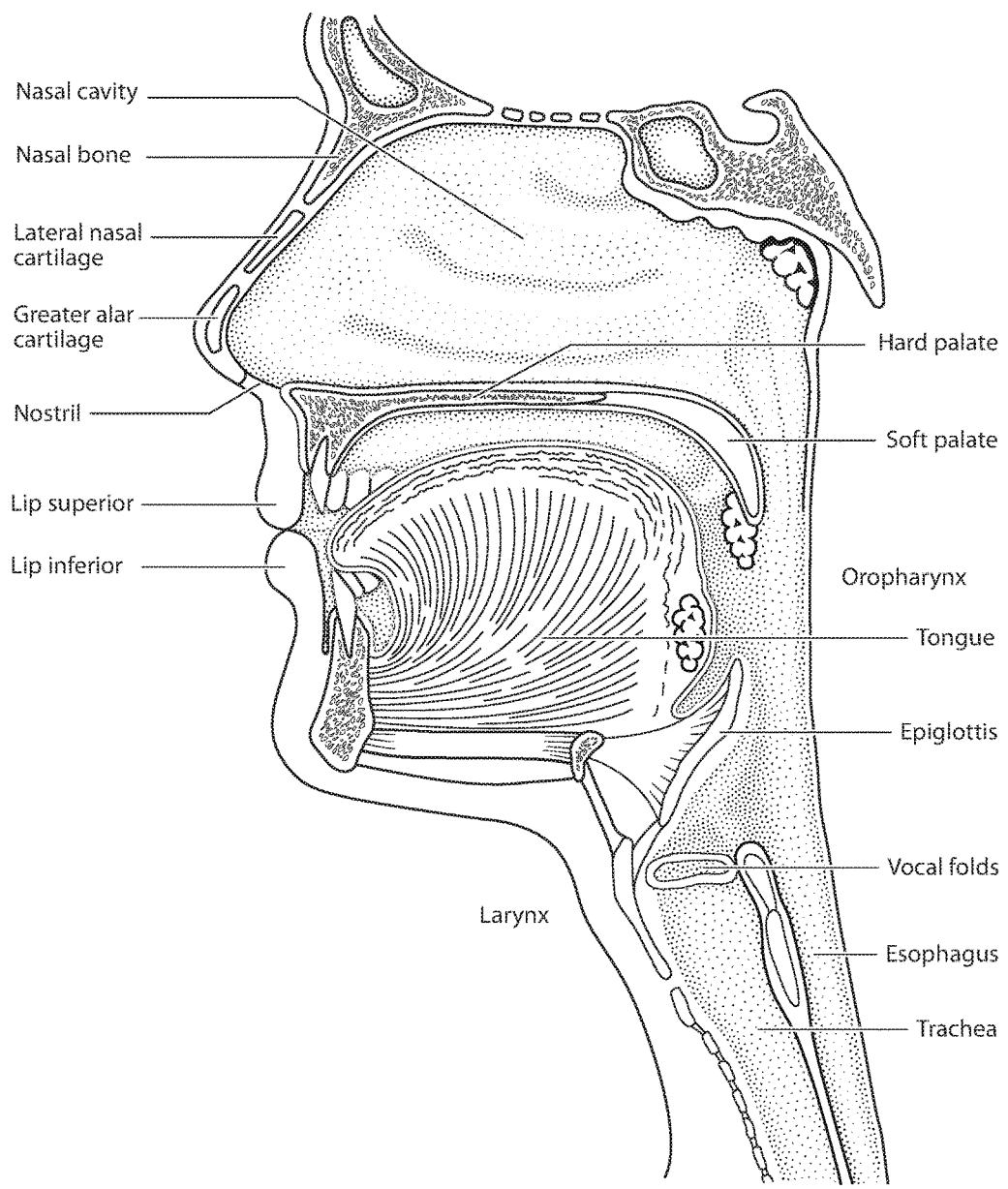

FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus, and trachea.

4.3 Patient Interface

Figure 3:
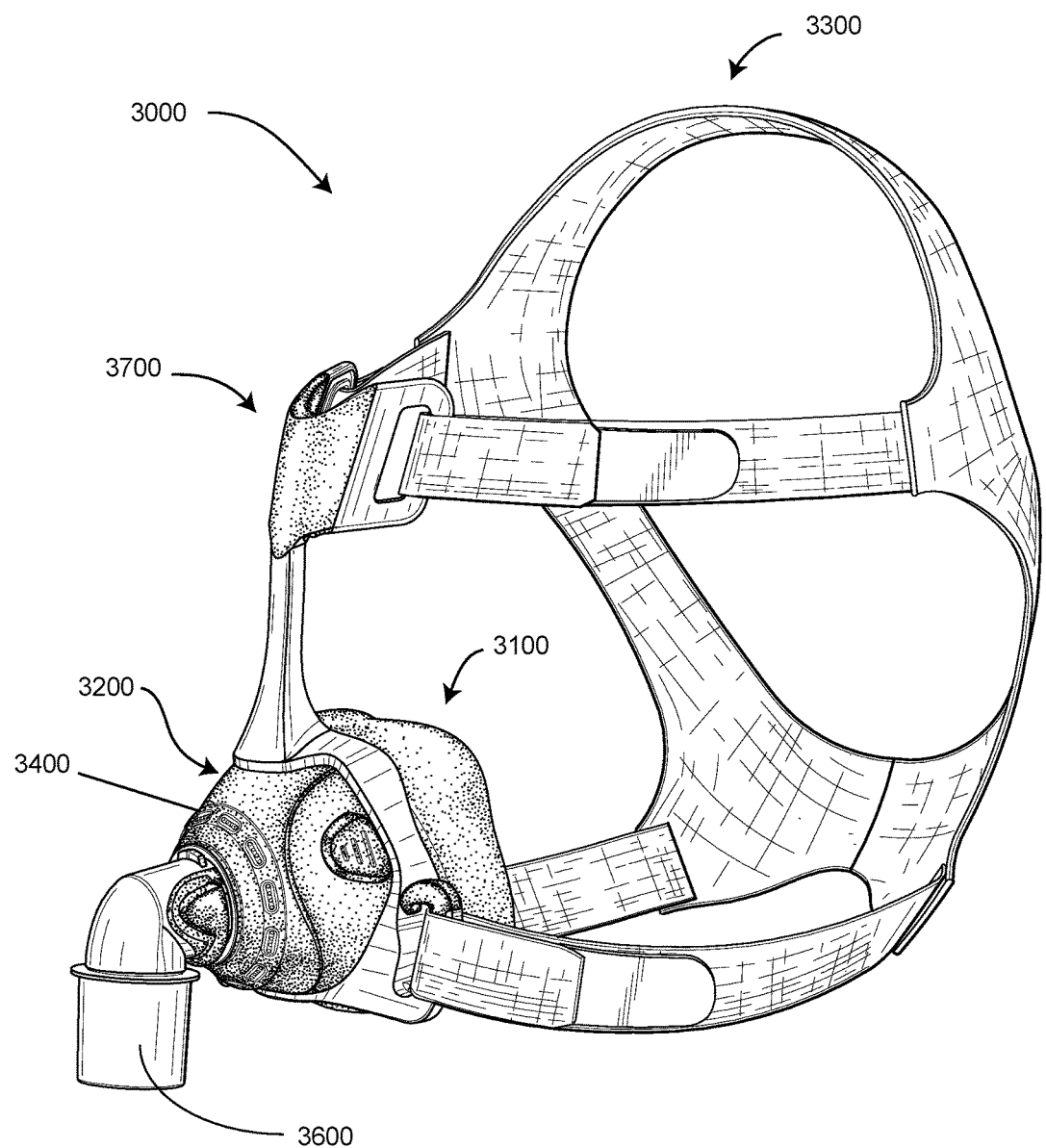

FIG. 3 shows a patient interface 3000 in the form of a nasal mask in accordance with one form of the present technology.

4.4 RPT Device

Figure 4A:
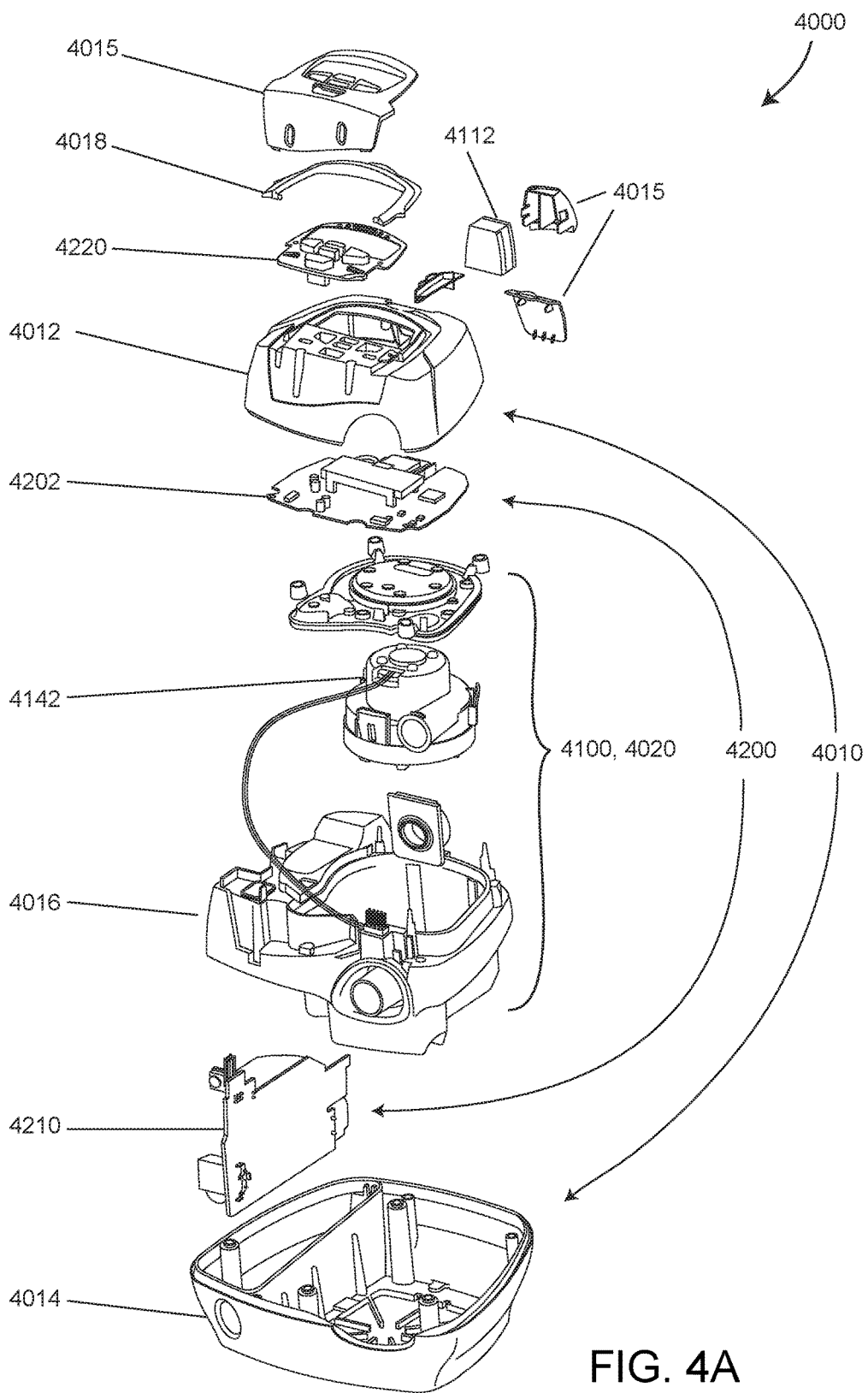

FIG. 4A shows an exploded view of an RPT device 4000 in accordance with one form of the present technology.

Figure 4B:
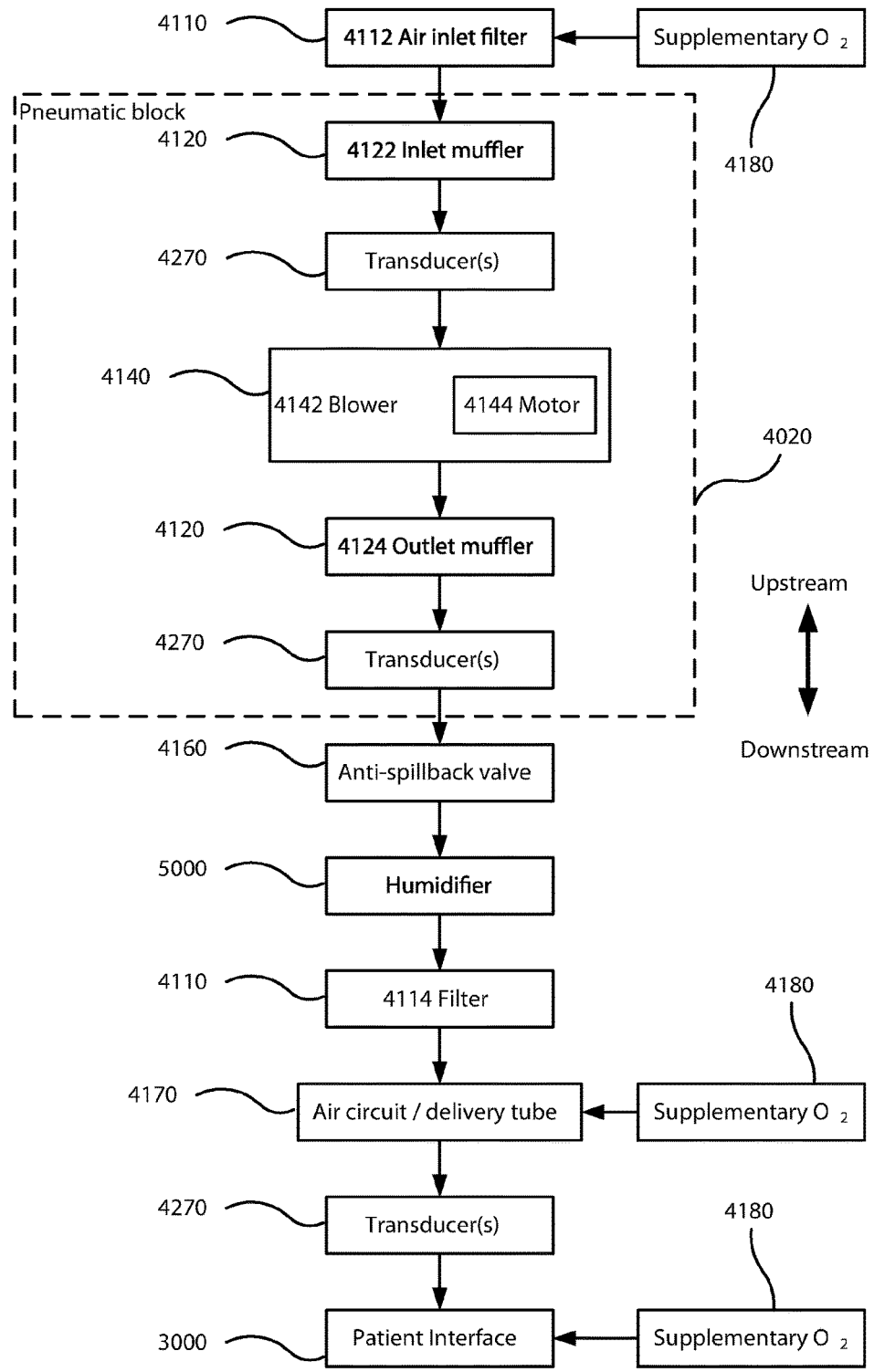

FIG. 4B shows a schematic diagram of the pneumatic circuit of an RPT device 4000 in accordance with one form of the present technology. The directions of upstream and downstream are indicated.

Figure 4C:
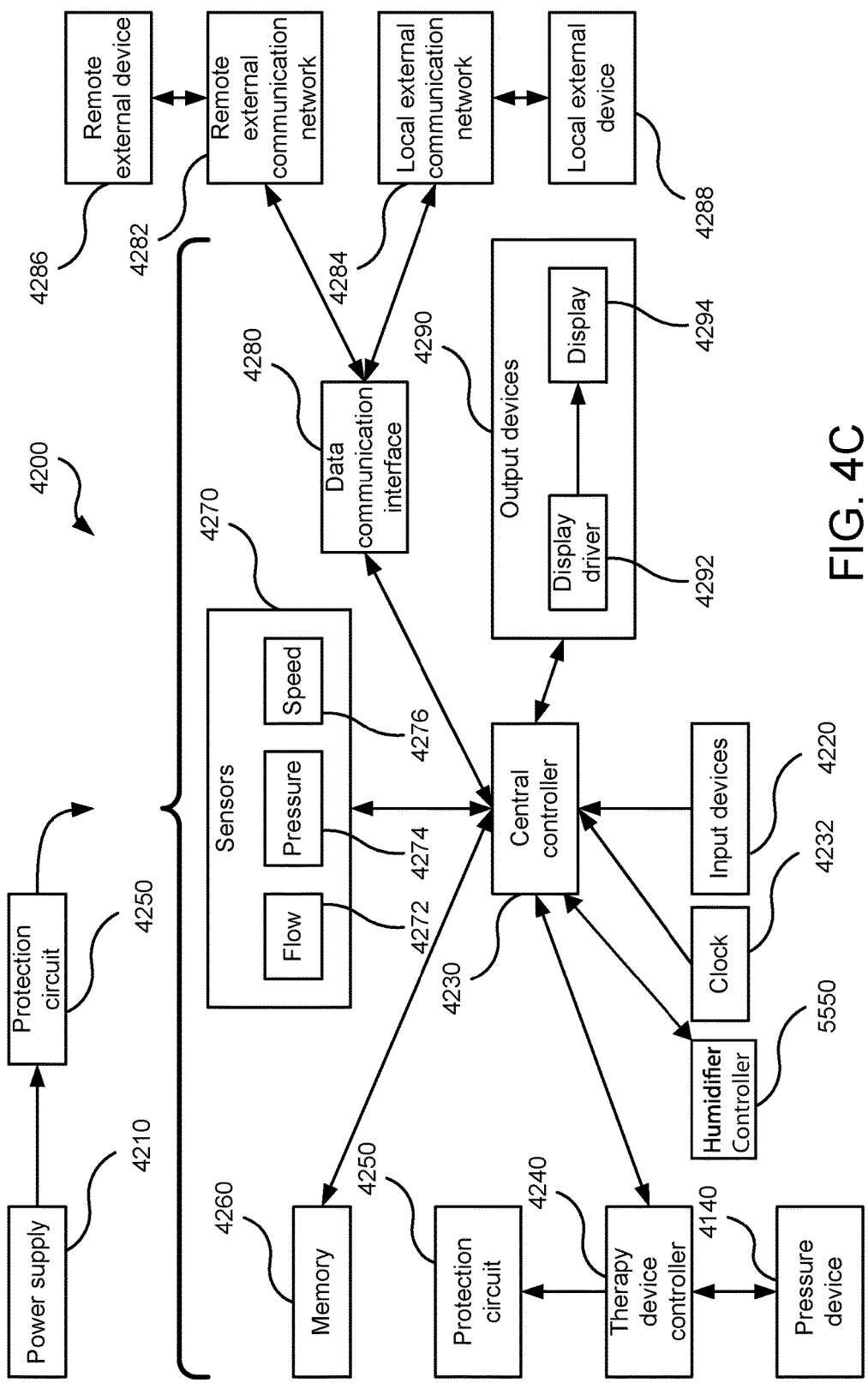

FIG. 4C shows a schematic diagram of the electrical components of an RPT device 4000 in accordance with one aspect of the present technology.

4.5 Breathing Waveforms

Figure 5:
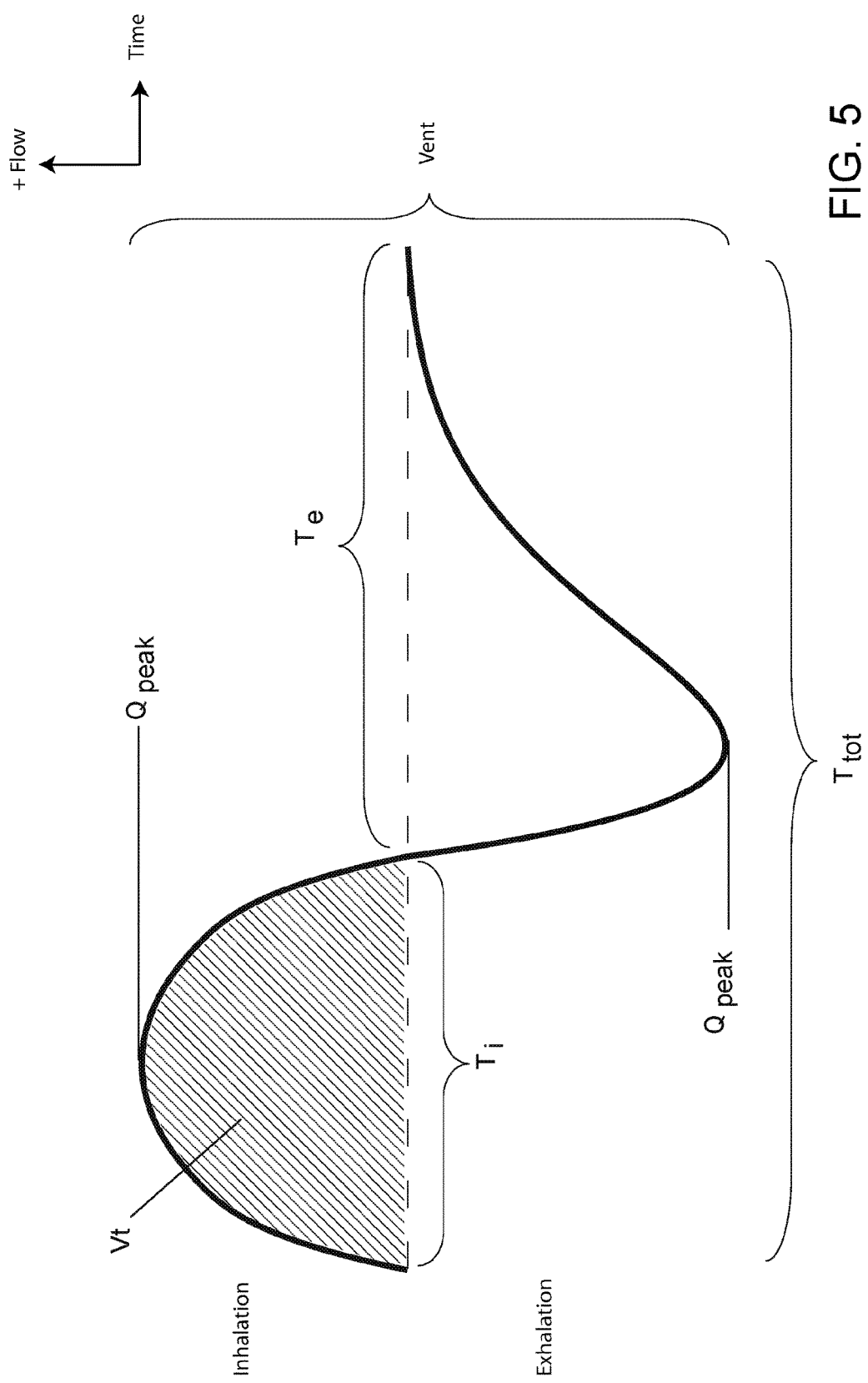

FIG. 5 shows a model typical breath waveform of a person while sleeping. The horizontal axis is time, and the vertical axis is respiratory flow. While the values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/minute. A typical duty cycle, the ratio of Ti to Ttot is about 40%.

4.6 Humidifier

Figure 6A:
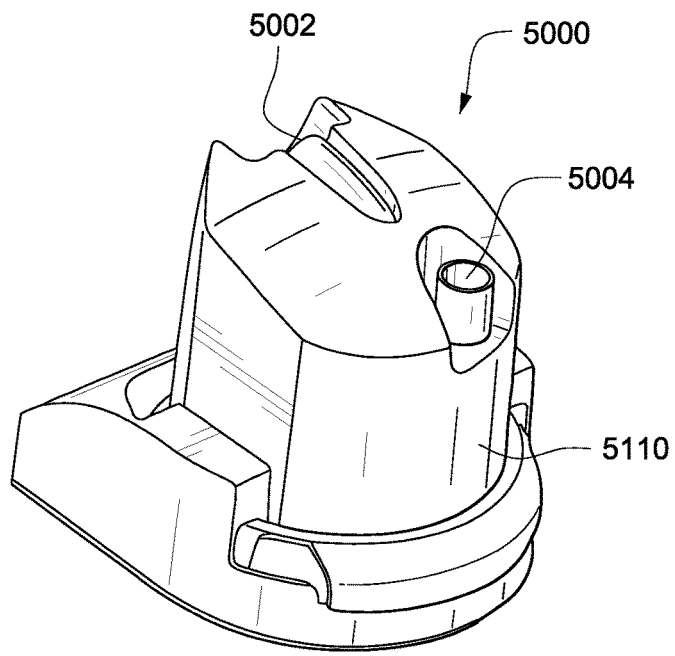

FIG. 6A shows one form of a prior art humidifier.

Figure 6B:
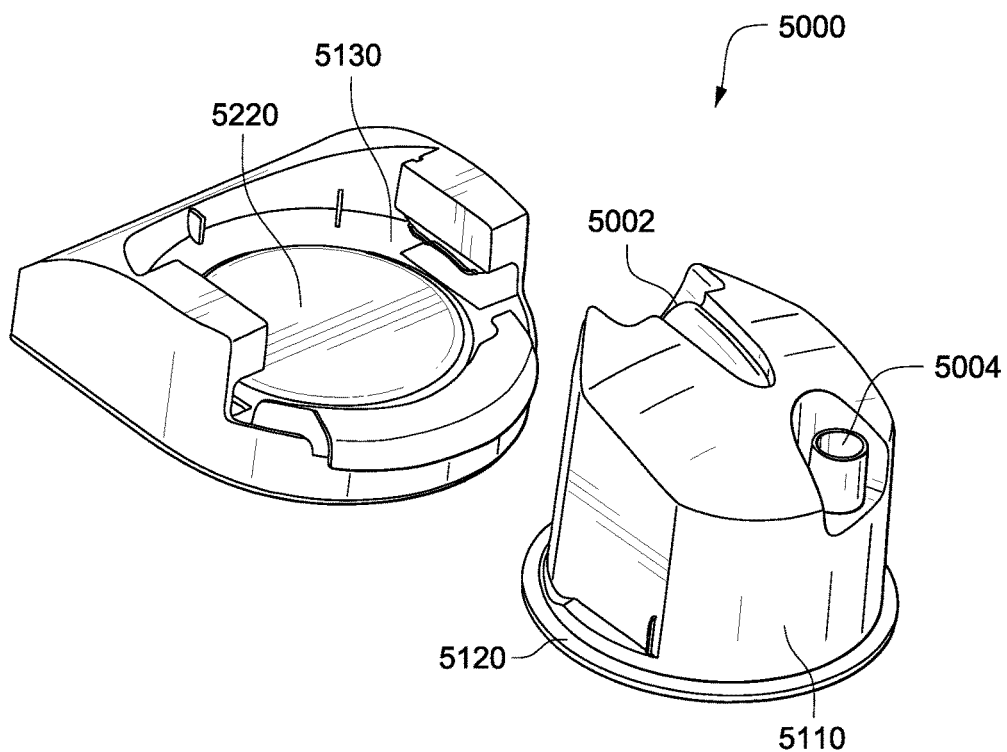

FIG. 6B shows the prior art humidifier of FIG. 6A, showing a reservoir 5110 removed from a humidifier dock 5130.

Figure 7:
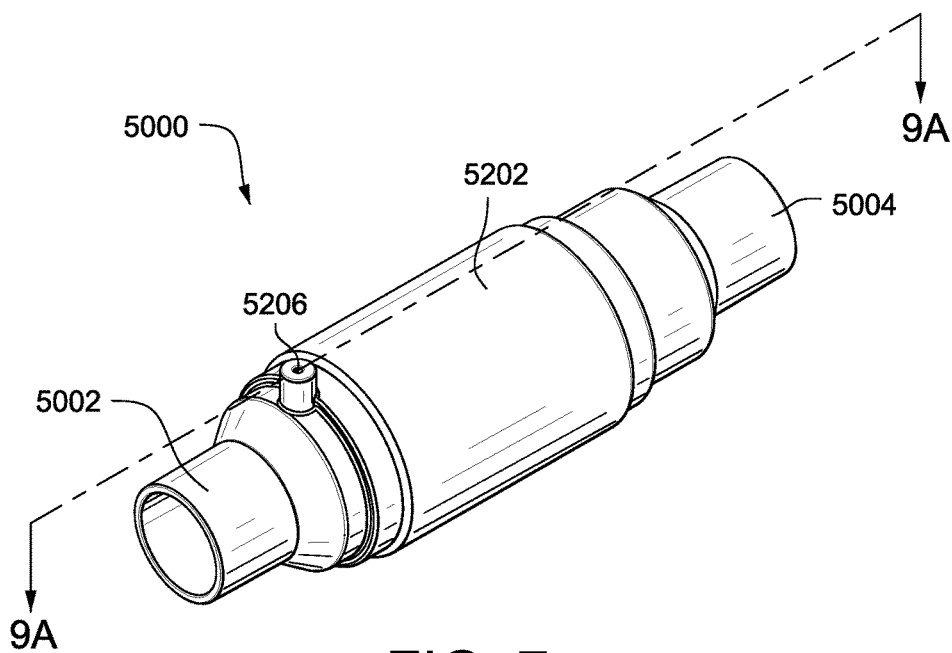

FIG. 7 shows a perspective view of a humidifier 5000 according to one aspect of the present technology.

Figure 8:
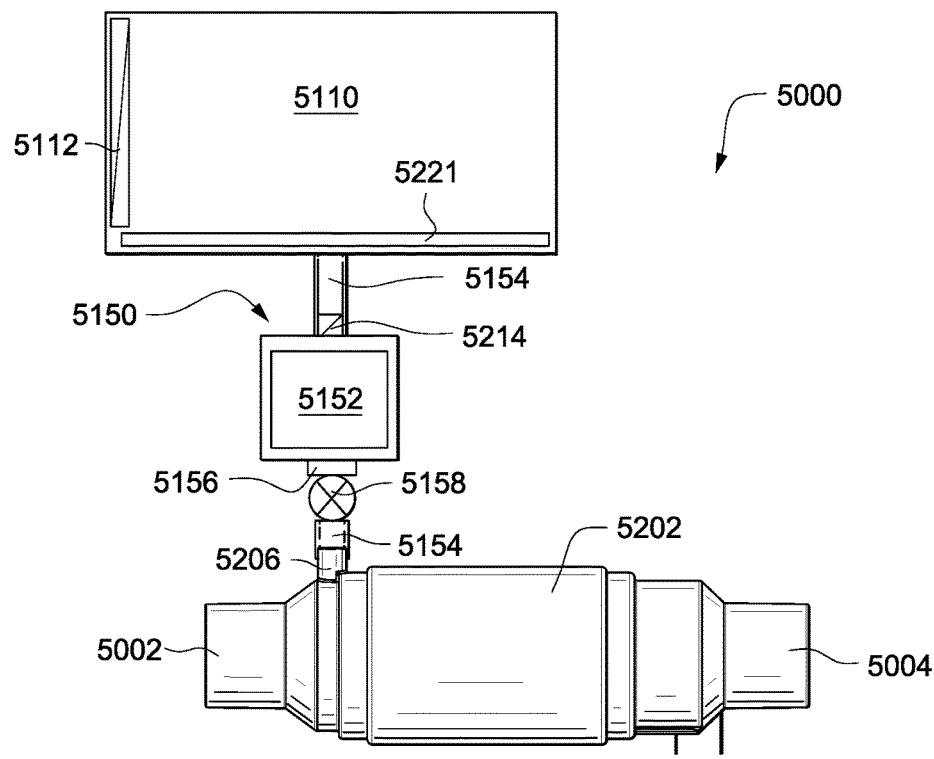

FIG. 8 shows a schematic view of the humidifier of FIG. 7 further comprising a water delivery mechanism 5150 and a reservoir 5110.

Figure 9A:
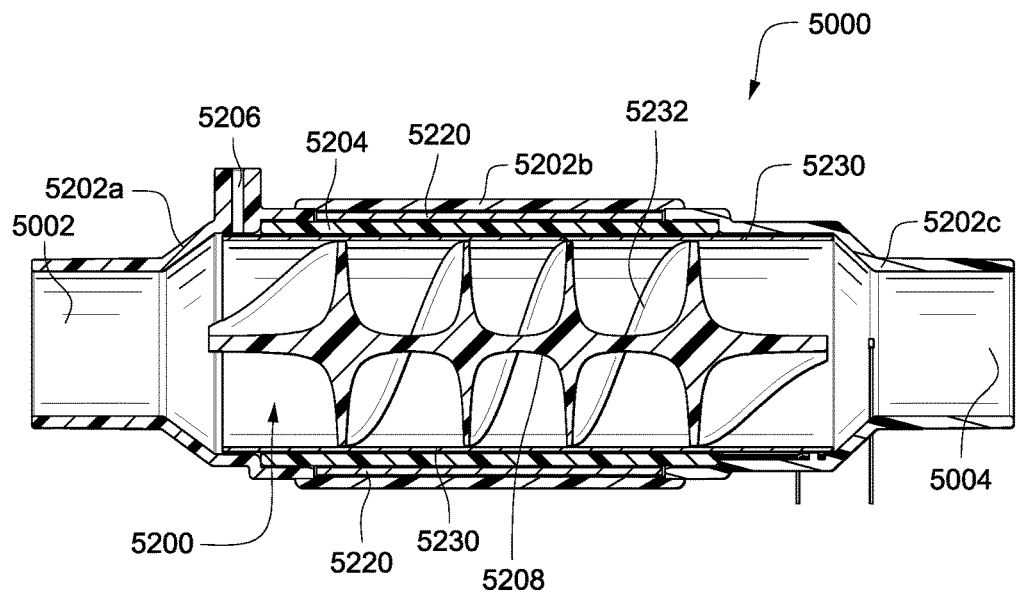

FIG. 9A shows a cross-section view in elevation of the humidifier of FIG. 7.

Figure 9B:
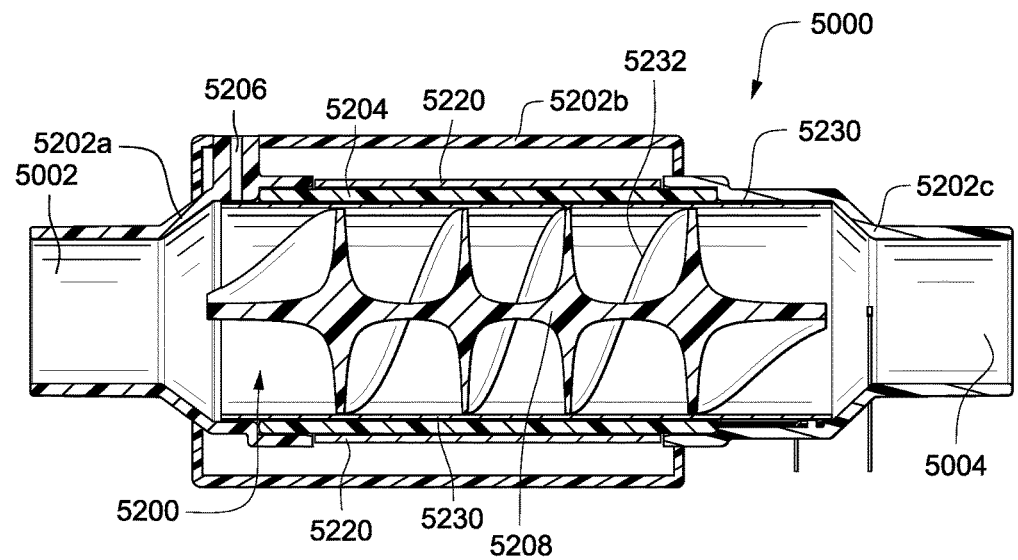

FIG. 9B shows a cross-section view in elevation of a humidifier 5000 according to an aspect of the present technology.

Figure 10:
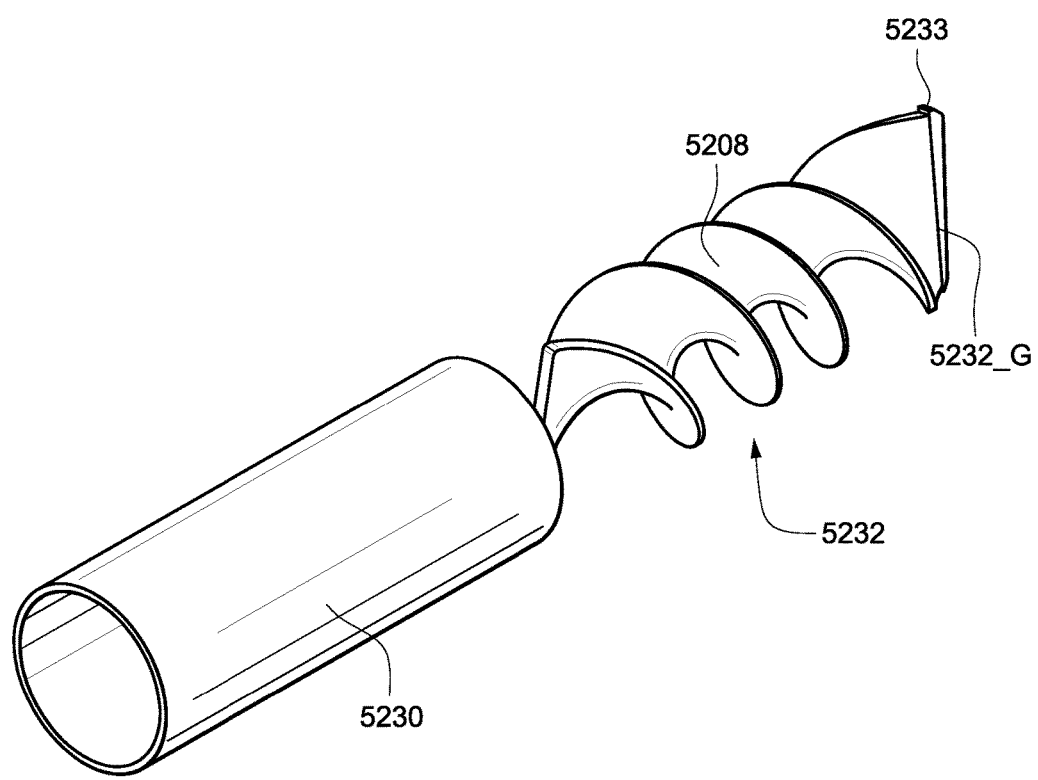

FIG. 10 shows an exploded perspective view of a portion of the humidifier 5000 of FIG. 7 showing a humidifier wick 5230 and a wick frame 5232.

Figure 11:
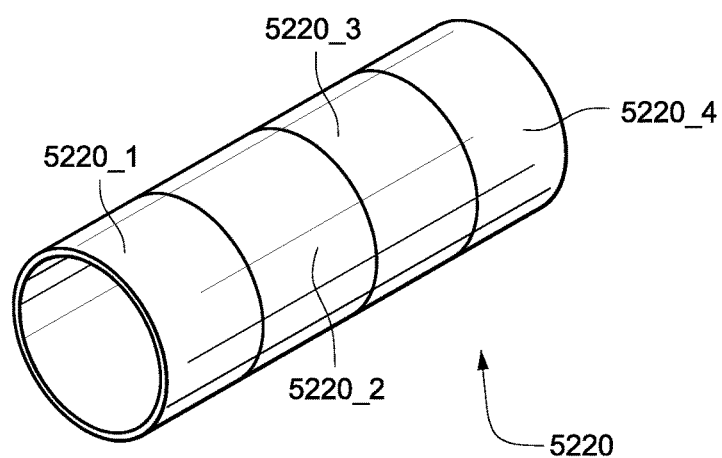

FIG. 11 shows a perspective view of one form of a heating element 5220 for a humidifier according to the present technology, the heating element comprising multiple heating zones.

Figure 12:
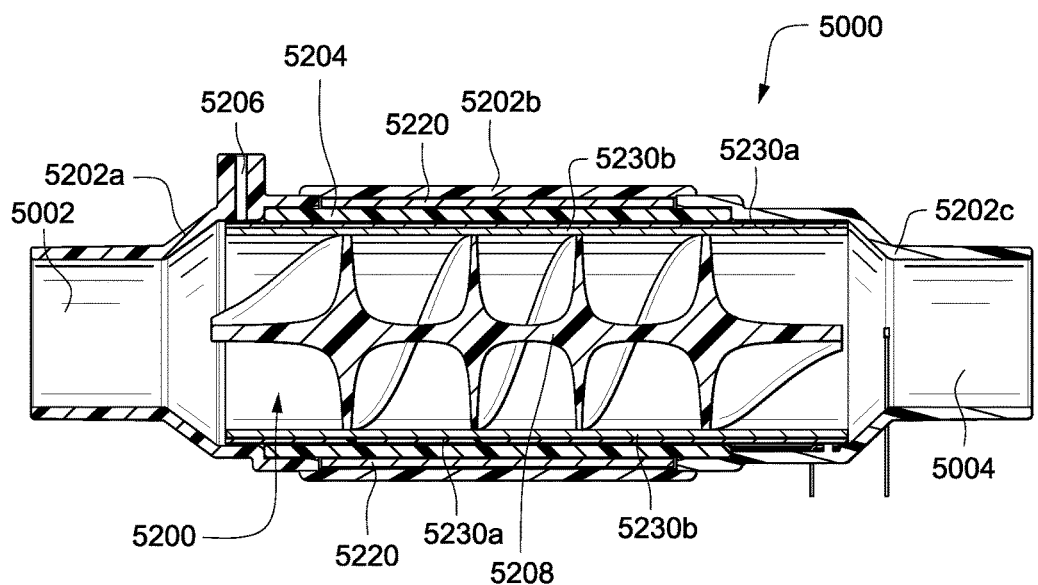

FIG. 12 shows a cross-section view in elevation of a humidifier comprising a multiple layered wick 5230 according to an aspect of the present technology.

Figure 13:
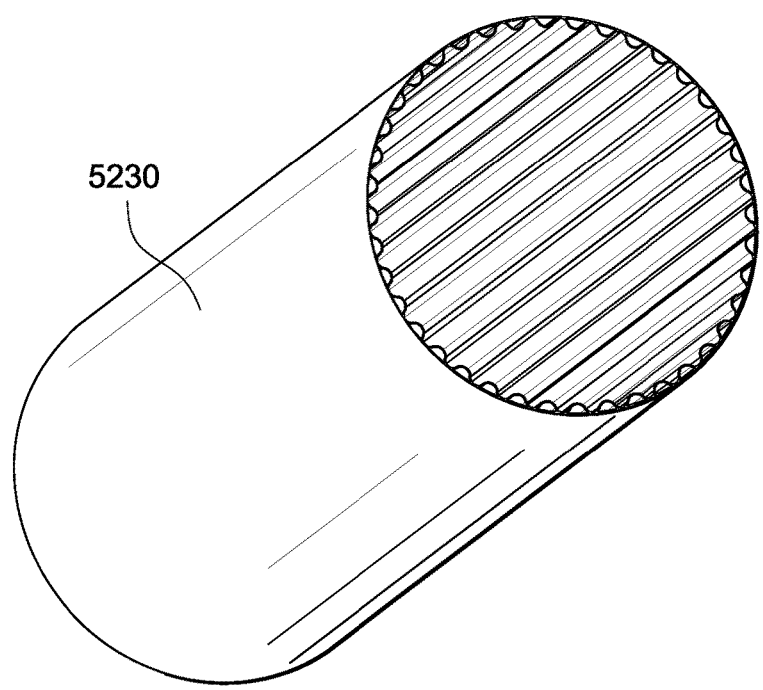

FIG. 13 shows a perspective view of a humidifier wick 5230 according to an aspect of the present technology, the humidifier wick comprising a corrugated inner surface.

FIG. 14 shows a cross-section view in elevation of a humidifier 5000 showing a dry region 5230_D and a wet region 5230_W of the humidifier wick 5230 according to an aspect of the present technology.

Figure 15A:
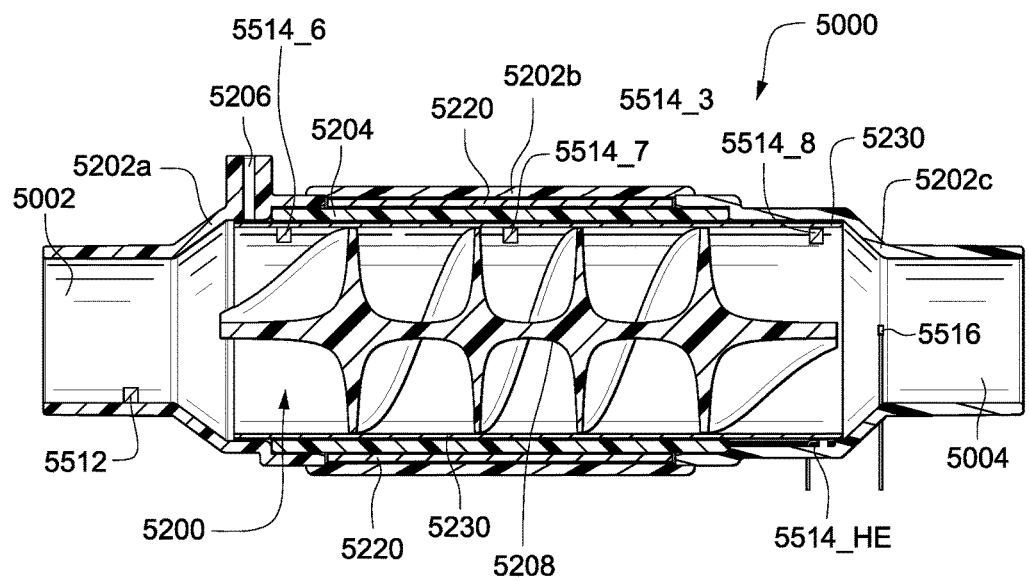
Figure 15B:
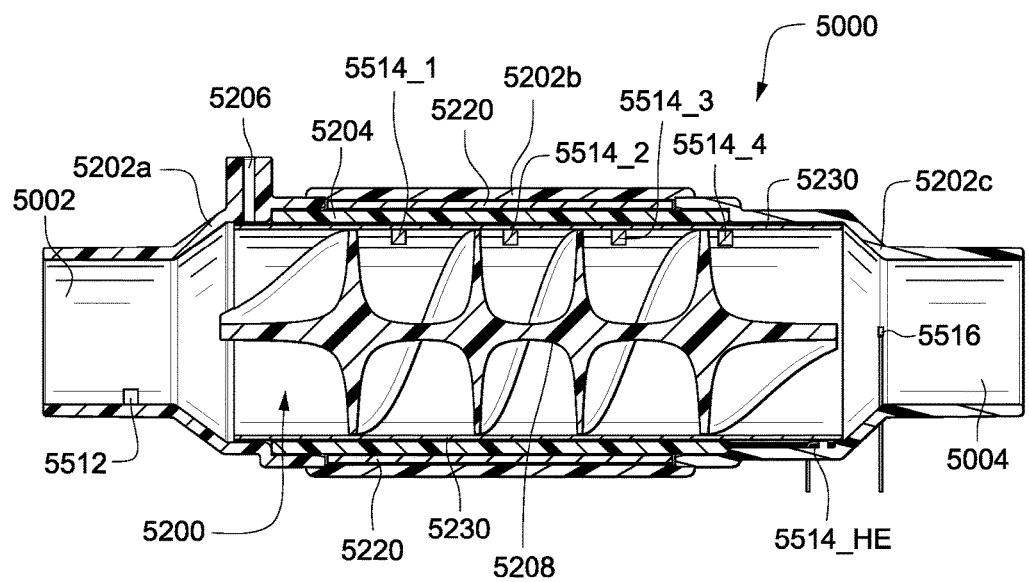

FIG. 15 shows a cross-section view in elevation of a humidifier 5000 including an arrangement of multiple humidifier transducers according to an aspect of the present technology.

Figure 16:
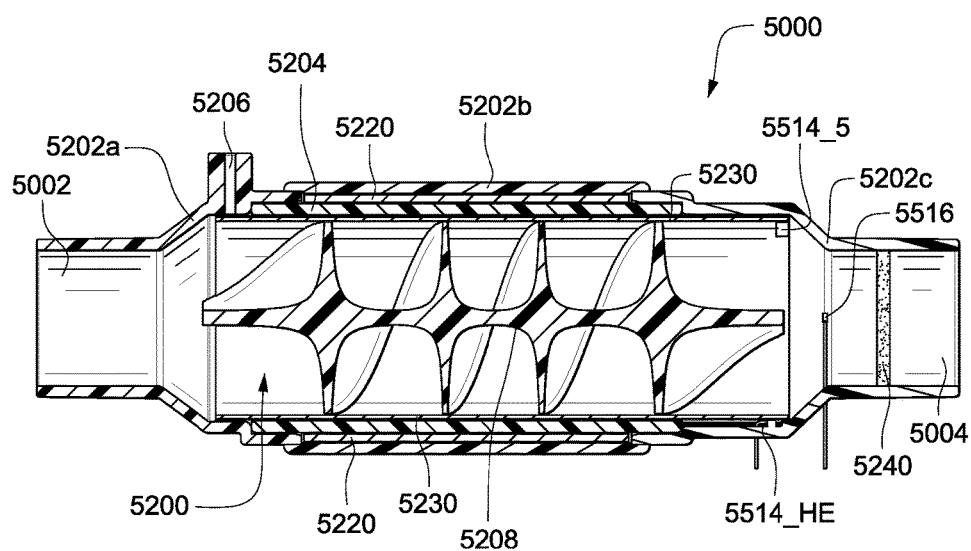

FIG. 16 shows a cross-section view in elevation of a humidifier including a temperature sensor 5514_5 according to a further aspect of the present technology.

Figure 17:
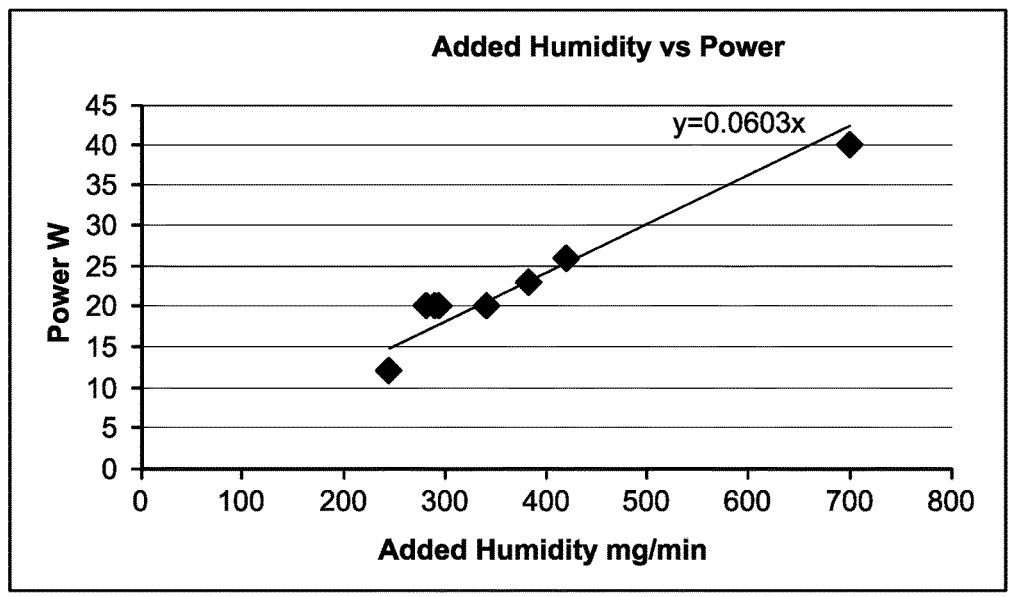

FIG. 17 shows an example of a relationship between a power output of a heating element and the humidity added to the flow of air by the humidifier.

Figure 18:
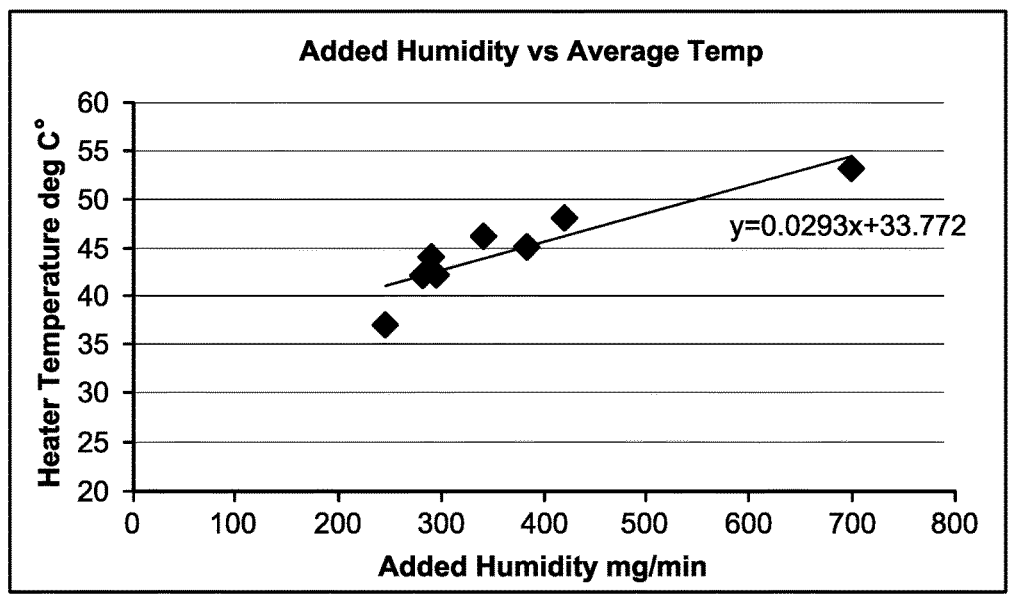

FIG. 18 shows an example of a relationship between a temperature of a heating element and the humidity added to the flow of air by the humidifier.

Figure 19:
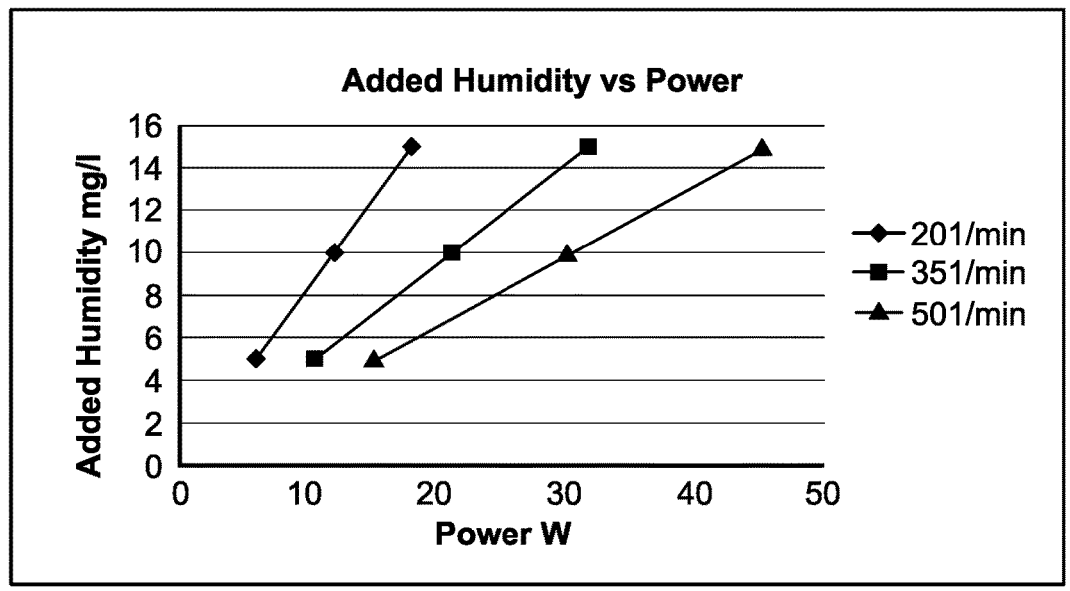

FIG. 19 shows an example of a relationship between a power output of a heating element and the humidity added to the flow of air by the humidifier at various air flow rates.

Figure 20:
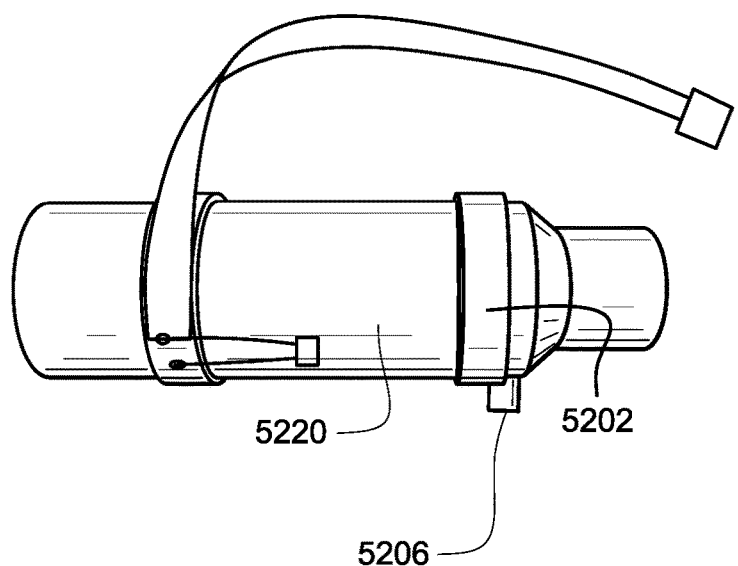

FIG. 20 shows a perspective view of a humidifier 5000 according to one aspect of the present technology, wherein the heating element 5220 comprises resistive wires.

Figure 21:
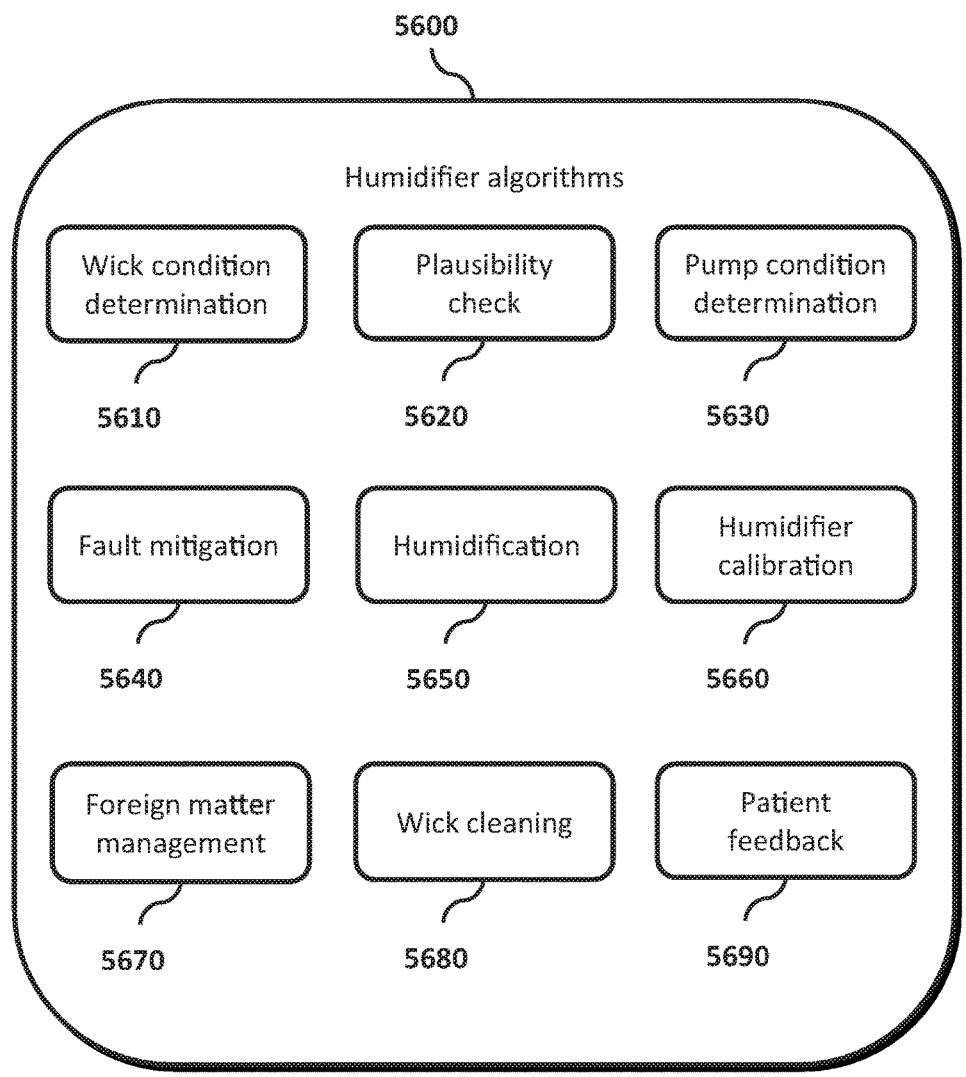

FIG. 21 shows a representation of example humidifier algorithms 5600 according to one aspect of the present technology.

Figure 22:
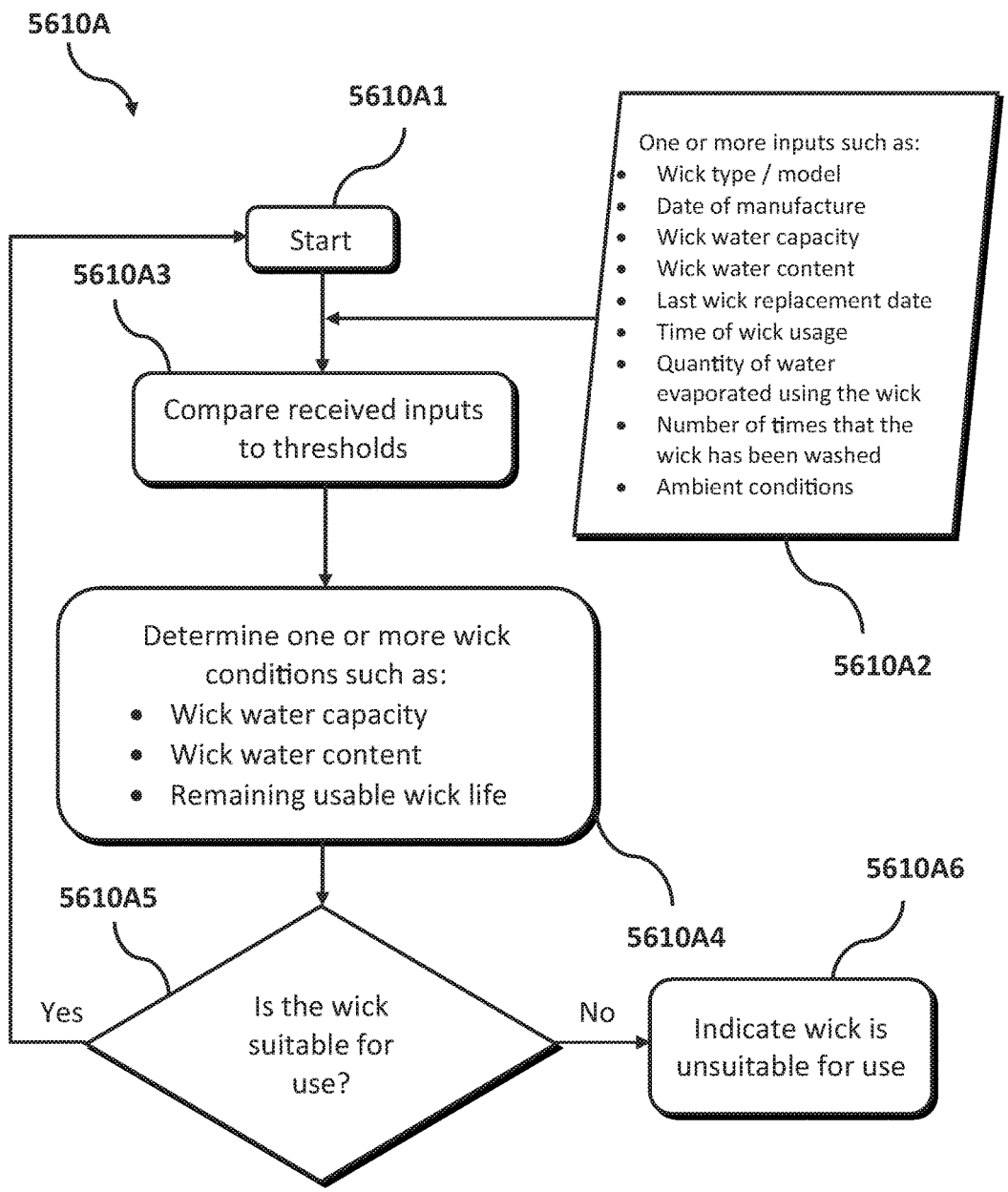

FIG. 22 shows a flowchart of an example algorithm 5610A of a wick condition determination algorithm according to one aspect of the present technology.

Figure 23:
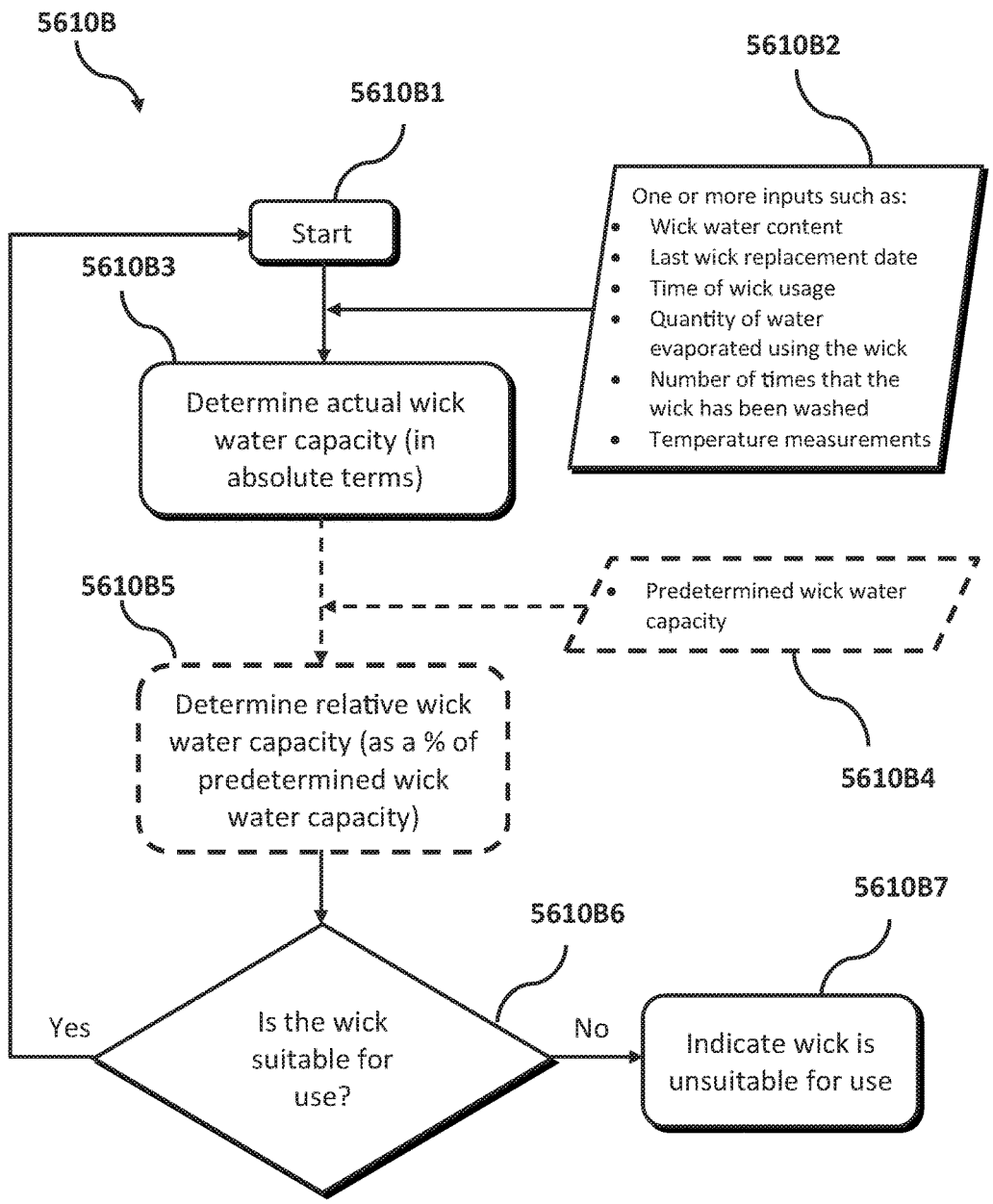

FIG. 23 shows a flowchart of another example algorithm 5610B of a wick condition determination algorithm according to one aspect of the present technology.

Figure 24:
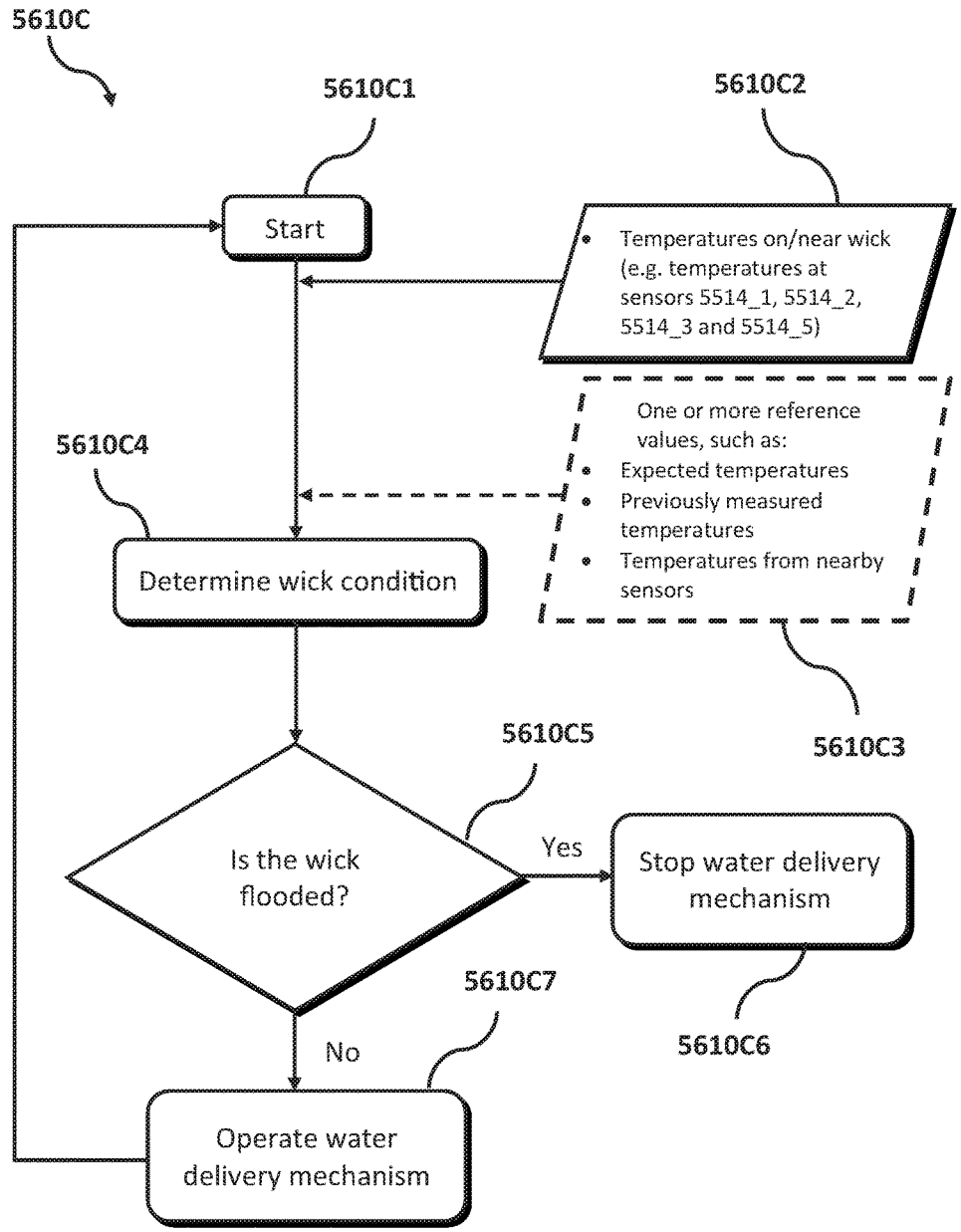

FIG. 24 shows a flowchart of another example algorithm 5610C of a wick condition determination algorithm according to one aspect of the present technology.

Figure 25:
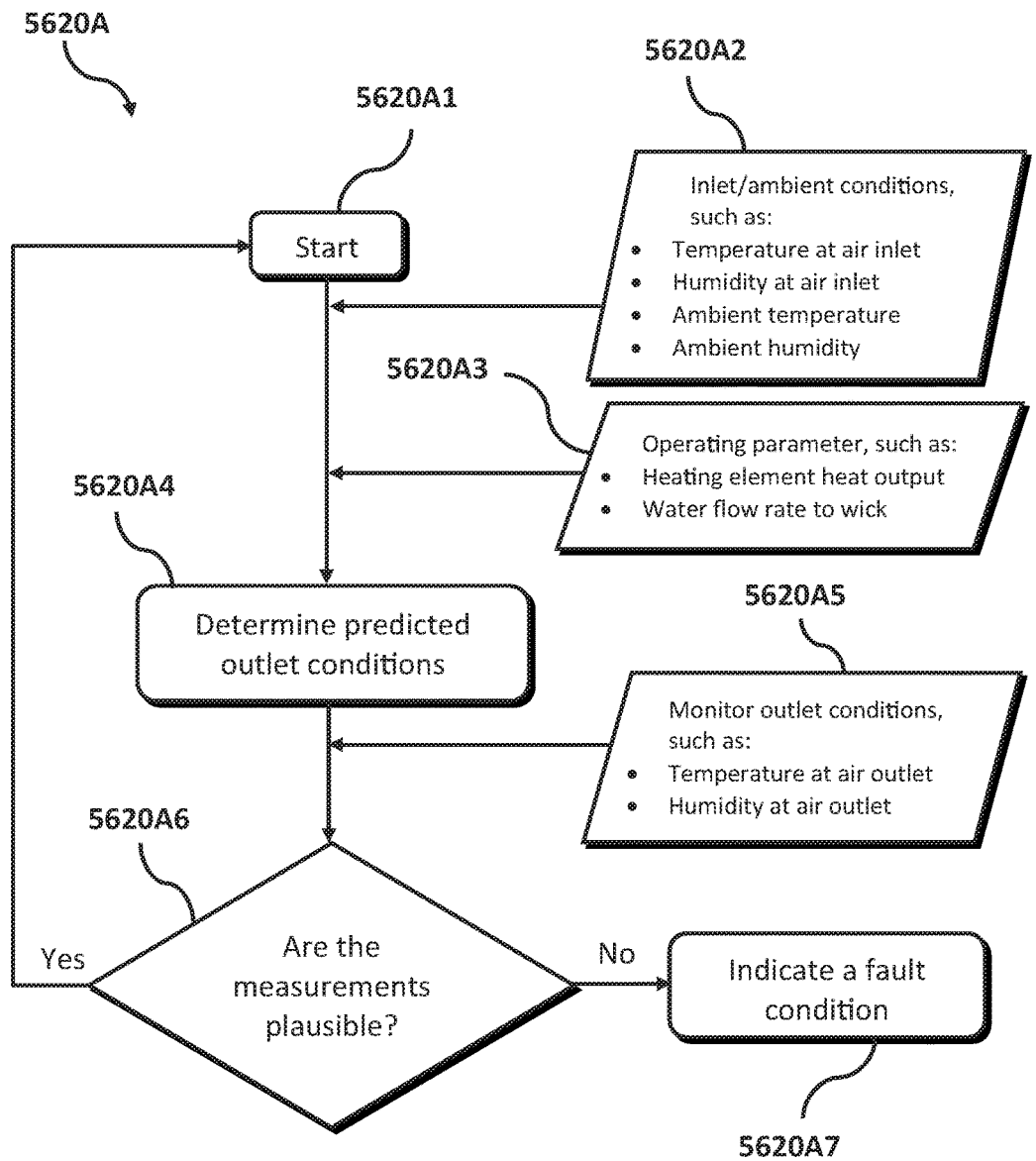

FIG. 25 shows a flowchart of an example algorithm 5620A of a plausibility check algorithm according to one aspect of the present technology.

Figure 26:
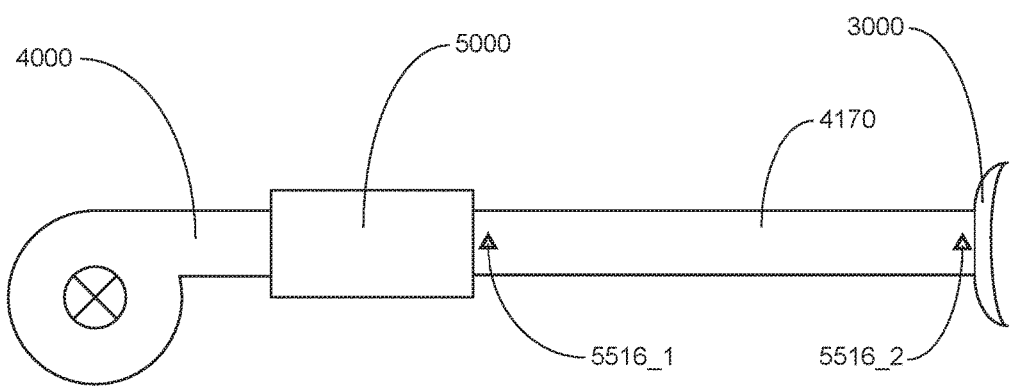

FIG. 26 shows a representation of an example respiratory treatment system comprising an RPT device 4000, a humidifier 5000 and a patient interface 3000 according to one aspect of the present technology.

Figure 27:
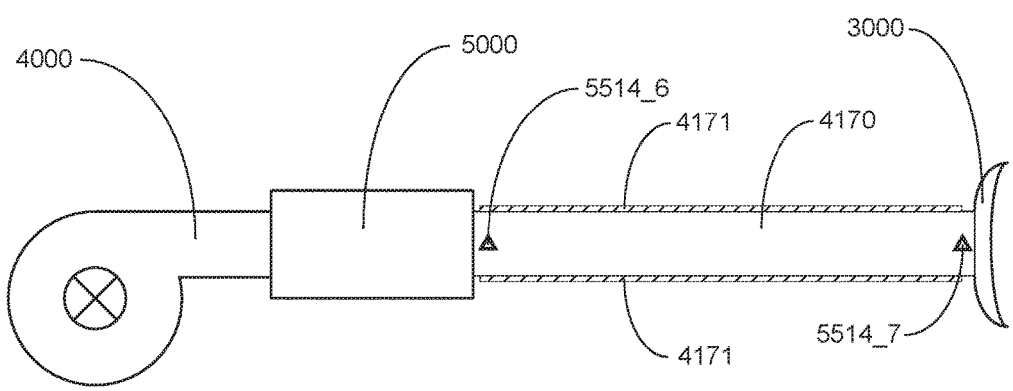

FIG. 27 shows a representation of an example respiratory treatment system comprising an RPT device 4000, a humidifier 5000 and a patient interface 3000 according to one aspect of the present technology.

Figure 28:
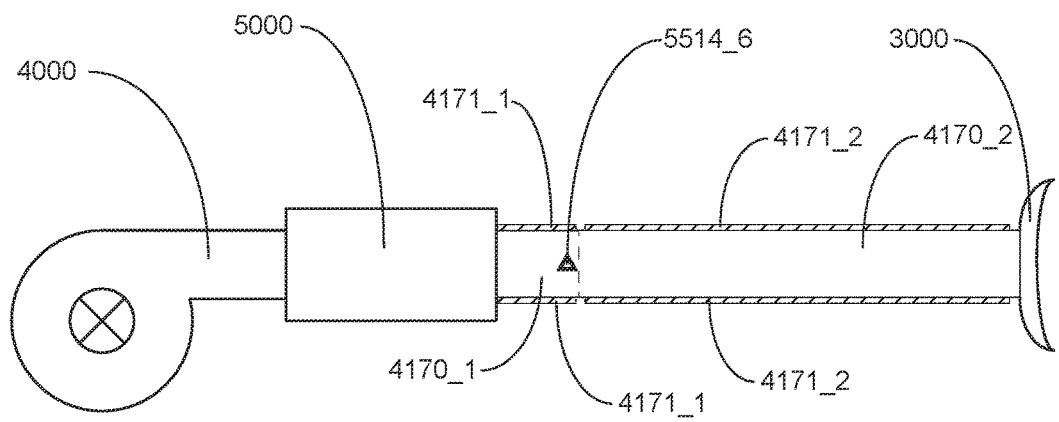

FIG. 28 shows a representation of an example respiratory treatment system comprising an RPT device 4000, a humidifier 5000 and a patient interface 3000 according to one aspect of the present technology.

Figure 29:
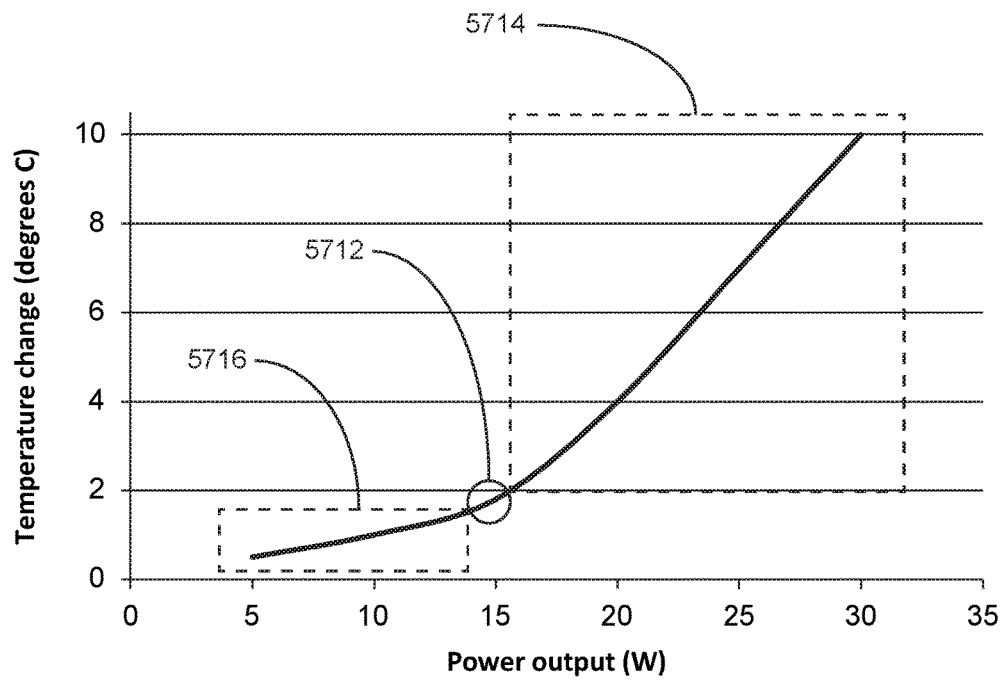

FIG. 29 shows an exemplary graph correlating a temperature change with a power output of a heating element.

Figure 30A:
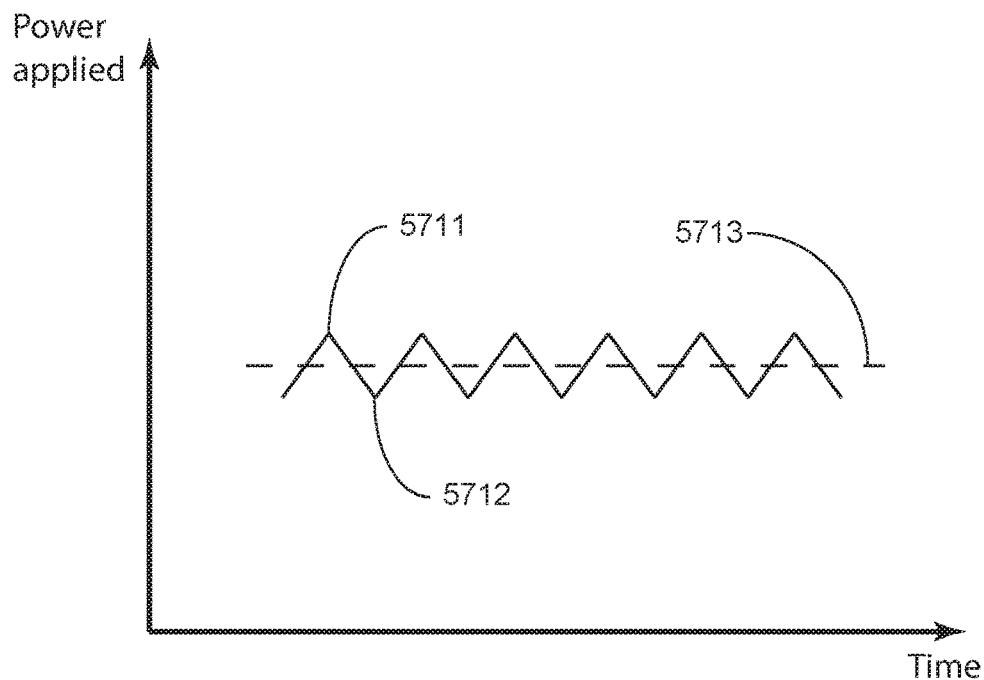

FIG. 30A shows an exemplary graph correlating a power applied by a heating element correlated with time.

Figure 30B:
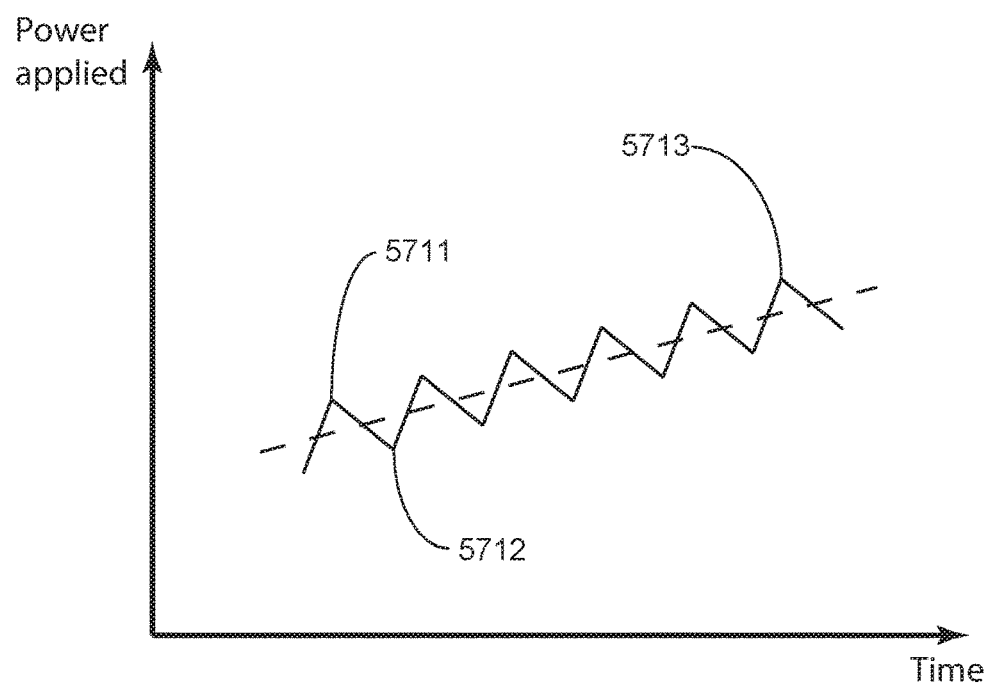

FIG. 30B shows another exemplary graph correlating a power applied by a heating element correlated with time.

Figure 31:
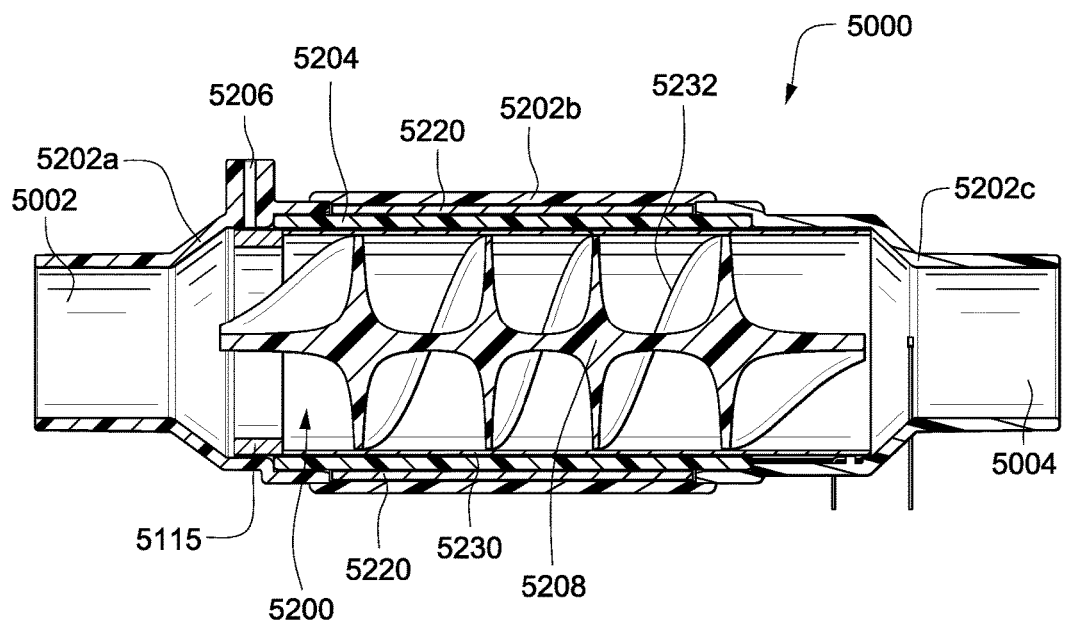

FIG. 31 shows a cross-section view in elevation of a humidifier 5000 including pre-delivery chamber according to an aspect of the present technology.

Figure 32:
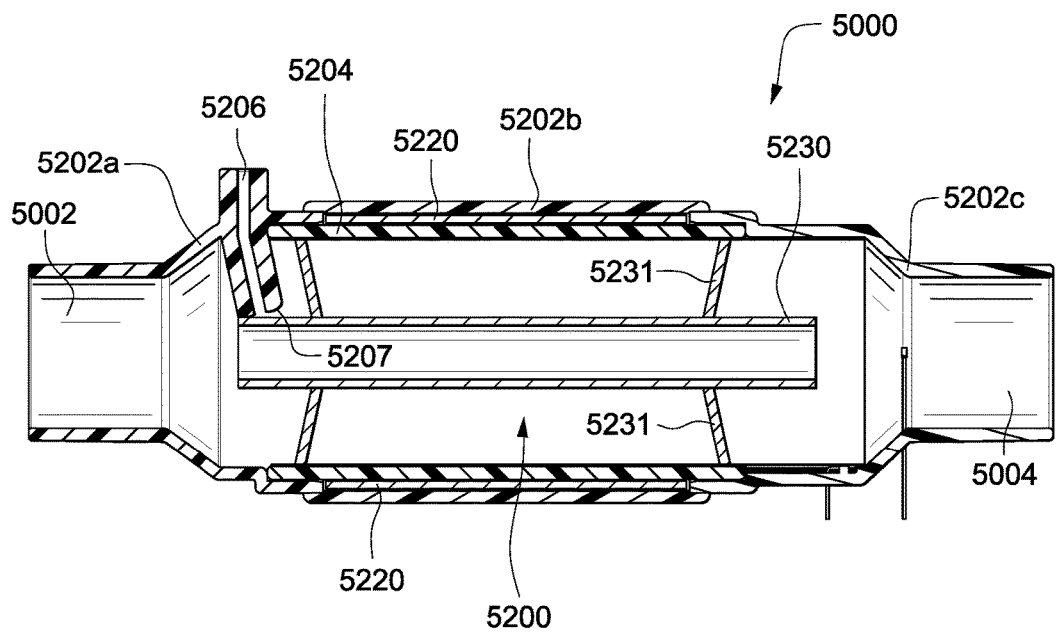

FIG. 32 shows a cross-section view in elevation of a humidifier 5000 including a humidifier wick located towards a centre of the humidifier according to an aspect of the present technology.

Figure 33:
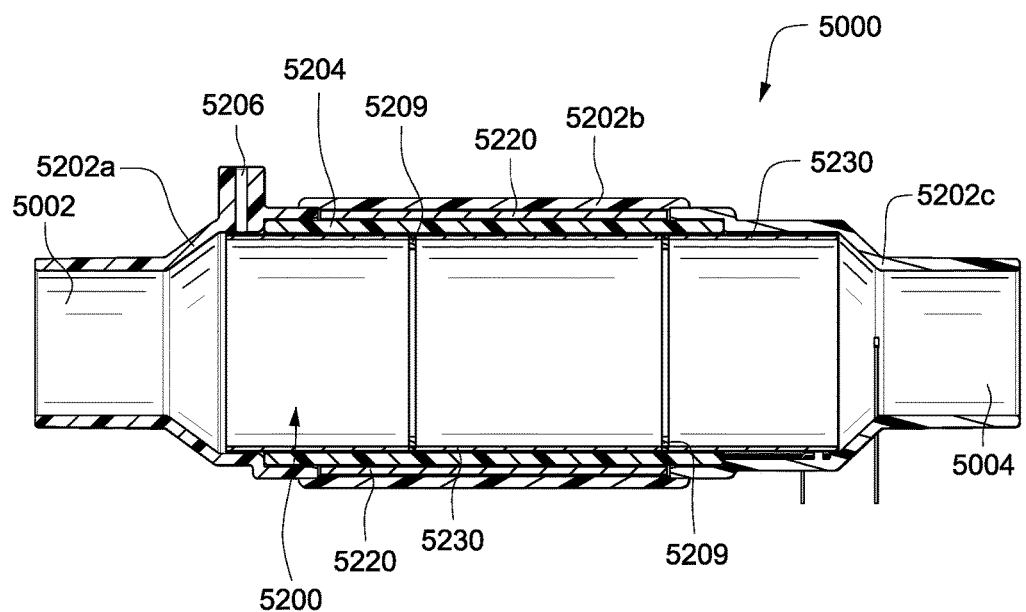

FIG. 33 shows a cross-section view in elevation of a humidifier 5000 including air flow trip elements according to an aspect of the present technology.

Figure 34:
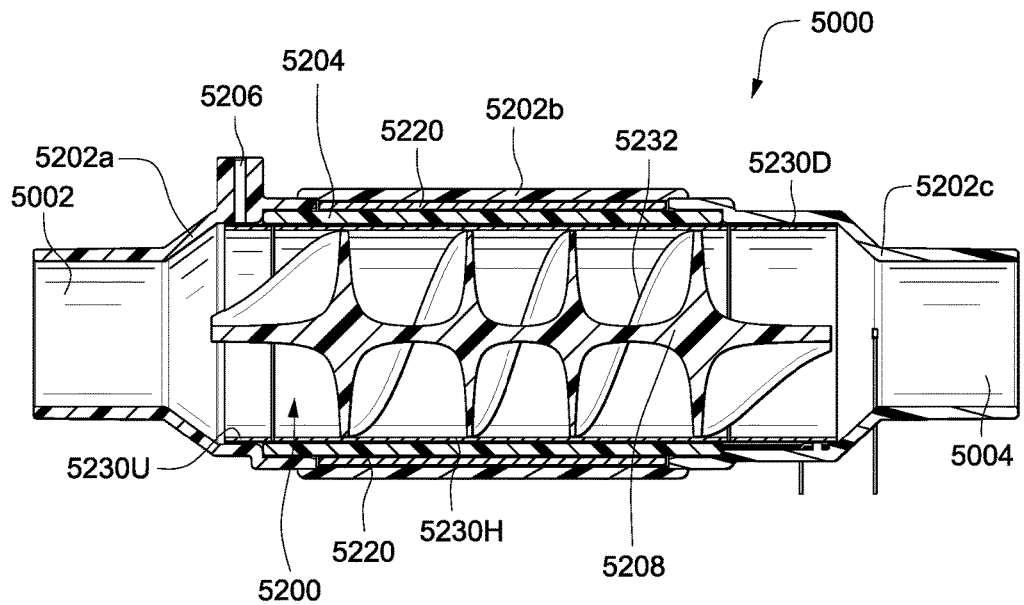

FIG. 34 shows a cross-section view in elevation of a humidifier 5000 including an upstream unheated region of the wick, a heated region of the wick and a downstream unheated region of the wick according to an aspect of the present technology.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Treatment Systems

In one form, the present technology comprises a system for treating a respiratory disorder. For example, a system may comprise an RPT device 4000, a humidifier 5000, an air circuit 4170 and a patient interface 3000.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

In certain examples of the present technology, a supply of air at positive pressure is provided to the nasal passages of the patient via one or both nares.

5.3 Patient Interface 3000

A non-invasive patient interface 3000 in accordance with one aspect of the present technology comprises the following functional aspects (e.g. as shown in FIG. 3): a seal-forming structure 3100, a plenum chamber 3200, a positioning and stabilising structure 3300, and a connection port 3600 for connection to air circuit 4170. The patient interface 3000 may further comprise a forehead support 3700 in some forms, such as that shown in FIG. 3. In some forms, a functional aspect may be provided by two or more physical components. In some forms, one physical component may provide one or more functional aspects. In use the seal-forming structure 3100 is arranged to surround an entrance to the airways of the patient so as to facilitate the supply of air at positive pressure to the airways.

In one form, the patient interface 3000 includes a vent 3400 constructed and arranged to allow for the washout of exhaled carbon dioxide.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.4 RPT Device 4000

A RPT device 4000 in accordance with one aspect of the present technology comprises mechanical and pneumatic components 4100, electrical components 4200 and is programmed to execute one or more algorithms. The RPT device (e.g. as shown in FIG. 4A) has an external housing 4010, for example formed in two parts, an upper portion 4012 and a lower portion 4014. Furthermore the external housing 4010 may include one or more panel(s) 4015. The RPT device 4000 may comprise a chassis 4016 that supports one or more internal components of the RPT device 4000. In one form a pneumatic block 4020 is supported by, or formed as part of the chassis 4016. The RPT device 4000 may include a handle 4018.

The pneumatic path of the RPT device 4000 (e.g. as shown in FIG. 4B) may comprise an inlet air filter 4112, an inlet muffler 4122, a pressure device 4140 capable of supplying air at positive pressure (e.g., a blower 4142), and an outlet muffler 4124. One or more transducers 4270, such as pressure sensors 4272 and flow sensors 4274, may be included in, or coupled with, the pneumatic path.

The pneumatic block 4020 may comprise a portion of the pneumatic path that is located within the RPT device 4000.

The RPT device 4000 may comprise electrical components 4200 such as an electrical power supply 4210, one or more input devices 4220, a central controller 4230, a therapy device controller 4240, a pressure device 4140, one or more protection circuits 4250, memory 4260, transducers 4270 (for example one or more of a flow sensor 4274, a pressure sensor 4272 and a speed sensor 4276), data communication interface 4280 and one or more output devices 4290 (for example a display 4294 and display driver 4292). Electrical components 4200 may be mounted on a single Printed Circuit Board Assembly (PCBA) 4202. In an alternative form, the RPT device 4000 may include more than one PCBA 4202.

The central controller 4230 of the RPT device 4000 may be programmed to execute one or more algorithm modules, such as a pre-processing module, a therapy engine module, a pressure control module, and a fault condition module.

5.4.1 RPT Device Mechanical & Pneumatic Components 4100

5.4.1.1 Air Filter(s) 4110

An RPT device in accordance with one form of the present technology may include an air filter 4110, or a plurality of air filters 4110.

For example, the air filter 4110 may be located at the beginning of the pneumatic path upstream of a blower 4142 as an inlet air filter 4112, or at the outlet of the RPT device 4000 as an outlet air filter 4114. See FIG. 4B.

5.4.1.2 Muffler(s) 4120

In one form of the present technology, an inlet muffler 4122 is located in the pneumatic path, such as upstream of a pressure device 4140 or downstream of the pressure device 4140. See FIG. 4B.

5.4.1.3 Pressure Device 4140

In a form of the present technology, a pressure device 4140 for producing a flow of air at positive pressure is a controllable blower 4142. For example the blower may include a brushless DC motor 4144 with one or more impellers housed in a volute. The blower may be capable of delivering a supply of air, for example about 120 litres/minute, at a positive pressure in a range from about 4 cmH$_2$O to about 20 cmH$_2$O, or in other forms up to about 30 cmH$_2$O. The blower may include a blower as described in any one of the following patents or patent applications the contents of which are incorporated herein in their entirety: U.S. Pat. No. 7,866,944; U.S. Pat. No. 8,638,014; U.S. Pat. No. 8,636,479; and PCT patent application publication number WO 2013/020167.

5.4.1.4 Anti-spill Back Valve 4160

In one form of the present technology, an anti-spill back valve is located between the humidifier 5000 and the pneumatic block 4020. The anti-spill back valve is constructed and arranged to reduce the risk that water will flow upstream from the humidifier 5000, for example to the motor 4144.

5.4.1.5 Air Circuit 4170

An air circuit 4170 in accordance with an aspect of the present technology is constructed and arranged to allow a flow of air between the pneumatic block 4020 and the patient interface 3000. In some forms, the air circuit 4170 may comprise a heating element configured to heat the flow of air travelling through the air circuit 4170. One example of an air circuit 4170 comprising a heating element is disclosed in U.S. Pat. No. 8,733,349, the entire contents of which is incorporate herewithin by reference.

In one form, the air circuit 4170 may comprise a plurality of zones, each comprising a heating element 4171 that may be controlled independently of each other.

5.4.1.6 Oxygen Delivery 4180

In one form of the present technology, supplemental oxygen 4180 is delivered to one or more points in the pneumatic path, such as upstream of the pneumatic block 4020, to the air circuit 4170 or to the patient interface 3000.

5.4.2 RPT Device Electrical Components 4200

5.4.2.1 Power Supply 4210

In one form of the present technology power supply 4210 is internal of the external housing 4010 of the RPT device 4000. In another form of the present technology, power supply 4210 is external of the external housing 4010 of the RPT device 4000.

In one form of the present technology power supply 4210 provides electrical power to the RPT device 4000 only. In another form of the present technology, power supply 4210 provides electrical power to both RPT device 4000 and humidifier 5000.

5.4.2.2 Input Devices 4220

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to the central controller 4230.

In one form the input device 4220 may be constructed and arranged to allow a person to select a value and/or a menu option.

5.4.2.3 Central Controller 4230

In one form of the present technology, the central controller 4230 is a dedicated electronic circuit configured to receive input signal(s) from the input device 4220, and to provide output signal(s) to the output device 4290 and/or the therapy device controller 4240.

In one form, the central controller 4230 is an application-specific integrated circuit. The central controller 4230 may comprise discrete electronic components.

In another form of the present technology, the central controller 4230 is a processor suitable to control an RPT device 4000 such as an x86 INTEL processor.

A processor suitable to control an RPT device 4000 in accordance with another form of the present technology includes a processor based on ARM Cortex-M processor from ARM Holdings. For example, an STM32 series microcontroller from ST MICROELECTRONICS may be used.

Another processor suitable to control an RPT device 4000 in accordance with a further alternative form of the present technology includes a member selected from the family ARMS-based 32-bit RISC CPUs. For example, an STR9 series microcontroller from ST MICROELECTRONICS may be used.

In certain alternative forms of the present technology, a 16-bit RISC CPU may be used as the processor for the RPT device 4000. For example, a processor from the MSP430 family of microcontrollers, manufactured by TEXAS INSTRUMENTS, may be used.

The central controller 4230 may be configured to receive input signal(s), such as input signals from one or more transducers 4270, one or more humidifier transducers and one or more input devices 4220.

The central controller 4230 may be configured to provide output signal(s) such as to one or more of an output device 4290, a therapy device controller 4240, a data communication interface 4280 and humidifier controller 5550.

In some forms of the present technology, the central controller 4230, or multiple such central controllers, may be configured to implement the one or more methodologies described herein such as the one or more algorithms expressed as computer programs stored in a non-transitory computer readable storage medium, such as memory 4260. In some cases, as previously discussed, such processor(s) may be integrated with an RPT device 4000. However, in some forms of the present technology the processor(s) may be implemented discretely from the pressure generation components of the RPT device 4000, such as for purpose of performing any of the methodologies described herein without directly controlling delivery of a respiratory treatment. For example, such a processor may perform any of the methodologies described herein for purposes of determining control settings for an RPT device by analysis of stored data such as from any of the sensors described herein.

5.4.2.4 Clock 4232

The RPT device 4000 may include a clock 4232 that is connected to a central controller 4230. The clock is configured to at least one of monitor, count or record time.

5.4.2.5 Therapy Device Controller 4240

In one form of the present technology, therapy device controller 4240 is a pressure control module that forms part of the algorithms executed by the central controller 4230.

In one form of the present technology, therapy device controller 4240 is a dedicated motor control integrated circuit. For example, in one form a MC33035 brushless DC motor controller, manufactured by ONSEMI is used.

5.4.2.6 Protection Circuits 4250

An RPT device 4000 in accordance with the present technology comprises one or more protection circuits 4250.

One form of protection circuit 4250 in accordance with the present technology is an electrical protection circuit.

One form of protection circuit 4250 in accordance with the present technology is a temperature and/or pressure safety circuit.

5.4.2.7 Memory 4260

In accordance with one form of the present technology the RPT device 4000 includes memory 4260, e.g., non-volatile memory. In some forms, memory 4260 may include battery powered static RAM. In some forms, memory 4260 may include volatile RAM.

The memory 4260 may be located on PCBA 4202. Memory 4260 may be in the form of EEPROM, or NAND flash.

Additionally or alternatively, the RPT device 4000 may include removable form of memory 4260, for example a memory card made in accordance with the Secure Digital (SD) standard.

In one form of the present technology, the memory 4260 acts as a non-transitory computer readable storage medium on which is stored computer program instructions expressing the one or more methodologies described herein, such as the one or more algorithms.

5.4.2.8 Transducers 4270

Transducers may be internal or external of the RPT device 4000. External transducers may be located for example on or form part of the air circuit 4170 humidifier 5000 and/or the patient interface 3000. External transducers 4270 may be in the form of non-contact sensors such as a Doppler radar movement sensor that transmit or transfer data to the RPT device.

In one form of the present technology, one or more transducers 4270 may be constructed and arranged to measure properties of the air, such as at one or more points in the pneumatic path or of ambient air. In another form, one or more transducers 4270 may be configured to measure properties of the RPT device 4000 such as motor speed and/or motor current.

5.4.2.8.1 Flow 4274

A flow transducer 4274 in accordance with the present technology may be based on a differential pressure transducer, for example, an SDP600 Series differential pressure transducer from SENSIRION. The differential pressure transducer is in fluid communication with the pneumatic circuit, with one of each of the pressure transducers connected to respective first and second points in a flow restricting element.

In use, a signal representing total flow Qt from the flow transducer 4274 is received by the central controller 4230.

5.4.2.8.2 Pressure 4272

A pressure transducer 4272 in accordance with the present technology is located in fluid communication with the pneumatic circuit. An example of a suitable pressure transducer is a sensor from the HONEYWELL ASDX series. An alternative suitable pressure transducer is a sensor from the NPA Series from GENERAL ELECTRIC.

In use, a signal from the pressure transducer 4272 is received by the central controller 4230. In one form, the signal from the pressure transducer 4272 may be filtered prior to being received by the central controller 4230.

5.4.2.8.3 Motor speed sensor 4276

In one form of the present technology a motor speed signal is generated. A motor speed signal may be provided by therapy device controller 4240. Motor speed may, for example, be generated by a speed sensor, such as a Hall effect sensor.

5.4.2.9 Data Communication Interface 4280

In one form of the present technology, a data communication interface 4280 may be provided, and may be connected to central controller 4230. Data communication interface 4280 may be connectable to remote external communication network 4282. Data communication interface 4280 may be connectable to local external communication network 4284. Preferably remote external communication network 4282 is connectable to remote external device 4286. Preferably local external communication network 4284 may be connectable to local external device 4288.

In one form, data communication interface 4280 may be part of central controller 4230. In another form, data communication interface 4280 may be an integrated circuit that is separate from central controller 4230.

In one form, remote external communication network 4282 may be the Internet. The data communication interface 4280 may use wired communication (e.g. via Ethernet, or optical fibre) or a wireless protocol to connect to the Internet.

In one form, local external communication network 4284 utilises one or more communication standards, such as Bluetooth, or a consumer infrared protocol.

In one form, remote external device 4286 may be one or more computers, for example, a cluster of networked computers. In one form, remote external device 4286 may be virtual computers, rather than physical computers. In either case, such remote external device 4286 may be accessible to an appropriately authorised person such as a clinician.

The local external device 4288 may be a personal computer, mobile phone, tablet or remote control.

5.4.2.10 Output devices 4290 including optional display, alarms

An output device 4290 in accordance with the present technology may take the form of one or more of a visual, audio and haptic unit. A visual display may be a Liquid Crystal Display (LCD) or Light Emitting Diode (LED) display.

5.4.2.10.1 Display Driver 4292

A display driver 4292 receives as an input the characters, symbols, or images intended for display on the display 4294, and converts them to commands that cause the display 4294 to display those characters, symbols, or images.

5.4.2.10.2 Display 4294

A display 4294 is configured to visually display characters, symbols, or images in response to commands received from the display driver 4292. For example, the display 4294 may be an eight-segment display, in which case the display driver 4292 converts each character or symbol, such as the figure "0", to eight logical signals indicating whether the eight respective segments are to be activated to display a particular character or symbol.

5.5 Humidifier 5000

5.5.1 Humidifier Overview

In one form of the present technology as shown in FIG. 7, there is provided a humidifier 5000 for increasing a moisture content, or absolute humidity, of a flow of air in relation to the ambient air (air surrounding the patient), before the flow of air is delivered to the entrance of the patient's airways. The humidifier 5000 is configured to be coupled directly or indirectly, via an air circuit 4170, to an RPT device 4000 for receiving the flow of air. The humidifier 5000 may be placed upstream or downstream of the RPT device 4000. In one example, the humidifier 5000 may deliver a flow of humidified air at approximately 70%-90% relative humidity such as 80% relative humidity and approximately 25° C.-30° C. such as 27° C.

The humidifier 5000 may comprise an air inlet 5002 to receive a flow of air, and an air outlet 5004 to deliver the flow of air with added humidity.

5.5.2 Humidifier Components
5.5.2.1 Reservoir 5110

According to one aspect of the present technology, the humidifier 5000 may comprise (or be coupled to) a reservoir 5110 as shown in FIG. 8. The reservoir 5110 may be configured to hold a predetermined, maximum volume of water (or other suitable liquids, such as medications, scenting agents or a mixture containing such additives), which may be used to increase absolute humidity of the flow of air.

In one form, the reservoir 5110 may be configured to hold several hundred millilitres of water, for use during at least the length of the patient's sleep in a day. However, in other forms, other sizes such as a smaller reservoir for a portable, travel-friendly system or a larger reservoir for a hospital system may be also suitable. Yet further, a reservoir 5110 may be replaced by, or connected to, a water supply.

According to some arrangements, the reservoir 5110 may comprise, or be coupled to, a water volume detector 5112 by which the amount of water in the reservoir 5110 may be determined. The water volume detector 5112 may determine the volume of water based on one or more of a presence, weight, optical property, ultrasonic property or a head (height) of the water of the reservoir 5110. Any of the mechanisms or methods such as those described in the PCT Patent Application Number PCT/AU2014/050286 may also be suitable for use with the present technology, the entire contents of which is incorporated herewithin by cross-reference.

In some forms, the reservoir 5110 may be configured to heat the water prior to the water entering the humidification chamber 5200, for example by comprising, or being coupled to, a reservoir heating element 5221 as shown in FIG. 8.

In one form, the reservoir 5110 may comprise a plurality of liquid chambers, for example each containing a different fluid. In one example, a first chamber may comprise a volume of water while a second chamber may comprise medication (e.g. dissolved in liquid), or scenting agent (e.g. tea tree oils). The liquids from the plurality of liquid chambers may be mixed prior to or during delivery to the humidifier or within the humidifier 5000. Alternatively the humidifier may deliver one of the liquids from the plurality of liquid chambers at any one time.

5.5.2.2 Water Delivery Mechanism 5150

According to one aspect of the present technology, the humidifier 5000 may comprise a water delivery mechanism 5150 configured to deliver a flow of water from the reservoir 5110 to a humidification chamber 5200 (see FIG. 8). The water delivery mechanism 5150 may comprise a water pump 5152 and a water delivery conduit 5154, and may be in fluid communication with a water feed inlet 5206 to deliver the flow of water to the humidification chamber 5200. The water delivery mechanism 5150 may additionally or alternatively comprise one or more of hydraulic channels, capillary channels or holes. The water delivery mechanism 5150 in some forms may further comprise a valve (e.g. water check valve 5158) for controlling delivery of water from the reservoir 5110 to the humidification chamber 5200 but allowing and preventing delivery of water through to the water feed inlet 5206. For example, the valve may be configured to controllably allow a flow of water to travel from the reservoir 5110 to the humidification chamber 5200, such as only when the humidifier 5000 is in operation.

The humidification chamber 5200 may comprise a water retention feature such as a humidifier wick 5230, which receives the flow of water from the water delivery mechanism 5150. In some forms, the humidifier 5000 may comprise a plurality of water delivery mechanisms 5150 and/or a plurality of water feed inlets 5206 in order to better control a distribution of water in the humidifier wick 5230 (e.g. more uniformly). In this disclosure, a water flow rate will be taken to mean a rate of flow of water from the reservoir 5110 to a humidification chamber 5200 unless explicitly stated otherwise.

The water flow rate(s) that the humidifier 5000 is configured to provide may vary according to factors such as the configuration of the humidifier 5000 and a range of expected operating conditions such as ambient conditions (e.g. ambient temperature/humidity), humidifier operating parameters (e.g. maximum heat output of the heating element 5220, maximum water capacity of the humidifier wick 5230) and/or therapy conditions (e.g. therapy pressure, air flow rate, patient comfort/preference). For example, a change in therapy pressure only may cause a change in the water flow rate, such as due to a response by the humidifier controller 5550, or due to a property of the water delivery mechanism 5150.

In one form, the range of water flow rates able to be provided by the humidifier 5000 may be between 0 ml/min and 2 ml/min, for example between 0 ml/min and 1 ml/min, or between 0 ml/min and 0.5 ml/min. In one form, the humidifier 5000 may be configured to provide one of a number of discrete water flow rates, for example 0.0 ml/min, 0.2 ml/min, 0.4 ml/min, 0.6 ml/min or 0.8 ml/min where the limits of water flow rates able to be provided are 0.0 ml/min and 0.8 ml/min. In other forms, the humidifier 5000 may be configured to provide any water flow rate between an upper limit and a lower limit by providing an analogue control of the flow rate. The upper limit and lower limit of water flow rates may vary according to aspects of a humidifier, such as one or more of: maximum humidity output, maximum flow rate of air through the humidifier, a size of the humidifier and properties of the wick (e.g. exposed surface area and/or water capacity). In cases where at least one liquid other than (or additional to) water is used, the flow rates for each liquid may vary accordingly. The flow rate at a particular time during operation of the humidifier 5000 may also depend on the set of operating conditions at the particular time. For example, a typical value with an air flow rate of 35 l/min and desired added humidity of 15 mg/l requires a water flow of 0.5 ml/min.

It is noted that air flow rates in respiratory therapy may vary over a short term, for example, due to a breath cycle of a patient. However, in some examples, such as determining an appropriate water flow rate based on an air flow rate, a humidifier algorithm may utilise an air flow rate where effects of such variation is removed, or reduced. Thus the air flow rate may be low-pass filtered, or be based on a continuous average, wherein the time constant (e.g. in filtering, or an average time) would be sufficiently long to reduce or remove the effects of in-breath variations.

A pressure of the flow of air (also known as air pressure) in an RPT device and its pneumatic path downstream thereof may vary during therapy, for example between 4 and 30 cmH$_2$O. Thus, the water pump 5152 may be configured to deliver a consistent water flow rate across various air pressures in the humidifier 5000. The water flow rate provided by the water pump 5152 may be independent from (i.e. not be affected by) the air pressure in the humidifier 5000. Such a water pump 5152 would be advantageous in that the air pressure may be varied independently of the amount of humidification provided thereto for improved controllability of the therapy system.

In one form, the water pump 5152 may be a positive displacement type pump. In another form, many other types of pumps such as metered pumps, peristaltic pumps, gravity-fed pumps, or pumps utilising blower pressure may be suitable to be used in the water delivery mechanism 5150. An elevated reservoir (not shown) such as a drip bag may also be suitable and act as a type of gravity fed pump to deliver water.

In some forms, where a water flow rate through the water pump 5152 may be affected by the air pressure, the flow rate through the water pump 5152 may be compensated accordingly. For instance as shown in FIG. 8, the water delivery mechanism 5150 may additionally comprise one or more of a metering mechanism 5156 to measure and/or a water check valve 5158 to control the water flow rate through the water pump 5152. Alternatively, the humidifier controller 5550 may be used to compensate for the effects of any changes to the air pressure, by controlling the water pump 5152 according to the air pressure. A measure of the air pressure may be received by the humidifier controller 5550 as an input to enable such control. In some forms, the humidifier controller 5550 may be used to compensate for the effects of any changes to the air flow rate (e.g. due to a change in leak), by controlling the water flow rate through the water delivery mechanism 5150.

In another arrangement (not shown), a water pump 5152 may be configured to pump water by utilising a pressure such as that generated by the RPT device 4000. The pressure may then be used to draw water from the reservoir 5110 into the humidification chamber 5200. The water flow rate in such an arrangement may be a function of the air flow rate, and thus the humidifier 5000 in this arrangement may further comprise a control valve to regulate the water flow rate.

The humidifier 5000 may in some forms comprise a fault detection mechanism to detect conditions such as blockages in the water delivery mechanism 5150 or a shortage of water in the reservoir 5110, as will be described in further detail below. For example, a blockage in a positive displacement pump may cause its motor to stall, causing the pump to stop. Furthermore, the humidifier 5000 may be configured to detect accumulation of precipitates and/or contamination, such as in the wick 5230, as precipitants or contaminants may adversely affect performance of the humidifier 5000, such as the wick by reducing the ability of the wick 5230 to absorb water.

5.5.2.3 Humidification Chamber 5200

According to one aspect, the humidifier 5000 may comprise a humidification chamber 5200, in which moisture is added to the flow of air, thus increasing the absolute humidity, prior to being delivered to the patient 1000. In one form, a cross-section of which is shown in FIG. 9A, the humidification chamber 5200 may comprise a humidifier wick 5230, a water feed inlet 5206 and a heating element 5220.

The humidification chamber 5200 may be in fluid communication with, and receives water from, the reservoir 5110 through the water feed inlet 5206. The water feed inlet 5206 may comprise an inner diameter of between about 0.5 mm to 3 mm in some forms, such as 1 mm, 1.5 mm, 2 mm or 2.5 mm. The water feed inlet 5206 may be sufficiently large to reduce a risk of obstruction of the water feed inlet 5206, for example due to a build-up of contaminants.

In one form, the humidification chamber 5200 may comprise an outer housing 5202 configured to provide thermal insulation to the outside, as well as to protect an interior of the humidification chamber 5200, such as any components therein. The outer housing 5202 may comprise a plurality of portions such as an inlet portion 5202a, heater cover portion 5202b and outlet portion 5202c that are coupled together. The inlet portion 5202a may comprise the air inlet 5002 and the outlet portion 5202c may comprise the air outlet 5004 as shown in FIG. 9A. The water feed inlet 5206 is shown located in the inlet portion 5202a, but may be located in any one of the portions 5202a, 5202b, 5202c. If multiple water feed inlets 5206 are present, the additional water feed inlets 5206 be located in one or more of the portions 5202a, 5202b, 5202c of the outer housing 5202. The heater cover portion 5202b may be configured to locate and retain the heating element 5220. In some arrangements the heating element 5220 may be retained between an inner housing 5204 and the heater cover portion 5202b of the outer housing 5202 as shown in FIG. 9A. The heating element 5220 may be bonded to the inner housing 5204 in some forms for improved heat conductivity between the heating element 5220 and the humidification chamber 5200. The inner housing 5204 is configured to isolate the heating element 5220 from exposure to moisture, yet allow heat transfer to occur from the heating element 5220 to the humidifier wick 5230.

FIG. 9B shows a humidifier 5000 in another form according to the present technology. In this form, the heater cover portion 5202b of the outer housing 5202 is set away from the heating element 5220 so as to provide an air gap, for example for thermal insulation. The heater cover portion 5202b may also enclose the water feed inlet 5206 for protection as shown in FIG. 9B.

Suitable materials for the inner housing 5204 may include thermally conductive materials, such as aluminium or its alloys, or thermally conductive polymeric/thermoplastic materials such as Polycarbonate/Acrylonitrile Butadiene Styrene (PC/ABS), Polyamide (e.g. Nylon) or Polyphenylene Sulfide (PPS) that may comprise glass or carbon fill for improved thermal conductivity. The inner housing 5204 may be a rigid material suitable to provide rigidity to the humidifier 5000, although in some forms, a flexible structure may be used where other components of the humidifier provide sufficient structural rigidity. Suitable materials for the outer housing 5202 may include polymeric materials such as PC/ABS, and the outer housing 5202 may include elastomeric portions such as thermoplastic elastomer (TPE). The outer housing 5202 may comprise a diameter of between about 10 mm and 50 mm, and be about 1-3 mm thick. The thickness of the inner housing 5204 may be about 1-3 mm, and may vary according to the material used, for example in order to achieve sufficient heat conductivity. It is to be understood that such dimensions and arrangements are exemplary and are not intended to be limiting. It is to be understood that the inner housing 5204 and/or the outer housing 5202 may have a different shape to those shown and/or be formed of a different number of portions, such as one, two, four, five or more portions.

According to one aspect, the water feed inlet 5206 may be in fluid communication with the water delivery mechanism 5150 to deliver water to the humidifier wick 5230 as shown in FIG. 8. In some cases, the humidifier 5000 may comprise a water filter 5214 configured to reduce ingress of foreign matter into the humidification chamber 5200 and/or the wick 5230 through the flow of water. The water filter 5214 may be located at or near an outlet of the reservoir 5110 (as shown in FIG. 8) or upstream (prior to) the water feed inlet 5206. The water filter 5214, or parts thereof, may be configured to be replaceable or cleanable. In some forms (e.g. where quality of the water in the reservoir 5110 is low and/or where hardness of the water in the reservoir 5110 is high), the water filter 5214 may comprise a deioniser (not shown).

In some arrangements (not shown), the water feed inlet 5206 may be located closer to the air outlet 5004 than the air inlet 5002. Such an arrangement may encourage at least some portion of the flow of water in the wick 5230 to travel in an opposing direction to the direction of the air flow in the humidification chamber 5200. Thus, the temperature and humidification gradient within the water in the wick 5230, as well as within the air flow may be optimised to optimise the differential temperature and humidification therebetween in order to improve humidification performance.

According to another aspect, the humidification chamber 5200 may further comprise an air flow baffle 5208 (as shown in FIG. 9A, 9B and FIG. 10) configured to promote turbulence in the flow and/or increase the evaporative surface area, such as by extending a length and/or a residence time during which the flow of air is in the humidification chamber 5200, for example to improve humidification performance. In one form, the air flow baffle 5208 may force the flow of air to travel in a tortuous path, such as a helical path as shown in FIG. 10 to lengthen a path for the air travelling in the humidification chamber. Thus, the air flow baffle 5208 may comprise one or more baffle elements, each of which may be one or more of helical, inclined, curved, or otherwise arranged to increase turbulence and/or to lengthen an air flow path in the humidification chamber 5200. For example, the air flow baffle 5208 may increase the length of the path for the air flow through the humidification chamber 5200 by between approximately 20% and approximately 1000%, in comparison to a linear length of the humidification chamber 5200. In other words, without the baffle 5208 the flow of air through the humidification chamber 5200 would be able to pass directly or linearly from the inlet 5002 to the outlet 5004. However, the addition of the baffle 5208 would serve to increase the distance or lengthen the path that the flow of air must travel to traverse the humidification chamber 5200 from the inlet 5002 to the outlet 5004. For example, the length of the path may be lengthened by between approximately 50% and approximately 750%, such as between approximately 100% and approximately 300%, such as approximately 200%. It will be understood that in various examples of the present technology, the amount of lengthening by the air flow baffle 5208 may vary depending on particular arrangements and/or requirements of the humidifier 5000.

Inclusion of the air flow baffle 5208 in a humidification chamber 5200 may help reduce a size, such as a length, of the humidification chamber 5200, in comparison to a length of the path for the air flow in the humidification chamber 5200 used without such an air flow baffle 5208. Alternatively, or additionally, the humidification chamber 5200 may further comprise one or more air flow trip elements 5209 along an evaporation surface, the air flow trip elements 5209 being configured to improve humidification performance by increasing a turbulence of the air flow. An air flow trip element 5209 (also referred to herein as a 'trip element') may comprise an obstruction to air flow, for example, a raised step, or surface. A trip element 5209 may increase an amount of turbulence (e.g. as measured by a Reynolds number), whereby a thickness of a boundary layer is reduced, encouraging moisture transfer from the humidifier wick 5230 to the air flow. In some forms, the trip element 5209 may present the obstruction to air flow in a direction substantially perpendicular to the direction of the air flow.

One example of a trip element 5209 is an annular prism structure located on an inner periphery of the inner housing 5204 as shown in FIG. 33.

In some forms of the present technology the air flow baffle 5208 may comprise a membrane. The air flow baffle 5208 may also further comprise acoustic elements for noise reduction, such as a tuned chamber (or resonator) configurations, or a number of narrow flow paths configured to encourage development of laminar flow and reduce noise. In one form, the flow paths formed by the air flow baffle 5208 may be configured to provide a high inertance to assist in reducing radiated noise. In some arrangements, the air flow baffle 5208 may comprise variable damping properties for reducing noise and/or vibrations.

In some arrangements, the humidification chamber 5200 may comprise a bypass port for sensing one or more properties of the flow of air as it passes through the humidification chamber 5200.

Additionally, or alternatively, the humidification chamber 5200 may be configured to only add humidity to the flow of air for an inhalation phase of a patient's breath. In one form, the humidifier 5000 may comprise a bypass path which may be used to divert the air flow away from the humidification chamber 5200 for at least a part of a breath cycle, for example using a valve. This may allow for delivery of an air flow to the patient interface 3000 without humidification during some parts of a breath cycle, such as during exhalation.

5.5.2.3.1 Heating Element 5220

The amount of moisture, or absolute humidity, that a flow of air is able to retain in vapour form varies according to a temperature of the flow of air.

In some cases, the flow of air received by the humidifier 5000 may be too cold to retain adequate absolute humidity for delivery to the entrance to the airways of the patient 1000. Furthermore, delivery of cold air may cause discomfort to the patient 1000 as described above. Thus, a humidifier 5000 may comprise a heating element 5220 configured to output heat, for example to heat the flow of air. In one form, the heating element 5220 may be located in the humidification chamber 5200, such as between the inner housing 5204 and the outer housing 5202 as shown in FIG. 9A. Alternatively, or additionally, the reservoir 5110 may comprise a reservoir heating element 5221 to heat water prior to it entering the humidification chamber 5200 as shown in FIG. 8.

The heating element 5220 may heat the flow of air as it passes through the humidifier 5000, as well as to assist humidification in the humidification chamber 5200 such as by heating the humidifier wick 5230. Accordingly, the heating element 5220 may be configured so that it provides sufficient thermal energy for heating and vaporisation at the highest requirements respectively, that is, where the ambient air is cold and dry.

The heating element 5220 may be configured in one of a number of ways whilst meeting the above requirements. In one form, a heating element 5220 may comprise an approximately 10 cm$^2$ surface area that generates a maximum thermal output of 40 Watts. In another form, a heating element 5220 may comprise an approximately 40 cm$^2$ surface area with the same maximum thermal output value of 40 Watts. It should be understood that the maximum thermal output value need not be limited to 40 Watts, and the surface area of the heating element 5220 may be arranged according to aspects of the humidifier 5000, such as its maximum thermal output, size and/or shape. For example, the heating element 5220 may comprise a surface area sized between approximately 5 and 100 cm$^2$, such as between approximately 10 and 60 cm$^2$, or between approximately 20 and 40 cm$^2$. Examples of relationships between a power output of a humidifier 5000 are shown in FIG. 17 and FIG. 19, and an example of a relationship between added humidity and temperature of the heating element is shown in FIG. 18. It should be understood that a size and/or heat output of the heating element 5220 may vary in particular examples of the present technology. For example, a heating element 5220 may be larger in a humidifier 5000 configured to deliver a higher humidification and/or heat than in a humidifier 5000 configured to deliver a lower humidification and/or heat. In some forms, a heating element 5220 for a humidification chamber 5200 comprising a larger surface area would be larger than a heating element 5220 for a humidification chamber 5200 comprising a smaller surface area.

According to one aspect of the present technology, the heating element 5220 may be zoned. That is, the heating element 5220 may comprise multiple sections, or zones, that may be controlled discretely and/or have variable properties. In some cases, variable properties of the zones may include shape, heat output, insulation, proximity to the wick 5230 or proximity to water feed inlet 5206. Yet further, each zone may be controlled independently of each other by the humidifier controller 5550, and in some cases controlled relative to each other. An example of a heating element 5220, which may allow relative control of the zones, is shown in FIG. 11. In this example, the heating element 5220 may comprise four zones 5220_1, 5220_2, 5220_3 and 5220_4, wherein the heating output of each zones may be configured to be varied between 0 to 100% of a total heat output of the heating element 5220, for example 0%, 10%, 20%, 30% and 40% of a total heat output of the heating element 5220. There may be a different number of heating zones, such as two, three, five or more zones and properties of the zones such as their shape, size or maximum heat output may vary. Each zone may be contiguous with another, although they may be spaced apart in some forms. In some forms, each zone may have varying density of electrically conductive circuits therein to achieve varying heating outputs in each zone.

One suitable form of a heating element 5220 may comprise a resistive electrical track on a circuit board. The circuit board may comprise a substrate which could be used as a thermally conductive, electrically resistive barrier between the resistive electrical track and the wick 5230. In one form, the heating element 5220 may comprise a flexible circuit board. In another form, the heating element 5220 may comprise a metallic thermally conductive substrate, which is separated by a dielectric laminate layer from the heating track. Alternative forms of a heating element 5220 may also be suitable such as an inductive heater, if the heating element 5220 is configured to be able to provide a heat output to the wick 5230 and/or the humidification chamber 5200.

A substrate of a heating element 5220 may comprise at least a part of a humidifier wick 5230. Thus, the substrate may comprise an absorptive material such as one or more of: paper, felt, woven material, or any absorbent thin film. An electrical circuit may be disposed onto the substrate to provide the resistive electrical track, such as by printing, by chemical bonding, by an adhesive, or by interweaving for example. In one form, a conductive ink comprising an electrically conductive material may be printed onto the absorptive substrate, whereby the conductive circuit may be formed onto a surface of the absorptive substrate.

The conductive circuit may be connected to one or more sensors such as those described elsewhere in the present document. Additionally, or alternatively, the conductive circuit may comprise a variable resistance portion where the electrical resistance may vary according to a parameter. Examples of variable resistance portions may include a positive temperature coefficient portion, or a negative temperature coefficient portion. A variable resistance portion may be used as a sensing element, for example to sense a temperature at or near the variable-resistance portion according to a change in its resistance. A positive temperature coefficient (PTC) portion may be disposed onto an absorptive substrate by printing PTC carbon ink onto a paper substrate.

In some forms, electrically insulating materials may be disposed onto an absorptive substrate to insulate any conductive portions disposed thereon. For example, an insulating layer comprising dielectric ink may be printed to insulate a conductive circuit comprising conductive inks printed onto a paper substrate.

In another form, the resistive electrical track of the heating element 5220 may comprise a resistive wire. The resistive wire may wrap around an outer housing 5202 as shown in FIG. 20, for example by forming a plurality of loops around the surface. In one example, each strand of wire may be bonded to adjacent strand(s) of wire, such as by an adhesive (e.g. epoxy). In another example, each strand of wire may comprise an insulating layer, which may be further configured to bond to adjacent strand(s) of wire when heat is applied thereto. Thus the plurality of loops of the resistive wire may be formed around the outer housing 5202, and heat may be applied to the heating element 5220 (e.g. externally, or by applying a current through the heating element 5220) to bond the strands together.

As described above, the heating element 5220 may take one of a number of possible forms in shape and/or construction. Thus, it should be understood that although the heating element 5220 is shown (e.g. in FIG. 9A and FIG. 11) to be a cylindrical shape, it need not be limited to such a shape. For example, the heating element 5220 may be constructed as a flat, rectangular sheet, as an extruded arc shape, as a rectangular prism, or a plurality of parallel sheets, among others.

The heating element 5220 may be disposable in some cases. For instance, the entire humidification chamber 5200 may be disposable wherein the heating element 5220 is formed integrally within the humidification chamber 5200 as a part of a disposable component. Alternatively, the heating element 5220 may be configured to be disposable and easily replaced by removal from the humidification chamber 5200, for example by inserting, such as sliding, into the humidification chamber 5200 for installation.

5.5.2.3.2 Humidifier Wick 5230

In one aspect of the present technology, the humidifier 5000 may comprise a water retention feature such as a humidifier wick 5230. The water retention feature (e.g. humidifier wick 5230) may be configured to retain a volume of water, which may be received from the reservoir 5110 for evaporation to humidify the flow of air before it is delivered to the patient 1000. The water retention feature may be shaped so that it may substantially define a part of an air path from the RPT device 4000 to the patient interface 3000. The water retention feature may define, e.g., wholly define, a part of the air path by forming a substantially enclosed path, such as a cylindrically shaped path. In other words, the water retention feature may surround or substantially surround at least a portion of a flow path for the flow of air through the humidifier 5000.

For example, the water retention feature, e.g., the humidifier wick 5230 may have a profiled shape to enclose or substantially enclose at least a portion of the flow path of the air in an axial direction. In the examples depicted in FIGS. 7-10, 12-16, and 31-34, the humidifier wick 5230 may be understood to have a profiled shaped in the form of a substantially circular cross-section. However, it should also be understood that the humidifier wick 5230 may have a profiled shape in the form of a U-shaped cross-section, a V-shaped cross-section, an oval, elliptical, or ellipsoidal cross-section, a polygonal cross-section (i.e., the cross-section may have any number of sides so long as the interior of the humidifier wick 5230 is enclosed), or a parabolic cross-section. It should also be understood that the humidifier wick 5230 may have a profiled shape that completely encloses the interior of the humidifier wick 5230 and at least a portion of the flow path of air therein, e.g., as in a circular cross-section, an oval, elliptical, or ellipsoidal cross-section, or a polygonal cross-section. Alternatively, the humidifier wick 5230 may have a profiled shape that does not completely enclose the interior of the humidifier wick 5230 and at least a portion of the flow path of air therein, e.g., as in a U-shaped cross-section or a V-shaped cross-section.

In an example of the present technology, the humidifier wick 5230 may have a profiled shape that defines a surface which directly contacts the flow of air therethrough and that surface has a profiled shape in that the surface is not substantially planar. In other words, the surface may be understood to be three-dimensional in nature and not two-dimensional.

In order to achieve a target level of humidification output whilst maintaining a small size for the humidifier 5000, it may be beneficial for the water retention feature to wholly define a part of the air path to maximise a contact area with the air flow. Such an arrangement may allow the water retention feature to be disposed entirely around a periphery of the air path, such that for a given length of the water retention feature the area of contact between the air path and the water retention feature is maximised. For example, the humidifier wick 5230 shown in FIG. 10 is shaped as a hollow cylinder to fit within a cylindrically shaped humidification chamber 5200, and define a cylindrically shaped, enclosed air path therethrough. It will be understood that of course, other shapes may also be suitable.

A maximum volume of water able to be retained by the humidifier wick 5230, or a water capacity of the humidifier wick 5230, may be predetermined. In one aspect, the water capacity of the humidifier wick 5230 may be small enough to ensure a short response time of the humidifier 5000. That is, the humidifier 5000 may be able to effect a change to its output (e.g. humidity and/or temperature output) in a relatively short period of time. It would be understood by those skilled in the art that a response time of a humidifier 5000 is a function of the volume of water that is heated. Thus, a humidifier 5000 according to the present technology may comprise a relatively short response time. In some forms of the present technology, a humidifier 5000 may comprise a sufficiently short response time such that a heat and/or a humidity output of the humidifier 5000 may be varied within approximately a minute, such as within 45 seconds, within 30 seconds, or within 15 seconds.

According to another aspect, the water capacity of the humidifier wick 5230 is sufficiently large to allow adequate humidification at the highest flow rates and driest ambient conditions. In one form, the humidifier wick 5230 may thus comprise an adequately large surface area for the water contained therein to come in contact with the air flow through the humidifier 5000. The water capacity of the humidifier wick 5230 may be approximately 10 grams (g), however other values may also be appropriate such as approximately 2 g, 6 g, 15 g, 20 g, 30 g, or any other values therebetween. In other forms, a larger or a smaller water capacity of the humidifier wick 5230 may be suitable depending upon the size and application of the humidifier.

A condition wherein the water capacity of the humidifier wick 5230 is met by the water content in the humidifier wick 5230 may be referred to as 'saturation' or 'flooding' of the wick 5230. In some cases, the humidifier 5000 may be operated such that the humidifier wick 5230 is not saturated during use. Disadvantages caused by saturation of the humidifier wick 5230 may include introduction of water droplets in the humidifier 5000 and/or the air circuit 4170 due to transportation of unabsorbed water from the humidifier wick 5230 (e.g. by entrainment into the air flow). Detection of saturation of the humidifier wick 5230 may be thus desirable, which will be described in further detail below. In some cases, the air circuit 4170 may comprise a portion of the wick 5230, or a secondary wick (or water trap), to ameliorate any potential problems related to such transportation, such as by absorbing any transported water or condensation.

According to one aspect, the wick 5230 may be constructed with non-homogenous geometry and/or construction (e.g. anisotropically or in zones). Thus, one or more properties of the wick 5230 such as the water capacity, surface area exposed to air, or heat conductivity may be varied, such as for each area of the wick 5230 or according to a direction. For instance, the wick 5230 may be non-homogenous along the direction of air flow, or along a distance from the water feed inlet 5206, for example the thickness of the wick 5230 may vary, such as the wick 5230 may become thinner the further away from the water feed inlet 5206. In one form, geometry of the wick 5230 may vary in one or more of the depth, number of layers, the density and/or material of the wick 5230.

For example, the humidifier wick 5230 may comprise one or more layers, such as a first layer 5230a and a second layer 5230b as shown in FIG. 12. The one or more layers may vary in form and/or functions. In one instance, the first layer 5230a may be a transport layer in communication with the water feed inlet 5206, and the second layer 5230b may be an evaporation layer laid over the first layer 5230a and in contact with the flow of air. In this construction, the first layer 5230a may be configured to optimise storage of water per volume and/or fast transport of water, and the second layer 5230b may be configured for improved evaporation characteristics, for example, by increasing an exposed surface area per volume. In some forms, the humidifier wick 5230 may be configured so that one or more layers may be replaced independently of each other, wherein the one or more layers may or may not be identical in form and/or function.

In one form, a humidifier wick 5230 may be anisotropically constructed so that a rate of wicking may be greater in a first direction than in a second direction. Such a construction may allow a distribution of water to be biased in a predetermined manner. For example, the humidifier wick 5230 may be configured so that the rate of wicking in a direction perpendicular to the air flow may be greater than the rate of wicking in a direction parallel to the air flow. Such a configuration may be advantageous in maximising a rate of humidification of the air flow, as more of different portions of the air flow may come into contact with the humidifier wick 5230. The humidifier wick 5230 may be anisotropically configured in one or more directions, such as at 30 degrees, 60 degrees or 90 degrees to the direction of the flow of air.

In some forms, the humidifier wick 5230 may comprise a surface configured to increase a total surface area exposed to the flow of air. This may increase the area over which the water retained by the humidifier wick 5230 is in contact with the air flow and improve humidification efficiency. For instance, the humidifier wick 5230 may comprise a corrugated inner surface as shown in FIG. 13. Other suitable surface types may include one or more of: dimpled, perforated, porous, woven, knitted, textured and sintered surfaces.

A humidifier wick 5230 according to the present technology may comprise a single continuous component, multiple components working as an assembly, or a discontinuous, discrete collection of wicking materials and/or elements. In the present document all or any of the above variations will be referred to as a 'humidifier wick' 5230. A person skilled in the art would understand that the humidifier wick 5230 need not be constructed as a single piece of wicking material.

A humidifier wick 5230 may be located towards an outer periphery of the humidifier 5000, such as in the example shown in FIG. 9A, where the humidifier wick 5230 is shown to at form at least a part of the outer boundary of the air flow path through the humidifier 5000. Additionally, or alternatively, a humidifier wick 5230 may be located towards a centre of the humidifier 5000, for example as shown in FIG. 32, such that the humidifier wick 5230 is located away from the outer boundaries of the air flow path through the humidifier 5000. In the configuration shown in FIG. 32, the humidifier 5000 may further comprise one or more wick struts 5231 to locate and/or secure the humidifier wick 5230 in its intended location. In one form, the one or more wick struts 5231 may be configured to removably engage the inner housing 5204 as shown in FIG. 32 to locate and/or secure the humidifier wick 5230 in relation to the inner housing 5204.

In some forms (e.g. where the humidifier wick 5230 is located toward a centre of the humidifier 5000), the water feed inlet 5206 may comprise a projection extending from an inner surface of the humidifier 5000 towards the humidifier wick 5230, as shown in FIG. 32, in order to deliver liquid from the reservoir 5110. The water feed inlet 5206 may additionally comprise a lead-in 5207, as shown in FIG. 32, in the direction of insertion of the humidifier wick 5230 to allow self-alignment during insertion of the humidifier wick 5230 into the humidifier 5000.

According to another aspect, the humidifier wick 5230 may be heated, for example, by the heating element 5220. One advantage of a heated wick 5230 may be that a rate of evaporation may be controlled. In one form, the humidifier wick 5230 may be thermally coupled to the heating element 5220, for example by contact as shown in FIG. 12, which may advantageously reduce thermal impedance between the humidifier wick 5230 and the heating element 5220.

A humidifier wick 5230 may in some cases be only partially heated by the heating element 5220, for example by the heating element 5220 being in partial thermal contact with of the humidifier wick 5230. In one form, the humidifier wick 5230 may comprise unheated regions upstream and/or downstream of a heating element 5220, as well as a heated region which is in thermal contact with the heating element 5220. A heated region 5230H of the humidifier wick 5230 may overlap the heating element 5220, and an upstream unheated region 5230U and a downstream unheated region 5230D may extend upstream and downstream of the heated region 5230H respectively, where they may not overlap the heating element 5220. The upstream unheated region 5230U and/or the downstream unheated region 5230D may also substantially not overlap any conductive portions of the humidifier 5000 which are in close thermal contact with the heating element 5220, such as the inner housing 5204, as shown in FIG. 34.

An upstream unheated region 5230U may be configured so that water delivered by the water feed inlet 5206 would spread faster within the upstream unheated region 5230U prior to spreading into or through the heated region 5230H of the humidifier wick 5230. For example, the upstream unheated region 5230U may comprise a higher wicking rate than the heated region 5230H. In such an arrangement, water in the upstream unheated region 5230U may be allowed to spread therein prior to occurrence of evaporation in the heated region 5230H. Thus, the humidifier wick 5230 may result with an improved spatial distribution of water therein, where the water boundary is substantially consistent in a direction perpendicular to the air flow direction, such as in a radial direction of the humidifier 5000.

A humidifier wick 5230 may comprise a downstream unheated region 5230D (as shown in FIG. 34), which may be used to provide additional water retention capacity to mitigate against risks of transportation of unabsorbed water from the humidifier wick 5230, for example. For example, a downstream unheated region 5230D may allow the a heated region 5230H of the humidifier wick 5230 to be saturated with water at all times while mitigating a risk of overflowing by providing additional capacity. Additionally, a downstream unheated region 5230D may capture unevaporated moisture which may be entrained and/or transported downstream of the heated region 5230H, such as by the air flow.

In one form, suitable lengths of the upstream unheated region 5230U may be between approximately 5% and approximately 20% of the length of the heated region 5230H, between approximately 8% and approximately 15%, between approximately 8% and approximately 12%, or approximately 10%. For a humidifier 5000 comprising a heated region 5230H with a length of 50 mm, a suitable length of upstream unheated region 5230U may be between approximately 2.5 mm and approximately 10 mm, between approximately 4 mm and approximately 7.5 mm, between approximately 4 mm and approximately 6 mm, or approximately 5 mm. In one form, suitable lengths of the downstream unheated region 5230D may be between approximately 10% and approximately 50% of the length of the heated region 5230H, between approximately 20% and approximately 40%, between approximately 25% and approximately 35%, or approximately 30%. For a humidifier 5000 comprising a heated region 5230H with a length of 50 mm, a suitable length of downstream unheated region 5230D may be between approximately 5 mm and approximately 25 mm, between approximately 10 mm and approximately 20 mm, between 12.5 mm and 17.5 mm, or approximately 15 mm.

Size of the upstream unheated region 5230U and/or the downstream unheated region 5230D may be varied according to aspects of the humidifier 5000, such as its size (e.g. length and/or diameter), humidification output, size of the humidifier wick 5230, water capacity of the humidifier wick 5230, water flow rate and/or number of water feed inlets 5206.

A performance of the humidifier wick 5230 may degrade over time and/or usage, and in some cases the humidifier wick 5230 may no longer be suitable for use. For instance, foreign matter, such as particulates from the water, may collect or build up on the humidifier wick 5230 as it is evaporated. In some cases, collection of foreign matter may reduce water capacity and/or heat conductivity of the humidifier wick 5230. In some cases, the humidifier wick 5230 may deteriorate over time, possibly even without any use of the humidifier 5000. Still further, the foreign matter collected on the humidifier wick 5230 may be removed from the humidifier wick 5230 and be entrained onto the flow of air, which may be undesirable.

Thus, in one aspect of the present technology, the humidifier wick 5230 may be cleaned and/or replaced. Furthermore a condition of the humidifier wick 5230 may be determined, such as its water capacity and/or its remaining usable life, and provide an indication or message when the humidifier wick 5230 needs replacing or to an expected time to replacement.

According to another aspect, a pattern of distribution of foreign matter on the humidifier wick 5230 may be determined and/or controlled. For instance, the humidification chamber 5200 may be configured to encourage collection of foreign matter on the humidifier wick 5230 according to a predetermined pattern. Still further, the predetermined pattern of foreign matter build-up on the humidifier wick 5230 may be used as an indicator of a remaining life of the humidifier wick 5230. For example, the humidifier wick 5230 may be configured so that foreign matter may begin to collect from one predetermined region of the humidifier wick 5230, and for the collection to grow in a predetermined direction. Then, detection of a build-up of foreign matter, for example in a predetermined life-indicator region may be used to indicate that the humidifier wick 5230 may be no longer suitable for use. Thus, determination of a remaining life of the humidifier wick 5230 may be made while the humidifier wick 5230 remains in the humidifier 5000.

A cross-section of the humidifier 5000 (wick frame 5232 not shown) showing an example arrangement of a humidifier wick 5230 in use is shown in FIG. 14. In this example, the humidifier wick 5230 holds a volume of water, however the volume of water may be less than the water capacity of the humidifier wick 5230. Accordingly, the humidifier wick 5230 may be shown to comprise of two regions, a wet region 5230_W and a dry region 5230_D, separated by a water boundary, is shown as 5230_WB. Typically, formation or collection of any foreign matter from water onto the humidifier wick 5230 may predominantly occur at the boundary edge, as this is the point at which particulates are dried. Accordingly, one of the aspects of the present technology relates to a control of the water boundary 5230_WB, through construction of the wick 5230 and/or foreign matter management algorithms, as described further below.

In one form, the wick 5230 may be configured to allow washing, e.g. in a dishwasher, disinfection using another agent, and/or using a microwave. Additionally, or alternatively, the humidifier wick 5230 may comprise an antimicrobial or antibacterial agent such as silver. Yet further, the humidifier 5000 may comprise self-cleaning algorithms (such as a bio-burden reduction algorithm) as will be described further below.

According to one aspect, the humidifier wick 5230 may further comprise added matter such as a medication to be introduced to the flow of air, or a life indicator. The life indicator may comprise a coloured portion which changes colour to indicate to the user or the patient 1000 that the humidifier wick 5230 should be replaced. The humidifier wick 5230 may comprise a medication which may be released by vaporisation to the flow of air to be delivered to the patient 1000.

Suitable materials for the humidifier wick 5230 may include (but not limited to): paper, bicomponent materials comprising hydrophilic fibres, and cellulose fibres. A humidifier wick 5230 may comprise one or more of the above listed materials in one or more arrangements (e.g. flat, corrugated, isotropic, anisotropic, layered etc.) to achieve properties of the humidifier wick 5230 described within the present document.

The humidifier wick 5230 may comprise, or be combined with, the heating element 5220 in some cases. As described elsewhere in the present document, the wick 5230 may comprise a conductive portion (e.g. a carbon ink) which may form resistive tracks for heating, and an absorptive portion (e.g. paper) for water retention and evaporation which also acts as the substrate for the conductive portion. In one form, the heating element 5220 may be coupled (e.g. printed) onto one or both sides of the wick 5230 so as to create an integrated component. The integrated component may further comprise one or more connectors which may be coupled (e.g. printed) onto one or both sides of the wick 5230, for example for connection to the controller 5550.

The humidifier wick 5230 may be constructed from a sheet in some forms. For example, the humidifier wick 5230 may comprise a paper sheet which has been formed into a tubular shape, such as to conform to a shape to the humidifier chamber. The sheet may be bonded by adhesives, one suitable example of which is a hot melt open adhesive web. However, it will be readily understood that a number of known alternatives may be also suitable.

The humidifier wick 5230 may comprise one or more humidifier transducers. The humidifier transducers and humidifier algorithms which may receive inputs from the humidifier transducers are described in further detail below.

In another aspect, the humidifier wick 5230 may be configured in a shape to facilitate easy insertion and/or removal with respect to the humidification chamber 5200. In one form, a portion of the humidifier wick 5230 such as a tab (not shown) may be configured to be accessible for removal while the humidifier wick 5230 is in its operating position. Yet further, the humidifier 5000 may be configured as shown in FIG. 14 such that a component (such as an outer housing component 5202_c) may be removed to allow access to the humidifier wick 5230. Additionally, or alternatively, the humidifier wick 5230 may be configured in a frustro-conical shape complementarily to a similarly shaped humidification chamber 5200, so that it would self-locate during insertion into its operating position.

5.5.2.3.3 Wick Frame 5232

In some forms of the present technology, the humidifier 5000 may comprise a wick frame 5232, such as an example shown in FIG. 9A, FIG. 9B and FIG. 10. The wick frame 5232 may be coupled to the wick 5230 (e.g. chemically bonded and/or mechanically coupled), for instance to locate and/or shape the wick 5230 (e.g. in a predetermined location and/or shape), maintain the wick 5230 in close proximity to the heating element 5220, and/or to prevent an increase in flow impedance which may occur due to a deformation of the wick 5230. The wick frame 5232 may promote, or maintain, thermal contact between the wick 5230 and the heating element 5220 by assisting in locating and/or shaping the wick 5230 as designed (e.g. by maintaining the wick 5230 in a cylindrical shape as shown in FIG. 10). In a form shown in FIG. 10, the wick frame 5232 may comprise a wick locator 5233 such as a shoulder as shown, to assist in location of the wick 5230 in relation to the wick frame 5232 in assembly.

The wick frame 5232 may be further configured to assist in removal and/or insertion of the wick 5230 with respect to the humidifier 5000, for instance by providing a grip 5232_G to assist a user and/or the patient 1000 to locate and/or hold the wick frame 5232 for insertion, removal and/or handling of the wick frame 5232. In one form, the grip 5232_G may comprise a flat plate-like configuration to allow the patient/user to hold the wick frame 5232, although any number of other shapes and/or configurations may be also suitable. The grip 5232_G may extend past an open end of a surrounding component, such as an inner housing 5204, although in some forms, the grip 5232_G may be accessible from an exterior of the humidifier 5000, such as to allow removal of the wick frame 5232 and/or the wick 5230 from an exterior of the humidifier 5000 (e.g. without disassembly of any other components of the humidifier 5000). Additionally, or alternatively, the wick frame 5232 may comprise a connector (not shown) to removably locate and/or secure the humidifier wick 5230 to the humidifier 5000, such as by a bayonet, a thread, a friction-fit surface or a pin. Those skilled in the art will recognise that a number of other connectors may be also used to secure and/or locate the humidifier wick 5230 to the humidifier 5000, such as to the outer housing 5202.

The grip 5232_G may be marked (e.g. using colours and/or indicators) for identification, and/or textured to assist the users to hold onto the grip 5232_G. In some forms, where the humidifier wick 5230 is disposable, the wick frame 5232 may be configured to be disposed with the humidifier wick 5230, for example by being integrally formed with the humidifier wick 5230. In other cases, the wick frame 5232 may be configured to accept and hold the humidifier wick 5230, for example, so that the wick 5230 may be replaced while the wick frame 5232 is removed from the humidifier 5000. Then the wick frame 5232 may accept a new wick 5230 and be inserted into the humidifier 5000. In some forms, the wick frame 5232, the wick 5230 and the heating element 5220 may be non-removably coupled together and configured to be disposable as a unit.

According to another aspect, the wick frame 5232 may be configured to be printed by a 3-D printer, for example by the patient 1000, or a caregiver, such as in a hospital or in a home environment. Alternatively, or additionally, the wick frame 5232 may be moulded as one component, or an assembly of a plurality of moulded components. In some forms, the wick 5230 and the wick frame 5232 may be a single component.

In one form, the wick frame 5232 may further comprise one or more air filters upstream and/or downstream of the wick 5230. The air filter may be placed upstream of the wick 5230 in order to reduce introduction and/or collection of foreign matter onto the wick 5230. Alternatively, or additionally, the air filter may be placed downstream of the wick 5230 in order to reduce incidence of any foreign matter travelling from the wick 5230 to the patient 1000.

According to another aspect, the wick frame 5232 may comprise the air flow baffle 5208 described above. Where the wick frame 5232 is combined with the air flow baffle 5208, the wick 5230 may form one surface of the path of the flow of air. This configuration may be advantageous in that the length of contact is increased between the flow of air and the wick 5230, which may improve humidification.

5.5.2.3.4 Humidifier Filter 5240

One or more humidifier filters 5240 may be used in some arrangements of the humidifier 5000. The humidifier filter 5240 may be used to reduce the amount of undesirable components from the flow of air, for example by preventing the particulates that may have originated from evaporated water from being introduced into the flow of air. A humidifier filter 5240 may be placed anywhere in the humidifier 5000, such as at or near the inlet 5002 (as shown in FIG. 14), the outlet 5004 (as shown in FIG. 16), or therebetween (not shown). It should also be understood that more than one humidifier filter 5240 may be included. A filter (not shown) located downstream of the humidifier 5000, for example in the air circuit 4170, may substantially perform a similar function as a humidifier filter 5240 by reducing the amount of undesirable component from the flow of air.

5.5.2.3.5 Pre-delivery Chamber 5115

According to another aspect of the present technology, the humidifier 5000 may comprise a pre-delivery chamber 5115, an example of which is shown in FIG. 31. The pre-delivery chamber 5115 may receive and retain a volume of water from the reservoir 5110 prior to beginning delivery of water from the pre-delivery chamber 5115 to the water retention mechanism (e.g. humidifier wick 5230), in order to deliver water to the humidifier wick 5230. The pre-delivery chamber 5115 may be fluidly connected to the humidifier wick 5230 at a plurality of locations in order to evenly deliver water to the humidifier wick 5230.

In the example shown in FIG. 31, the pre-delivery chamber 5115 is shaped as a toroid prism, and is configured to receive water from the water feed inlet 5206 and deliver water to the humidifier wick 5230. The pre-delivery chamber 5115 may be configured so that a predetermined amount of water is required in the pre-delivery chamber 5115 prior to any communication of water can occur from the pre-delivery chamber 5115 to the humidifier wick 5230. Thus, in the example shown in FIG. 31, the humidifier wick 5230 may be fluidly coupled to the pre-delivery chamber 5115 by a coupling which may only allow water therethrough after a predetermined amount of water is introduced into the pre-delivery chamber 5115.

In one form, the pre-delivery chamber 5115 may comprise walls made from water impermeable material, which may be flexible, such as Gore-Tex™ fabric or silicone, or rigid such as Polycarbonate/Acrylonitrile Butadiene Styrene (PC/ABS). The pre-delivery chamber 5115 may be fluidly coupled to the humidifier wick 5230 via a plurality of valves (e.g. disposed radially throughout the pre-delivery chamber 5115) configured to open when the quantity of water in the pre-delivery chamber 5115 exceeds a threshold (e.g. predetermined threshold) amount, such as about 90% of the volume of the pre-delivery chamber 5115.

5.5.2.4 Humidifier Transducers

According to one aspect of the present technology, the humidifier 5000 may comprise one or more humidifier transducers configured to generate a signal indicative of the sensed characteristic, such as air flow rate, pressure, temperature or humidity. Thus the humidifier 5000 may comprise one or more flow sensors 5512 (as shown in FIG. 15), one or more temperature sensors (e.g. 5514_1, 5514_2, 5514_3, 5514_4 as shown in FIG. 15), and/or one or more humidity sensors 5516 (as shown in FIG. 16) as well as any number of other types of sensors. The humidifier 5000 may comprise a plurality of sensors located along a direction of the air flow for example, such as temperature sensors 5514_1, 5514_2, 5514_3, 5514_4 as shown in FIG. 15. Additionally, or alternatively, the humidifier 5000 may comprise a plurality of sensors located along a transverse direction to the direction of air flow.

It is noted that although temperature sensors (e.g. 5514_1, 5514_2, 5514_3, 5514_4, 5514_5, 5514_6, 5514_7 and 5514_8) are shown to be located on the interior of the humidification chamber 5200, one or more of the temperature sensors may be located outside the humidification chamber 5200, such as on the outer surface of the outer housing heater cover portion 5202b, or as a part of the heating element 5220, or on the inner housing 5204.

Some humidifier transducers may be located in the humidifier 5000 (e.g. heating element temperature sensor 5514_HE shown in FIG. 16), however humidifier transducers may also be located outside of the humidifier 5000 in some cases, for example in the air circuit 4170, or in the patient interface 3000.

Suitable locations for each of the one or more humidifier transducers may vary according to their purpose and/or algorithms which may use as inputs signals that are generated by each of the one or more humidity sensors 5516. In some cases, transducers configured to generate a signal indicative of a sensed characteristic in one of the pneumatic path, such as the RPT device 4000, may be used to determine the sensed characteristics in another part of the pneumatic path, such as the humidifier 5000.

In some forms, a measurement of a characteristic (e.g. air flow rate, pressure, temperature or humidity) obtained at a first location may be used estimate the equivalent characteristic at a second location. For example, a temperature measurement obtained by a first temperature sensor located on a heating element may be used to estimate a temperature of a water retention feature (e.g. humidifier wick 5230) at another location, as will be described in detail further below in the present specification.

5.5.2.5 Humidifier Controller 5550

In one form, the humidifier 5000 may comprise a humidifier controller 5550, which may be a standalone controller or a part of the central controller 4230 (as shown in FIG. 4C). The humidifier controller 5550 may monitor and/or control one or more operating parameters of the humidifier 5000 based on inputs from components such as other components of the humidifier 5000 and/or the RPT device 4000.

For instance, humidifier 5000 may receive inputs from such components as humidifier transducers, input devices 4220, or memory 4260. Furthermore, the humidifier 5000 may output signals to the heating element 5220 or the water delivery mechanism 5150.

5.5.3 Humidifier Algorithms 5600

Various humidifier algorithms 5600 and their examples (e.g. shown in FIG. 21) are described below. Although they are referred to as 'humidifier algorithms', it is to be understood that these algorithms need not be stored in and/or executed by the humidifier 5000. The term 'humidifier algorithms' is used herein to indicate that the algorithms relate to the humidifier 5000. For example, the humidifier algorithms 5600 may be executed by the central controller 4230 and stored in memory 4260 of the RPT device 4000. In some instances, the algorithms 5600 may be stored and/or executed from an external computer such as a smartphone in communication with the humidifier 5000.

5.5.3.1 Humidifier Condition Determination/Fault Mitigation Algorithms

According to one aspect, the humidifier 5000 may comprise algorithms configured to determine, or detect, one or more conditions of the humidifier 5000 and/or its components. In some cases, the humidifier 5000 may further comprise fault mitigation algorithms configured to ameliorate, or mitigate one or more detected fault conditions.

The humidifier condition determination algorithms may detect or determine conditions of humidifier components such as the reservoir 5110, water delivery mechanism 5150, humidifier wick 5230, heating element 5220 or humidifier transducers. The conditions detected or determined may include: water volume, such as in the reservoir 5110, water flow rate, such as from the water delivery mechanism 5150, or water capacity and/or water content of the humidifier wick 5230.

5.5.3.1.1 Wick Condition Determination Algorithms 5610

As described above, a performance and/or suitability for use of the humidifier wick 5230 may change over time and/or usage, for example due to build-up of foreign matter on the wick 5230 or degradation of the humidifier wick 5230. Accordingly, the water capacity of the humidifier wick 5230 may change, which may affect the amount of humidification which can be provided to the flow of air.

According to another aspect of the present technology, the humidifier 5000 may comprise one or more wick condition determination algorithms 5610 for determining one or more conditions of the humidifier wick 5230. The one or more conditions of the humidifier wick 5230 to be determined may include suitability of the wick for use, water capacity, water content, or remaining usable life of the humidifier wick 5230.

In some forms (e.g. a wick condition determination algorithm 5610A as shown in FIG. 22), a wick condition determination algorithm may receive one or more inputs from step 5610A2 to determine one or more conditions of the humidifier wick 5230 in step 5610A4. The one or more conditions of the humidifier wick may be determined by comparing the inputs to thresholds such as in step 5610A3. In one example, the thresholds may be retrieved from a memory 4260, wherein the thresholds may be stored as a look-up table or a function. The thresholds may be predetermined and stored into memory 4260 by a manufacturer of the humidifier 5000. Additionally, or alternatively, the stored values in the memory 4260 may be updated through a data communication interface 4280, or the thresholds may be retrieved directly through a data communication interface 4280, such as from a remote external device 4286.

The one or more inputs may include wick type data, such as: wick model, date of manufacture, wick material, wick construction, wick dimensions and initial water capacity. The inputs may also include wick usage data, such as: date of last replacement, time of use (e.g. total), quantity of water evaporated using the wick 5230, number of times that the wick 5230 has been washed. The inputs may include any other data which may indicate a condition and/or a property of the wick 5230. Yet further, the wick condition determination algorithms may receive inputs in some cases relating to ambient conditions. A wick condition determination algorithm may then determine one or more conditions of the wick 5230 based on one or more of the above inputs.

Some of the wick conditions may be measured/determined and used as further inputs to other wick conditions. For example, wick conditions such as water capacity and/or the water content of the wick may be determined, and used as inputs to determine other wick conditions such as a remaining usable life of the wick 5230 or to determine whether the wick may be suitable for use, as shown in step 5610A5 of FIG. 22. If the wick 5230 is determined to be no longer suitable for use, the wick condition determination algorithm 5610 may generate a corresponding signal (e.g. in step 5610A6), for example to the humidifier controller 5550 so that the humidifier 5000 may communicate to the user of a need to change the wick 5230, e.g., via a visual and/or an audible communication device.

In one example, a set of input values of: wick model, wick material, wick construction, time of use and number of times that the humidifier wick has been washed may be compared to a set of reference values (e.g. a look-up table) to determine a condition set of the wick, such as a remaining useful life of the wick and/or a water capacity of the wick. The determined condition set (e.g. a remaining useful life of the wick and/or a water capacity of the wick) may then be compared to a threshold (e.g. minimum remaining useful life of the wick or a minimum water capacity of the wick) to generate a signal to indicate whether the humidifier wick 5230 is suitable for use in the humidifier 5000. A visual and/or an audible communication device may be provided to communicate to the user whether the humidifier wick 5230 is suitable for use in the humidifier 5000. As described above, the thresholds may be predetermined and stored into a memory 4260 for example by a manufacturer of the humidifier 5000 based on characterisation of one or more available types of humidifier wick 5230.

In some cases, a calibration algorithm may add to or modify the thresholds, such as to be able to indicate when a wick 5230 has been replaced or washed, for example based on an increase in its water capacity.

A wick condition determination algorithm 5610 may determine and/or express a water capacity of the wick 5230 in absolute terms or relative terms, for example, as shown in an example algorithm 5610B shown in FIG. 23. That is, the water capacity of the wick 5230 may be determined and/or expressed as an absolute quantity of water (e.g. in millilitres) that the wick 5230 is able to hold (as shown in step 5160B3 of FIG. 23) or as a relative (e.g. as a percentage) quantity (as shown in optional step 5160B5 of FIG. 23), such as in relation to a predetermined water capacity of the wick 5230 (as shown in input step 5160B4 of FIG. 23), or in relation to a minimum water capacity of the wick 5230 (not shown). The water capacity of the wick 5230 may be assessed prior to use (such as in step 5610B5) to determine whether the wick 5230 is suitable for use, for example, by comparing the determined water capacity to a threshold water capacity. In some forms, the wick condition determination algorithm 5610 may indicate an unsuitability of the wick (step 5610B7) based on the determined water capacity of the wick 5230.

In one form, a wick condition determination algorithm 5610 may determine a water content of the humidifier wick 5230 as a proportion of its water capacity. The wick condition determination algorithm 5610 may in some forms indicate when a wick saturation condition is reached, which is to say that the full water capacity of the wick 5230 has been met and/or exceeded. A visual and/or an audible communication device may be provided to communicate to the user when a wick saturation condition is reached. In some cases, determination of wick saturation may be used as an input to another humidifier algorithm, for example to stop, or slow down, operation of the water delivery mechanism 5150.

In another aspect, the wick condition determination algorithm may determine a remaining life of the wick 5230 based on the current water capacity of the wick 5230 and the rate of change of the water capacity of the wick 5230 according to one or more previously measured water capacity values of the wick 5230.

In one form (e.g. shown in FIG. 24), a wick condition determination algorithm 5610 may determine a condition of the humidifier wick 5230 based on one or more temperatures (e.g. measured or sensed) at or near the humidifier wick 5230 (in step 5610C2). In some cases, the one or more temperatures may be compared with reference values (in step 5610C3), which may be expected temperatures, temperatures measured from nearby sensors, or previously measured temperatures, to determine the condition of the humidifier wick 5230 (in step 5610C4). The expected temperatures may be based on one or more of operating parameters of the humidifier 5000, such as a heat output from the heating element 5220, a flow rate of air through the humidifier 5000, and a water flow rate through the water feed inlet 5206, as well as any number of others. In some forms, the reference values (e.g. expected temperatures) may be determined from one or more look-up tables or equations based on the one or more operating parameters. The reference values may be expressed as absolute values (e.g. 30 degrees C.) or in relation to measured or sensed values (e.g. plus or minus 10 degrees C.).

According to another aspect, the one or more temperatures may be measured and/or analysed relative to each other, for instance based on any temporal or spatial patterns. In one form, measures of temperature in a humidifier 5000 at various temperature sensors such as 5514_1, 5514_2, 5514_3, 5514_4 (see FIG. 15) may be measured and compared to each other, such as to determine temperature gradients over time and/or space. In another form, measures of temperature in a humidifier 5000 at a temperature sensor such as 5514_1 may be compared against another measure at the same temperature sensor 5514_1 which was taken at another time. For instance, an analysis may compare rates of change of the one or more temperatures against reference values (e.g. of rates of change of temperatures). Alternatively, or additionally, a spatial distribution of temperatures, for example of the one or more temperatures relative to each other, may be compared against reference values.

In one form, one or more of the operating conditions of the humidifier 5000 may be varied while monitoring a response of one or more temperatures to determine a condition of the humidifier 5000. Examples of operating conditions to be varied may include a heat output from the heating element 5220, an air flow rate through the humidifier 5000, and a water flow rate through the water feed inlet 5206 as described above. However, the operating conditions may include any number of other parameters. For example, a first set of temperatures may be measured at a set of temperature sensors, and a second set of temperatures may be measured at the set of temperature sensors while a heat output from the heating element 5220 is increased, to determine an increase of temperature and/or a rate of increase of temperature for the increase in the heat output. Then, a suitability of the humidifier wick may be determined based on the relationship between the increase of temperature and/or the rate of increase of temperature and the increase in the heat output, for example by determining a water capacity of the wick 5230.

One arrangement of the humidifier 5000 comprising temperature sensors 5514_1, 5514_2, 5514_3 and 5514_4 is shown in FIG. 15. In this arrangement, measured temperatures and reference values may be obtained at one or more of the temperature sensors 5514_1, 5514_2, 5514_3 and 5514_4 to determine a condition of the humidifier wick 5230. In one example, a set of temperatures may be measured at one or more of the temperature sensors 5514_1, 5514_2, 5514_3 and 5514_4 and used as a set of input values indicative of a condition of the humidifier wick 5230. Then, a set of reference values may be determined at temperature sensors 5514_1, 5514_2, 5514_3 and 5514_4 for example by measurement or determining an expected set of temperatures.

In one example where an expected set of temperatures is used, measured temperatures at temperature sensors 5514_1, 5514_2, 5514_3 and 5514_4 may be 40° C., 41° C., 40° C. and 52° C. respectively, while the expected temperatures may be 40° C., 40.5° C., 41° C. and 41.5° C., at a particular water flow rate (e.g. 1 g/min) for a particular heat input (e.g. 20 W) to the humidifier wick 5230. In this case, a wick condition determination algorithm 5610 may determine that the water flow rate is sufficiently high so that the wick 5230 should be wet around the temperature sensor 5514_4, and thus determine the humidifier wick 5230 to have a reduced water capacity around the temperature sensor 5514_4.

Another exemplary arrangement of the humidifier 5000 is shown in FIG. 15A. The humidifier 5000 may comprise one or more of a temperature sensor 5514_6 positioned proximal to the water feed inlet 5206, a temperature sensor 5514_7 positioned proximal to the trailing edge of the humidifier wick 5230, and a temperature sensor 5514_8 at an intermediate location between the water feed inlet 5206 and the trailing edge of the humidifier wick 5230.

As water is delivered to the humidifier wick 5230 through the water feed inlet 5206, the area of the humidifier wick 5230 that is proximal to the water feed inlet 5206 is the first area to be wetted by the water delivered to the humidifier wick 5230. Accordingly, a temperature sensor 5514_6 may be located towards the water feed inlet 5206 to generate a signal indicative of water content in the humidifier wick 5230. If the signal generated by the temperature sensor 5514_6 indicates the region proximate to the temperature sensor 5514_6 to be dry, a fault condition may be triggered. For example, such a signal may indicate that the water delivery mechanism 5150 is not operating correctly, or that the humidifier wick 5230 may require replacement.

One or more of the signals generated by the temperature sensors 5514_6, 5514_7, and 5514_8 may indicate a condition of the humidifier wick 5230. In one form, a comparison of temperatures measured by the temperature sensors 5514_6, 5514_7, and 5514_8 may be used to determine a condition of the humidifier wick 5230 in a region around each of the respective temperature sensors.

In another arrangement of the humidifier shown in FIG. 16, a temperature sensor 5514_5 may be placed at or near a periphery of the humidifier wick 5230. For example, the temperature sensor 5514_5 may be placed at a periphery of the humidifier wick 5230 furthest from the water feed inlet 5206 to indicate wick saturation where a wicking rate of the humidifier wick 5230 is isotropic. In an arrangement of the humidifier wick 5230 where the liquid wicking rate is anisotropic, the temperature sensor 5514_5 may be placed at a periphery of the humidifier wick 5230 which may be the last periphery to be reached by the liquid being delivered from the water feed inlet 5206. A region of the humidifier wick 5230 would be expected to exhibit different behaviours between when the region is wet in comparison to when the region is dry. Thus a behaviour at the region of the humidifier wick 5230 may be monitored to determine whether it contains water.

A wick condition determination algorithm (e.g. example algorithm 5610C) may be configured to monitor the temperature at the sensor 5514_5, to determine a flooded condition (in step 561005) for the region of the sensor 5514_5. When the sensor 5514_5 is located at a furthest periphery of the wick 5230 from the water feed inlet 5206, a flooded condition at the sensor 5514_5 may indicate a flooded condition for the entire wick 5230. Thus, for example, if a temperature measured at the sensor 5514_5 is at or below a predetermined threshold, such as 2° C.-5° C. or more below a temperature of the heating element 5220, the wick 5230 may be deemed to be flooded, or saturated, by the wick condition determination algorithm 5610. In one form, the wick condition determination algorithm 5610 may determine a water capacity of the wick 5230 by measuring a time for the wick 5230 to be saturated. Other sensors which may be suitable for use to indicate wick saturation may include an ultrasonic sensor, a noise sensor, a condensation sensor and/or an image processing sensor. In some instances, where the wick is determined to be flooded, the water delivery mechanism 5150 may be stopped (in step 561006), and otherwise the water delivery mechanism 5150 may be continued to operate (in step 561007).

A temperature (e.g. at or near the humidifier wick 5230) may be indirectly determined, without direct measurement. In one form, a measurement taken from a temperature sensor at a first location may be used to determine (e.g. by estimation) a temperature at a second location. For example, a temperature at a first location may be correlated to a temperature at a second location (e.g. by way of a function or a look-up table), in which case measurement of a temperature at the first location may allow estimation of a temperature at the second location (or vice versa). The correlation (e.g. function or look-up table) may be stored in (and retrieved from) a memory 4260, and may be predetermined such as by a manufacturer of the humidifier 5000. In one form, the correlation stored in memory 4260, may be updated for example through a data communication interface 4280.

Thus, a wick condition determination algorithm 5610 may be configured to determine a condition of the humidifier wick 5230 based on one or more temperatures at or near the humidifier wick 5230, wherein the one or more temperatures are indirectly determined.

In another form, the wick condition determination algorithm may determine a remaining life of the wick 5230 based on one or more mechanical properties of a wick 5230. The one or more mechanical properties may include noise/vibration characteristics such as a muffling or an acoustic profile. In other forms, a magnetic and/or optical characteristic of the wick 5230 may be used to determine a remaining life of the wick 5230.

In some forms, a wick condition determination algorithm 5610 may produce one or more outputs to be used by another humidifier algorithm. For instance, the wick condition determination algorithm 5610 may output water capacities of various zones of the wick 5230. Where a humidifier wick 5230 is determined to have a reduced water capacity in one zone, and the heating element 5220 comprises a plurality of heating zones, a heat output by the heating element 5220 to the corresponding heating zones may be varied according to the condition of the humidifier wick.

5.5.3.1.2 Plausibility Check Algorithms 5620

According to another aspect, the humidifier may comprise one or more plausibility check algorithms 5620 configured to test for errors in operation of the humidifier 5000, such as performance of one or more individual components of the humidifier 5000 and/or the entire humidifier 5000.

An example plausibility check algorithm 5620A (shown in FIG. 25) may receive as inputs inlet and/or ambient conditions (step 5620A2), such as measures of a temperature at the air inlet 5002, humidity at the air inlet 5002, ambient temperature, and ambient humidity. The plausibility check algorithm 5620A may further receive as inputs operating parameters (step 5620A3) of the humidifier 5000 such as a heat output of the heating element 5220 to the wick 5230 and a flow rate of water to the wick 5230. The plausibility check algorithm 5620A may determine predicted output conditions (e.g. humidity/temperature at outlet, as shown in step 5620A4) based on the inputs. In one form, the plausibility check algorithm 5620 may monitor outlet conditions (step 5620A5), such as a measured temperature at the air outlet 5004 and a measured humidity at the air outlet 5004. The plausibility check algorithm may compare the measured temperature and/or humidity against the predicted humidity/temperature at the outlet to test plausibility of the measured temperature and/or the humidity. If the temperature at the air outlet 5004 and/or the humidity at the air outlet 5004 is found to be implausible (step 5620A6), for example, as they deviate more than a threshold amount from a predicted value thereof respectively, the plausibility check algorithm may indicate a fault condition. It is noted that in other forms of the plausibility check algorithm 5620, inputs, predicted values and measured values may be varied from the examples provided above. Other examples of suitable output conditions to be monitored may include a temperature of the humidifier 5000, such as a temperature at or near the humidifier wick 5230. For example (not shown), the inlet/ambient conditions and outlet conditions may be monitored to determine predicted operating parameters, and to compare the predicted operating parameters with measured operating parameters in order to determine plausibility of the measurements.

For instance, at an absolute ambient humidity of 10 milligrams per litre (mg/L), at an air flow rate of 35 L/min, a predicted absolute humidity of the flow of air at the air outlet 5004 may be 30 mg/L. Accordingly, if the water delivery mechanism 5150 has been delivering a water flow rate of 700 mg/min, evaporation of the delivered water would add (700 mg/min)/(35 L/min)=20 mg/L of absolute humidity to the flow of air at the air outlet 5004. However, after a threshold period of time, for example 5 minutes, the absolute humidity at the air outlet 5004 is below a threshold amount of the target absolute humidity, the plausibility check algorithm may determine that the humidifier 5000 is not operating correctly and indicate a fault condition.

In another form, a plausibility check algorithm 5620 may perform a test cycle to check operation of the humidifier 5000. For instance, the plausibility check algorithm 5620 may change the heat output of the heating element 5220 and/or the water flow rate of the water delivery mechanism 5150 and check a response of the humidifier 5000 using one or more of the humidifier transducers.

In another form, a plausibility check algorithm 5620 may check for correct performance of a component such as a water delivery mechanism 5150, by comparing a water flow rate in comparison to a rate of movement of the water pump 5152.

The plausibility check algorithms 5620 may be configured to run at one or more of predetermined intervals, predetermined triggers or user/patient requests. For example, the plausibility check algorithm 5620 may be performed at start-up of the humidifier 5000, at monthly intervals, at requests of the patient 1000, at requests from a remote location such as a health care provider's computer, or when the humidity sensor 5516 detects that the output humidity from the humidifier 5000 is below a target for a threshold period of time. In other cases, the plausibility check algorithms 5620 may be configured to be running continuously (or periodically) while the humidifier 5000 is in operation.

5.5.3.1.3 Pump Condition Determination Algorithms 5630

In one form, the humidifier 5000 may comprise one or more pump condition determination algorithms 5630. The pump condition determination algorithm may determine, for example, any blockages in the pump 5152 or any fault conditions of the pump 5152 such as an over-temperature condition, an over-current condition or leak. In one form, pump condition determination algorithm(s) may be performed at humidifier start-up (e.g. prior to commencement of therapy and/or humidification) to determine the suitability of the pump 5152 for operation.

In one example, the pump condition determination algorithm 5630 may monitor power consumed by the pump 5152, such as by monitoring current consumed by the pump 5152, and indicate a fault condition if the power consumed by the pump 5152 is outside of a threshold, such as a threshold range. In another example, the pump condition determination algorithm 5630 may monitor a temperature of the pump 5152, and indicate a fault condition if the temperature of the pump 5152 is outside of a threshold, such as a threshold range.

5.5.3.1.4 Fault Mitigation Algorithms

One aspect of the present technology relates to use of fault mitigation algorithms.

In one form, a fault mitigation algorithm may be configured to respond to outputs of wick condition determination algorithm 5610 and/or the plausibility check algorithms 5620. For instance, the wick condition determination algorithm 5610 may determine a condition of the humidifier wick 5230 and output a signal indicating that the humidifier wick 5230 may no longer be suitable for use. Then, the fault mitigation algorithm may act to reduce a flow rate of air through the humidifier 5000, reduce a water flow rate from the water delivery mechanism 5150, and/or possibly stop operation of the humidifier 5000 and/or the RPT device 4000.

A fault mitigation algorithm may be additionally, or alternatively, configured to respond to detection of over-temperature and/or over-current in one or more electrical components of the humidifier 5000. For example, the fault mitigation algorithm may receive a signal from a pump condition determination algorithm 5630 that the pump is malfunctioning, and shut down operation of the humidifier 5000.

In another form, a fault mitigation algorithm may look for a condition where 'negative leak' is detected. Negative leak condition occurs when the flow rate of air through the pressure device 4140 is less than the estimated flow rate through the vent 3400 that was determined assuming normal operating conditions. Occurrence of such a condition may indicate that the flow rate through the vent 3400 has been reduced, for example because the vent 3400 has been at least partially occluded. One potential cause of the blocking may be due to accumulation of condensation on or near the vent 3400, and accordingly the fault mitigation algorithm may reduce a level of humidification output in order to try to reduce the occlusion.

5.5.3.2 Humidifier Control Algorithms 5.5.3.2.1 Humidification Algorithms 5650

According to one aspect, humidification algorithms 5650 may be configured to control components of the humidifier 5000 to manage the humidity of the flow of air delivered from the humidifier 5000.

In one form, the humidification algorithm 5650 may receive as inputs one or more target output conditions such as target output humidity or target output temperature, one or more ambient conditions such as ambient humidity or ambient temperature, and/or one or more measured output conditions such as measured output humidity or measured output temperature. Other possible inputs for the humidification algorithm 5650 may include characteristics of an air circuit 4170 such as its length, or characteristics of the patient interface 3000 such as its type, or vent characteristics. In some cases, characteristics of the air circuit 4170 and/or the patient interface 3000 may be input by a user, however in other cases, they may be detected by an identification module or a recognition system, such as that described in PCT Application Publication No. WO 2010/091462, the entire contents of which is hereby incorporated by reference. The humidification algorithms 5650 may further use as inputs one or more of a presence of a patient 1000, a flow rate of the flow of air through the air circuit 4170, a pressure gradient of the flow of air, or a breath rate of a patient 1000.

The humidification algorithms 5650 may in one form operate so that the flow of air delivered by the humidifier 5000 is at or close to 100% relative humidity, although other relative humidifies may be possible, such as (but not limited to) 40%, 50% 60%, 70%, 80% or 90%. One advantage of the present technology may include a shortened response time as described above. In some forms, the humidification algorithms 5650 may have a target set as an absolute humidity, while in others the target may be set as a relative humidity. The humidification algorithm 5650 may thus be configured in some forms to operate to humidify the air flow until a 90%-100% output relative humidity is detected, at which point the humidification algorithm 5650 may reduce, or cease, adding humidity (humidity output) by the humidifier 5000. Advantageously, a shortened response time of the present technology may allow the humidifier 5000 to operate in this fashion without producing significant, or any, condensation, whereas a humidifier 5000 with a longer response time may not be able to reduce the humidity output in the time required. Additionally, or alternatively, a humidification algorithm 5650 may reduce (or prevent) occurrence of condensation by increasing a heat output of the air circuit heating element 4171 when occurrence of condensation is detected (e.g., by an optical sensor or other sensor, or methods described elsewhere in this document). Thus, in one example, where occurrence of condensation is detected, a humidification algorithm 5650 may reduce a humidity output of the humidifier 5000 to reduce the absolute humidity of air flow being delivered, while the air circuit heating element 4171 increases its heat output into the air circuit 4170 to ameliorate formation of further condensates and vaporise existing condensates.

Thus, in one form, the humidifier 5000 may be configured to maintain or increase a humidity output until condensation is detected, for example in the air circuit 4170, the patient interface 3000 or in the patient's airways. Upon detection of condensates, the humidifier may decrease the humidity output until the condensates can be said to have evaporated, or have been removed, and no further condensates occur. Using such a method, the humidifier 5000 may deliver a humidity as close to 100% as possible without producing significant condensations, thereby minimising disturbances to the patient while improving the patient's quality of therapy and/or comfort.

In one form, a humidification algorithm 5650 may receive as an input an output from a condensation detection algorithm 5700, which is described in further detail below. The humidification algorithm 5650 may be configured to reduce a humidity output of the humidifier 5000 where the condensation detection algorithm 5700 indicates an occurrence of condensation. Such an arrangement may be advantageous where condensation has occurred within an air circuit 4170 away from a humidity sensor 5516, in which case the humidity sensor 5516 may indicate a humidity of less than 100% even though it may be 100% at the location of condensation.

In another form, an output indicating an occurrence of condensation from the condensation detection algorithm 5700 may be used to predict (and/or prevent) condensation to occur at a later time. For example, if condensation was detected at a particular time, the humidification algorithm 5650 may record one or more variables such as: ambient conditions (temperature/humidity/pressure), respiratory treatment parameters (e.g. pressure, flow rate), and humidifier/air circuit operating conditions (e.g. heating element 5220 output, measured humidity or measured temperature). The humidification algorithm 5650 may then flag or learn the set of recorded variables to indicate a condensation onset condition, and predict an occurrence of condensation if a set of variables at a later time approaches the condensation onset condition. The humidification algorithm 5650 may then, for example, alert the user (e.g. patient 1000), or modify an operation of the humidifier 5000 to avoid arriving at the condensation onset condition by, for example, reducing a water flow rate from the reservoir 5110 to the humidification chamber 5200.

According to another aspect, a humidification algorithm may be programmed to behave in a non-linear fashion as a response to a change in operating conditions. For instance, the humidification algorithm may be programmed so that when a mask leak increases, e.g. from 5 L/min to 10 L/min, increasing the total flow rate from 35 L/min to 40 L/min, the heat output from the heating element 5220 and the water flow rate from the water delivery mechanism 5150 is increased by a greater amount than 5/35. In another example, the humidification algorithm may be configured to increase the absolute humidity of the air flow when a flow rate is increased. Such an arrangement may counteract any decreases in patient comfort, for example due to increased leak and dryness. The response by a humidification algorithm based on a change in operating conditions may be delayed in some cases.

In another aspect, the humidification algorithm 5650 may be configured to determine suitable target conditions according to the ambient conditions, for example without the need for a user (or a patient 1000) to change the desired output condition. For instance, the humidification algorithm 5650 may direct the humidifier 5000 to output warmer air at a higher humidity where the ambient conditions are colder and drier in comparison to where the ambient conditions are warmer and more humid.

In some forms of the humidification algorithm 5650, the heat output to the humidifier wick 5230 and the water flow rate to the humidifier wick 5230 may be controlled as a function of each other. For instance, where the heat output to the humidifier wick 5230 is limited, such as due to low power availability, the water flow rate to the humidifier wick 5230 may be reduced accordingly. Furthermore, where the water flow rate is reduced such as where the quantity of water in the reservoir 5110 is limited, the heat output to the humidifier wick 5230 may be reduced accordingly.

In a yet further aspect, the humidification algorithm 5650 may determine target conditions according to one or more preferences and/or therapeutic requirements of the patient 1000. In one form, the humidification algorithm 5650 may receive a set of patient preferences through input devices 4220. In another form, the humidification algorithm 5650 may learn a patient's preference from a usage pattern of the patient 1000 or detection of sleep quality of a patient 1000.

In one example, a breath phase of the patient may be used as an input to the humidification algorithm 5650. For example, the humidification algorithm 5650 may cause the humidifier 5000 to add more humidity to the air flow for inspiration than expiration. Alternatively or additionally, the portion of the flow of air to be delivered to the patient during inspiration may be of a higher temperature, for example by increasing an amount of heat delivered to the heating element 5220, or increasing the amount of water delivered to the humidifier wick 5230.

The humidifier 5000 may be arranged relative to the patient 1000 such that a portion of the flow of air will take a length of time to travel from the humidifier 5000 to the entrance of the patient's airways, wherein the length of time is significant in comparison to a length of a breath of a patient. The length of time may be referred to as a humidification lag, and where the humidification lag is significant, it may need to be considered in order to effectively deliver an air flow according to a patient's breath phase.

In one form, the time lag may be determined from a manual input by a user, for example by identifying one or more of a type and length of one or more of the air circuit, the humidifier, the blower and the patient interface. A controller, such as a central controller 4230, may then determine the time lag, for example by estimating the total length for the air flow to travel between the humidifier 5000 and the patient 1000, and dividing by a speed of air. Then, the humidification algorithm 5650 may be configured to output an air flow from the humidifier 5000 for a patient breath phase in advance of the patient breath phase by the amount of the time lag ($t_{lag}$). Thus, if the patient 1000 is expected to begin inhalation at time t, the humidification algorithm 5650 may be configured to deliver the portion of air flow for inhalation to leave the humidifier 5000 at time $t-t_{lag}$.

In another example, a property of an air flow path through the patient 1000 may be used as an input to the humidification algorithm 5650. For instance, a patient 1000 may change the orifices that they breathe through according to a sleep state, such that while they are in bed falling asleep, they may breathe primarily through their mouth, whereas they may primarily breathe through their nose once they are asleep. In other patients, the converse may apply, or some combination of mouth and nose breathing may apply, while breathing differently according to a sleep state.

An air flow which is exhaled through the mouth of the patient 1000 may be cooler than an air flow which is exhaled through the nose of the patient 1000 due to the changed air flow paths. Accordingly, it may be desirable to provide additional amounts of heat and moisture to the patient 1000 where the air flow path is more directed through the mouth of the patient than the nose of the patient. In one form, a sleep state of the patient 1000 may be determined, and the humidification algorithm 5650 may automatically adjust a humidification setting according to the patient's sleep state. In another form, a degree of mouth breathing may be determined, and the humidification algorithm 5650 may automatically adjust a humidification accordingly.

In other forms, a patient's sleep state may be determined and used as an input to the humidification algorithm 5650. For example, where the patient is more likely to experience arousal, such as during rapid eye moment (REM) sleep, the humidification level may be increased for improved comfort. This may for example be balanced against other stages of sleep where arousal is not as likely, during which time the humidification algorithm 5650 may then reduce the humidification level to increase the length of time over which humidification may be provided and/or an interval between the length of time for the reservoir 5110 to be re-filled.

According to another aspect, the humidification algorithm 5650 may be configured to provide a period of higher humidity than the humidity provided during the rest of the therapy session. For example, the period of higher humidity may provide an output humidity of 95% humidity to the patient for an hour while nominally a humidity output of 80% is provided for the remaining hours (e.g. 7 hours) of patient's therapy (e.g. during a night's sleep).

The period of higher of humidity may be triggered based on one or more factors, such as mask leak, mouth leak, at humidifier start-up, towards an end of the therapy session, a physiological state (e.g. disease state, allergies, fatigue level) of the patient or an environmental factor (e.g. pollen count).

5.5.3.2.2 Humidifier Calibration Algorithms 5660

In some cases, one or more humidifier calibration algorithms 5660 may be used to verify operation of the humidifier 5000 and/or to calibrate the humidifier 5000. One or more humidifier calibration algorithms may be performed periodically, or according to triggers such as user requests. For instance, an out-of-calibration operation of the humidifier 5000 may lead to an oversupply of water in comparison to the desired water flow rate, which may lead to introduction of water in the air circuit 4170. Alternatively, an undersupply of water in comparison to the desired water flow rate may lead to overheating of the humidifier 5000 or discomfort for the patient 1000.

In one form, a humidifier calibration algorithm 5660 may deliver a known water flow rate to a humidifier wick 5230, while varying a heat output to the wick 5230 to analyse one or more responses of the humidifier 5000, for example, using the humidifier transducers.

In another form, a humidifier calibration algorithm 5660 may deliver a known heat output to a humidifier wick 5230, while varying a water flow rate to the wick 5230 to analyse one or more responses of the humidifier 5000, for example, using the humidifier transducers.

5.5.3.2.3 Humidifier Start-up Algorithms 5665

In some forms, one or more humidifier start-up algorithms 5665 may be used to control one or more aspects of the humidifier 5000 in its start-up phase of operation, for example, within the first 5, 10, 30, or 60 minutes after the humidifier 5000 is switched on or after the humidifier 5000 begins to humidify the air flow.

According to one aspect, a humidifier start-up algorithm 5665 may be configured to initiate operation of a first component prior to a second component during the start-up phase, while both the first and the second components may simultaneously operate subsequent to the start-up phase. In one form, the humidifier start-up algorithm 5665 may initiate operation of the water delivery mechanism 5150 prior to initiating operation of the heating element 5220 to prevent overheating.

In one example, the humidifier start-up algorithm 5665 may be configured to delay supply of power to the heating element 5220 until the water delivery mechanism 5150 has delivered at least a predetermined amount of water to the humidifier wick 5230, which may be measured in relative terms (such as 20%, 40%, 60%, 80% of wick saturation) or in absolute terms (such as 2.5 g, 5 g, 10 g, or 15 g of water). In another form, the humidifier start-up algorithm 5665 may be configured to delay supply of power to the heating element 5220 by a predetermined length of time, such as 15 seconds, 30 seconds, 1 minute, or 2 minutes to allow for the humidifier wick 5230 to receive a volume of water from the water delivery mechanism 5150. In yet other forms, the water delivery mechanism 5150 and the heating element 5220 may simultaneously be initiated, however, the power supplied to the heating element 5220 may be reduced during the start-up phase.

According to another aspect, a humidifier start-up algorithm 5665 may be configured to provide an increased humidity output during the start-up phase. In one form, the humidifier start-up algorithm 5665 may be configured to provide more power to the heating element 5220 and/or higher water flow rate through the water delivery mechanism 5150 than the power and/or water flow rate used throughout a subsequent time period.

For example, the humidifier start-up algorithm 5665 may be configured so that the power output by the heating element 5220 may be higher during the start-up phase than a subsequent time period or phase. For example, the power output by the heating element 5220 may be approximately 20%, approximately 40%, approximately 60%, or approximately 80% higher than a power output by the heating element 5220 in its normal operation.

Alternatively, or additionally, the water flow rate from the water reservoir 5110 to the humidifier chamber 5200, such as by the water delivery mechanism 5150, may be increased together with, or independently of, the power provided to the heating element 5220.

Thus, the humidity and/or heat output by the humidifier 5000 may be higher at a start-up phase in comparison to the subsequent time period or phase. Accordingly, the air flow delivered to the patient may be conditioned to the desired humidity/or temperature at a faster speed than if the humidity and/or heat output by the humidifier 5000 had stayed constant. Alternatively, or additionally, in some cases, the air flow delivered to the patient may be at an increased humidity and/or temperature during the start-up phase, which the patient may find more desirable, before settling to a decreased level of humidity and/or temperature during a subsequent time period or phase.

5.5.3.2.4 Foreign Matter Management Algorithms 5670

As described above, formation, collection, and/or build-up on foreign matter such as particulates may occur on the humidifier wick 5230, which may adversely affect a performance of the wick 5230. According to one aspect, one or more foreign matter management algorithms may be used to control the location and/or rate of foreign matter build-up on the wick 5230.

In some cases, foreign matter may collect on the humidifier wick at the greatest rate where the wick 5230 dries out completely. For instance, at a water boundary 5230_WB of the water retained by the wick 5230, as shown in FIG. 14. In one form, a foreign matter management algorithm 5670 may manage a location and/or pattern of a water boundary 5230_WB, for example, away from an area of detected low water capacity. The foreign matter management algorithm 5670 may achieve this goal by controlling one or more of the heat output onto the humidifier wick 5230, a water flow rate onto the humidifier wick 5230 or a water distribution pattern within the humidifier wick 5230.

According to another aspect, a foreign matter management algorithm may be configured to determine a quality of water, such as a foreign matter content in the water. In one form, a conductivity of water may be measured to determine the foreign matter content in the water. In one form, electrodes in contact with the water may be placed in the humidifier 5000 (e.g. in the reservoir 5110, water delivery mechanism 5150, or in the wick 5230) to measure resistivity of the water. In some forms, the electrodes may be placed in the wick 5230 so that the resistivity measured will indicate resistivity of the wick and the water therein, where a high resistivity may indicate a corresponding high level of foreign matter build-up in the wick.

The foreign matter management algorithm may be configured to vary a location of the water boundary 5230_WB during use of the humidifier 5000. Particulates or foreign matter may collect at a faster rate at the location of the water boundary 5230_WB than the rest of the humidifier wick 5230. Thus, during use of the humidifier 5000, by varying a location of the water boundary 5230_WB, a distribution of the foreign matter that is collected throughout the humidifier wick 5230 may be controlled, for example to extend a useful life of the humidifier wick 5230.

The foreign matter management algorithm may vary a location of the water boundary 5230_WB by adjusting one or both of the water flow rate to the humidifier wick 5230 and a heat output of the heating element 5220.

In one form, a water flow rate of the humidifier 5000 may be varied between a minimum water flow rate and a maximum water flow rate. The water flow rate may vary between the minimum water flow rate and the maximum water flow rate, such as linearly or as a sinusoid for example.

Figure 14A:
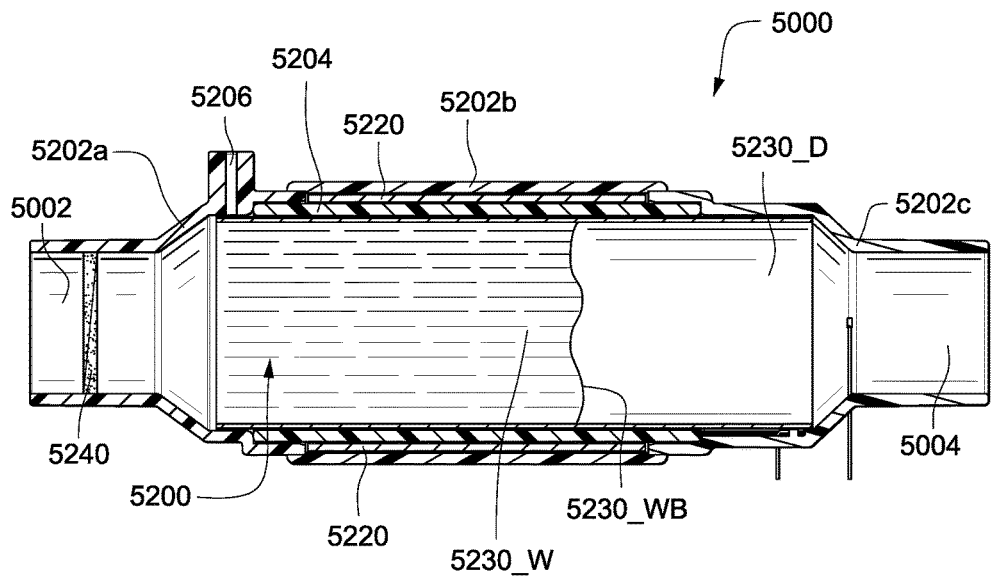
Figure 14B:
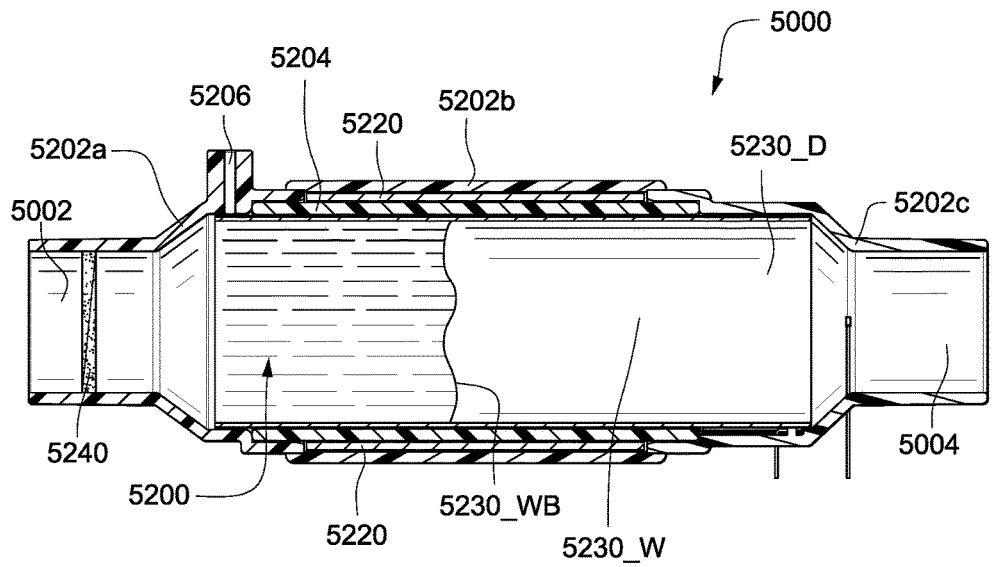

A location of the water boundary 5230_WB may be varied during use of a humidifier 5000, such as shown in FIGS. 14, 14A and 14B. The location of the water boundary 5230_WB may be varied in a reciprocating motion, such that the water boundary 5230_WB moves from a first location shown in FIG. 14, to a second location shown in 14A, to a third location shown in 14B, back to the second location shown in 14A, and so on.

Alternatively, or additionally, a heat output of the heating element 5220 may be varied between a minimum heat output and a maximum heat output. The heat output may vary between the minimum heat output and the maximum heat output, such as linearly or as a sinusoid for example.

It will be understood by the skilled person that a number of other means may also be used to vary a location of the water boundary 5230_WB. It will be also understood that the variation of a location of the water boundary 5230_WB may follow a different regime, such as at a non-linear rate.

In some forms, variation of the location of the water boundary 5230_WB may be periodic, to encourage a build-up of particulates to occur according to an even distribution through a length of the humidifier wick 5230.

In some forms, the foreign matter management algorithm may be configured such that a location of the water boundary 5230_WB may be at least partly determined by a determined condition of the humidifier wick 5230. For example, a first region of the humidifier wick 5230 may be found to include a higher concentration of foreign matter or particulates than a second region of the humidifier wick 5230. In response, the foreign matter management algorithm may operate to move the water boundary 5230_WB towards, or into the second region for longer periods of time than in the first region.

5.5.3.2.5 Wick Drying Algorithms 5675

The humidifier 5000 may comprise one or more wick drying algorithms 5675 configured to reduce a water content of a humidifier wick 5230. A wick drying algorithm 5675 may operate to dry the humidifier wick 5230, such as at completion of a therapy session, or when the humidifier wick 5230 is determined to be saturated with water.

A wick drying algorithm 5675 may reduce a water content of the humidifier wick 5230 by one or more of: preventing a flow of liquid from the reservoir 5110 to the humidifier wick 5230, reducing a flow of liquid from the reservoir 5110 to the humidifier wick 5230, increasing a heat output of the heating element 5220, increasing a flow rate of air through the humidifier 5000, and increasing a temperature of the air through the humidifier 5000.

5.5.3.2.6 Wick Cleaning Algorithms 5680

The humidifier 5000 may comprise one or more wick cleaning algorithms 5680 configured to clean the humidifier wick 5230, for reducing the amount of foreign matter and/or any bio-burden on the wick 5230.

In one form, a wick cleaning algorithm 5680 may operate to rinse the humidifier wick 5230 with a supply of water and/or a cleaning agent. Additionally, or alternatively, the wick cleaning algorithm 5680 may dry the wick 5230, in some cases at a temperature higher than an operating temperature.

In another form, a wick cleaning algorithm 5680 may be configured to activate where a cleaning adapter is coupled to the humidifier 5000. One advantage of this form may be to prevent use of the humidifier 5000 by the patient 1000 while the wick cleaning algorithm 5680 is activated. In some cases, the cleaning adapter may comprise a cleaning agent which may be released into the humidifier wick 5230 while the wick cleaning algorithm 5680 is active.

A wick cleaning algorithm 5680 may be configured to operate in some forms after cessation of therapy. In some cases, the RPT device 4000 and/or a humidifier 5000 may be arranged with a battery to enable operation of the wick cleaning algorithm 5680 after power has been switched off.

5.5.3.3 Patient Feedback Algorithms 5690

The humidifier 5000 may comprise one or more patient feedback algorithms 5690 for relaying information and/or providing recommendations to the patient 1000.

Patient feedback algorithms 5690 may, in some forms, inform the patient 1000 of one or more outputs from the humidifier algorithms described above. Examples of information provided to a patient 1000 by a patient feedback algorithm 5690 may include a condition of the humidifier wick 5230, such as its remaining life or a quality of the water, or any anomalous activity of the humidifier 5000, or an indication of a fault, such as detection of a missing reservoir 5110. In some cases, a patient feedback algorithm 5690 may simply indicate to a patient 1000 or a caregiver that the humidifier wick 5230 may require washing.

In one form, a patient feedback algorithm 5690 may collect data relating a patient's sleep data to one or more humidification conditions. The patient feedback algorithm 5690 may then correlate the measured data to determine one or more preferred humidification conditions. For example, the patient feedback algorithm 5690 may collect patient sleep data relating to one or more of: arousal event data, sleep state data and any SDB event data. The patient feedback algorithm 5690 may also collect one or more humidification conditions such as ambient conditions (e.g. ambient temperature, pressure, humidity) and/or output conditions (output temperature, humidity), and correlate the patient sleep data to humidification conditions to determine the patient's preferred output temperature and/or humidity based on ambient conditions.

A patient feedback algorithm 5690 may also include as inputs one or more of: therapy conditions (e.g. total flow rate, leak flow rate, therapy pressure), sleep disordered breathing events (e.g. apneas, hypopneas, arousals, flow limitations), calendar data (e.g. distinguish between weekday/weekend, first scheduled meeting of the day, alarm clock setting), and a sleep state monitor to determine the output temperature and/or humidity to be delivered to the patient by correlating the inputs to a preferred humidification condition.

5.5.3.4 Condensation Related Algorithms

5.5.3.4.1 Condensation Detection Algorithms 5700

Occurrence of condensation in a respiratory treatment system may be undesirable as condensation may adversely affect operation of one or more components. For example, condensates may short circuit an electrical connection, or occlude a pneumatic path such as a vent 3400 or a port of a transducer such as a flow sensor 4274 or a pressure sensor 4272. Condensation, when it occurs in significant quantities, may also affect the patient 1000 in that ingress of condensation into the patient's airways during sleep may cause disturbances such as arousal, or worse, potentially present a hazard. Thus, the humidifier 5000 may comprise one or more algorithms to determine whether condensation may have occurred in the respiratory treatment system.

According to a first example, a condensation detection algorithm 5700 may be configured to compare properties of the air flow at a first location and a second location to determine whether any condensation may have occurred therebetween.

In one form (see FIG. 26), a respiratory treatment system (e.g. in the humidifier 5000 or the air circuit 4170) may comprise a first humidity sensor 5516_1 (e.g. at or near an inlet of an air circuit 4170), and a second humidity sensor 5516_2 downstream of the first humidity sensor (e.g. at or near an outlet of the air circuit 4170). Occurrence of condensation in the air circuit 4170 may cause a decrease in absolute humidity from the inlet to the outlet of the air circuit, as moisture is removed from the air flow (where it is in a form of water vapour) as liquid water. Thus, a condensation detection algorithm 5700 may be configured to indicate an occurrence of condensation in the air circuit upon detection of a decrease in absolute humidity from the first humidity sensor 5516_1 to second humidity sensor 5516_2. In some forms, where the humidity sensor is configured to measure a relative humidity, the respiratory treatment system may comprise additional sensors, such as a temperature sensor to help determine an absolute humidity.

For instance, air at the first humidity sensor 5516_1 may be determined to have a relative humidity of 86% at a temperature of 30 degrees, and a relative humidity of 92% at a temperature of 27 degrees at the second humidity sensor. The corresponding absolute humidity at the first humidity sensor 5516_1 would be 23.2 g/kg, and 20.9 g/kg at the second humidity sensor 5516_2. At an air flow rate of 30 litres per minute, the condensates would be produced between the first humidity sensor 5516_1 to second humidity sensor 5516_2 at a rate of approximately 0.09 g/min, or 5.4 g/hour. Thus the condensation detection algorithm 5700 may indicate an occurrence of condensation, which may then be used to prevent occurrence of further condensation and prevent accumulation of condensates.

In another example, a measured thermal response may be compared to a predicted thermal response to indicate an occurrence of condensation, where the predicted thermal response is based on an assumption of lack of condensation. Where condensation has occurred within an air circuit 4170, a thermal response of the air flow in the air circuit 4170 may be altered due to an increased heat capacity of the contents of the air circuit 4170. For example, saturated air at a temperature of 25° C. has a density of 1.166 kg/m3, with a heat capacity of 1.043 kJ/kgK. At an air flow rate of 30 litres per minute (0.5 litres per second), the total heat capacity of the air flow (per second) would be 0.61 kJ/K. The heat capacity of the contents of the air circuit 4170 would then be approximately doubled should liquid water of 0.15 g mass be present in the tube. Accordingly, when heat is input to the air circuit 4170, presence of condensation may reduce a heating response of the air flow therein in comparison to a heating response where the prediction assumed that condensates are not present in the air circuit 4170, thereby changing a measured thermal response from the predicted thermal response.

Thus, in one form, a condensation detection algorithm 5700 may detect occurrence of condensation by comparing a measure of rate of heat energy input to the air circuit 4170, and a measure of heating response, such as heating rate per time or heating rate per distance. Referring to FIG. 27, for example, a respiratory treatment system may comprise a first temperature sensor 5514_6 (e.g. located at an inlet of the air circuit 4170) and a second temperature sensor 5514_7 located downstream of the first temperature sensor 5514_6 (e.g. at an outlet of the air circuit 4170). Where the air circuit 4170 comprises a heating element 4171, the heat energy input into the air circuit 4170 (and thus to the air flow travelling therethough) may be correlated to measurements at one or more of the first temperature sensor 5514_6 and the second temperature sensor 5514_7.

In some forms, the condensation detection algorithm 5700 may also use as inputs one or more of: a pressure or flow rate of the air flow travelling through the air circuit 4170, ambient conditions (e.g. temperature/humidity/pressure), or a rate of heat transfer between the air circuit 4170 and the ambient. The flow rate may be determined by a flow sensor 4274 or an estimation method (e.g. as described in U.S. Pat. No. 5,740,795, the entire content of which is incorporated herewithin by reference).

Based on the above inputs, the condensation detection algorithm 5700 may determine a predicted thermal response, to compare against a measured thermal response, such as a temperature difference between two temperature sensors (e.g. the first temperature sensor 5514_6 and the second temperature sensor 5514_7), or a rate of change of temperature at a temperature sensor (e.g. second temperature sensor 5514_7). In some forms, a predicted thermal response may be based on one or more previous measurements of thermal response.

In another form, a predicted thermal response may be based on a look-up table or a model which is based on an assumption wherein condensates are not present.

In one form, the condensation detection algorithm 5700 may be configured to indicate an occurrence of condensation where the measured thermal response deviates from the predicted thermal response by more than a threshold. For example, when the predicted temperature difference is greater than the measured temperature difference by a threshold, such as a predetermined percentage or a predetermined temperature. In another form, the condensation detection algorithm 5700 may be configured to indicate an occurrence of condensation where a predicted rate of change of temperature (e.g. at the second temperature sensor 5514_7) is greater than a measured rate of change of temperature, such as a predetermined percentage or a predetermined magnitude.

In another example, a condensation detection algorithm 5700 may determine an occurrence of condensation by establishing a steady state baseline condition, and searching for a deviation from the baseline condition which may be caused by condensates.

In one form, the air circuit 4170 as shown in FIG. 27 may be operating in a steady state such that temperatures measured at the second temperature sensor 5514_7 has been consistent for a period of time, which may be a predetermined period of time (e.g. 30 seconds, 1 minute, 5 minutes, 10 minutes). In such a case, in the absence of other significant deviations in relevant variables, the condensation detection algorithm 5700 may indicate an occurrence of condensation where the temperatures measured at the second temperature sensor 5514_7 begin to decrease, which may be caused by an increase in heat capacity of the contents of the air circuit 4170.

It will be understood by those skilled in the art that aspects of any of the above examples may be combined to derive other methods of detecting an occurrence of condensation.

5.5.3.4.2 Condensation Calibration Algorithms 5710

According to one aspect, the humidifier 5000 may comprise a condensation calibration algorithm 5710 configured to establish one or more variables indicating a condition at which condensation may occur. A set of such variables may be referred to as a condensation onset condition. For example, a condensation calibration algorithm 5710 may monitor all or some of: ambient pressure, ambient temperature, therapy pressure, air flow rate and air flow temperature, heat input by the humidifier heating element 5220, and heat input by the air circuit heating element 4171.

The humidification algorithm 5650 may use the established condensation onset condition to operate the humidifier 5000 at or near saturation humidity. As the condensation onset condition may comprise multiple variables, in some forms, the condensation calibration algorithm 5710 may record a plurality of condensation onset conditions, any of which may result in the air circuit 4170 experiencing an occurrence of condensation. In one form, the condensation calibration algorithm 5710 may be configured to operate periodically (e.g. every 10 minutes, 30 minutes, 1 hours) to update the condensation onset condition(s).

In one form, a condensation calibration algorithm 5710 may operate an air circuit heating element 4171 at a plurality of power output conditions, and monitor the thermal response. For example, the condensation calibration algorithm 5710 may operate the air circuit heating element 4171 at one or more power outputs, for example at 30 W, 25 W, 20 W, 15 W, 10 W and 5 W, and monitor a temperature gradient within the air circuit 4170, for example by monitoring a rate of heating between two temperature sensors (e.g. first temperature sensor 5514_6 and second temperature sensor 5514_7 as shown in FIG. 27). The resulting rate of heating (e.g. difference in temperature between the two temperature sensors 5514_6 and 5514_7), may be correlated with the power output of the heating element 4171, to determine a condensation onset condition, for example, as shown in FIG. 29, where a condensation onset condition is found as an inflection point 5712. The conditions below the inflection point may be referred to as a condensation condition 5716, and conditions above the inflection point may be referred to as a non-condensation condition 5714.

According to one aspect, where the air circuit 4170 may comprise a plurality of zones (as described above), a condensation calibration algorithm 5710 may use one of the plurality of zones to determine a saturation condition. For example, as shown in FIG. 28, the air circuit 4170 may comprise a first zone 4170_1 located distal to the patient and a second zone 4170_2 located proximal to the patient. The first zone 4170_1 may be operated at a first set of parameters (e.g. at a first rate of heat input from a first heating element 4171_1) to produce condensation therein, in order find a set of condensation onset conditions as described above. At the same time, the second zone 4170_2 may be operated at a second set of parameters (e.g. at a second, higher rate of heat input from a second heating element 4171_2) to prevent occurrence of condensation in portions of the air circuit 4170 which may be proximal to the patient (e.g. in the second zone 4170_2).

According to one aspect, the condensation calibration algorithm 5710 may be configured to search for one or more condensation onset conditions independently of an output from a condensation detection algorithm 5700. In one form, the condensation calibration algorithm 5710 may achieve this goal by changing a variable until a condensation onset condition was detected, such that for example condensation had ceased to occur, or condensation had begun to occur.

For example, as shown in FIG. 30A and FIG. 30B, the condensation calibration algorithm 5710 may vary the heating power supplied (e.g. by the heating element 4171) to the air circuit 4170 to find condensation onset conditions. In FIG. 30A, starting from a condensation condition, the condensation calibration algorithm 5710 may increase the heating power supplied until a condensation detection algorithm 5700 detects a cessation of condensation at, for example 5711, which may be marked as a condensation onset condition. Also, starting from a condensation condition, the condensation calibration algorithm 5710 may decrease the heating power supplied until the condensation detection algorithm 5700 detects that condensation is occurring at for example 5712, which may also be marked as a condensation onset condition. The actual condensation onset condition may be somewhere between the two marked conditions 5711 and 5712, and may be shown on the graph as 5713, which would be a horizontal line (as shown in FIG. 30A) if the condensation onset condition remained consistent (that is, in a steady-state). If the actual condensation onset condition varies over time, for example, as shown in FIG. 30B, the condensation calibration algorithm 5710 may detect the condensation onset condition varying over time and may continually update the condensation onset condition.

Accordingly, where a plurality of measured condensation onset conditions are available, these values may be for example filtered over time (e.g. by low-pass filtering), or averaged, to estimate the actual condensation onset condition. Furthermore, the plurality of measured condensation onset conditions may be used to indicate a plausibility of measurements. For instance, the condensation calibration algorithm 5710 may be configured to indicate a potential fault (e.g. in the humidifier 5000 or air circuit 4170) where the measured condensation onset condition varies greatly (e.g. where a standard deviation of the measured condensation onset conditions is above a threshold).

5.5.3.4.3 Condensation Confirmation Algorithms 5720

The humidifier 5000 may also comprise algorithms configured to confirm an occurrence of condensation as determined by a condensation detection algorithm 5700. In one form, a condensation confirmation algorithm 5720 may be triggered when a condensation detection algorithm 5700 indicates an occurrence of condensation.

According to one aspect, a condensation confirmation algorithm 5720 may cause the humidifier 5000 to traverse the condensation onset condition, and compare a thermal response at either side of the condensation onset condition. For example, the condensation confirmation algorithm 5720 may decrease a heat output of the heating element 4171 from 20 W to 10 W, if 15 W was determined to be the condensation onset condition (e.g. traverse from a condensation condition 5716 to non-condensation condition 5714 in FIG. 29). Conversely, the heat output of the heating element 4171 may be increased from 10 W to 20 W where condensation was expected to occur at or below 15 W output, at which point it would be expected that no further condensation would occur.

In some cases, if an occurrence of condensation was due to a one-time event (e.g. introduction of moisture due to spillage by a user), or a change in an ambient condition (e.g. a blanket covering the tube being removed), traversing the condensation onset condition may not cause a cessation (or production) of condensates. In such cases, the condensation confirmation algorithm 5720 may be configured to continue to increase (or decrease) the heat output of the heating element 4171 until the expected change in thermal response (e.g. change from a condensation condition to a non-condensation condition, or vice versa) occurs.

5.5.3.5 Heating Plausibility Algorithms 5730

According to another aspect, the humidifier 5000 may comprise one or more heating plausibility algorithms 5730 to indicate an occurrence of a potential fault. For example, where a change in a variable has occurred, such as in an ambient temperature, output of a heating element (e.g. humidifier heating element 5220 or air circuit heating element 4171) or an air flow rate, a heating plausibility algorithm 5730 may assess whether the measured effects may be varying in a manner which may be consistent with the change in the variable.

For instance, if the flow sensor 4274 is recording a low flow rate condition, and one or more heating elements are heating the air flow, a heating plausibility algorithm 5730 may perform a check to assess whether a measured temperature is expected to increase, and whether the measured temperature is increasing in a manner consistent with the prediction. If the increase in temperature is lower than the predicted increase, or the temperature does not increase at all, the heating plausibility algorithm 5730 may indicate a fault condition.

In some forms, the heating plausibility algorithm 5730 may perform a mitigation step such as for example reducing or ceasing power supplied by a heating element 5220 or 4171.

5.5.3.6 Tube Detection Algorithms 5740

In one form, one or more measurements of a thermal response to a heat input may be used to detect a parameter of an air circuit 4170, such as its length. For example, where a known amount of electrical power is supplied, the thermal response of the heated tube may differ according to a parameter such as length, or amount of insulation, which may be used to determine the parameter.

5.6 Glossary

For the purposes of the present technology disclosure, in certain forms of the present technology, one or more of the following definitions may apply. In other forms of the present technology, alternative definitions may apply.

5.6.1 General

Air: 'Air' in the present disclosure will be taken to include breathable gases. In certain forms of the present technology, air supplied to a patient may be atmospheric air, and in other forms of the present technology atmospheric air may be supplemented with oxygen.

Ambient: In certain forms of the present technology, the term ambient will be taken to mean (i) external of the treatment system or patient, and (ii) immediately surrounding the treatment system or patient. For example, ambient humidity with respect to a humidifier may be the humidity of air immediately surrounding the humidifier.

Continuous Positive Airway Pressure (CPAP): CPAP treatment will be taken to mean the application of a supply of air or air to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Aspects of RPT Devices

Air circuit: A conduit or tube constructed and arranged in use to deliver a supply of air between an RPT device and a patient interface. In particular, the air circuit may be in fluid connection with the outlet of the pneumatic block and the patient interface. The air circuit may be referred to as air delivery tube. In some cases there may be separate limbs of the circuit for inhalation and exhalation. In other cases a single limb is used.

5.7 Other Remarks

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in a manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.8 REFERENCE SIGNS LIST

| | |
|---|---|
| patient | 1000 |
| bed partner | 1100 |
| patient interface | 3000 |
| seal-forming structure | 3100 |
| plenum chamber | 3200 |
| stabilising structure | 3300 |
| connection port | 3600 |
| forehead support | 3700 |
| RPT device | 4000 |
| external housing | 4010 |
| upper portion | 4012 |
| lower portion | 4014 |
| panel | 4015 |
| chassis | 4016 |
| handle | 4018 |
| pneumatic block | 4020 |

| | |
|---|---|
| pneumatic component | 4100 |
| air filter | 4110 |
| inlet air filter | 4112 |
| outlet air filter | 4114 |
| muffler | 4120 |
| inlet muffler | 4122 |
| outlet muffler | 4124 |
| pressure device | 4140 |
| blower | 4142 |
| motor | 4144 |
| back valve | 4160 |
| air circuit | 4170 |
| first air circuit zone | 4170_1 |
| second air circuit zone | 4170_2 |
| air circuit heating element | 4171 |
| first air circuit heating element | 4171_1 |
| second air circuit heating element | 4171_2 |
| supplemental oxygen | 4180 |
| electrical component | 4200 |
| PCBA | 4202 |
| power supply | 4210 |
| input device | 4220 |
| central controller | 4230 |
| clock | 4232 |
| therapy device controller | 4240 |
| protection circuit | 4250 |
| memory | 4260 |
| transducer | 4270 |
| pressure transducer | 4272 |
| flow transducer | 4274 |
| motor speed sensor | 4276 |
| data communication interface | 4280 |
| remote external communication network | 4282 |
| local external communication network | 4284 |
| remote external device | 4286 |
| local external device | 4288 |
| output device | 4290 |
| display driver | 4292 |
| display | 4294 |
| humidifier | 5000 |
| air inlet | 5002 |
| air outlet | 5004 |
| reservoir | 5110 |
| water volume detector | 5112 |
| water delivery mechanism | 5150 |
| water pump | 5152 |
| water delivery conduit | 5154 |
| mechanism | 5156 |
| water check valve | 5158 |
| humidification chamber | 5200 |
| outer housing | 5202 |
| outer housing inlet portion | 5202a |
| outer housing heater cover portion | 5202b |
| outer housing outlet portion | 5202c |
| inner housing | 5204 |
| water feed inlet | 5206 |
| air flow baffle | 5208 |
| water filter | 5214 |
| heating element | 5220 |
| reservoir heating element | 5221 |
| humidifier wick | 5230 |
| wick dry region | 5230_D |
| wick wet region | 5230_W |
| water boundary | 5230_WB |
| wick first layer | 5230a |
| wick second layer | 5230b |
| wick frame | 5232 |
| wick frame grip | 5232_G |
| wick locator | 5233 |
| humidifier filter | 5240 |
| flow sensor | 5512 |
| temperature sensor | 5514 |
| temperature sensor | 5514_1 |
| temperature sensor | 5514_2 |
| temperature sensor | 5514_3 |
| temperature sensor | 5514_4 |
| temperature sensor | 5514_5 |
| heating element temperature sensor | 5514_HE |
| pre-delivery chamber | 5515 |
| humidity sensor | 5516 |
| first humidity sensor | 5516_1 |
| second humidity sensor | 5516_2 |
| humidifier controller | 5550 |
| humidifier algorithm | 5600 |
| wick condition determination algorithm | 5610 |
| plausibility check algorithm | 5620 |
| pump condition determination algorithm | 5630 |
| humidification algorithm | 5650 |
| humidifier calibration algorithm | 5660 |
| humidifier start-up algorithm | 5665 |
| foreign matter management algorithm | 5670 |
| wick drying algorithm | 5675 |
| wick cleaning algorithm | 5680 |
| patient feedback algorithm | 5690 |
| condensation detection algorithm | 5700 |
| condensation calibration algorithm | 5710 |
| inflection point | 5712 |
| non - condensation condition | 5714 |
| condensation condition | 5716 |
| condensation confirmation algorithm | 5720 |
| heating plausibility algorithm | 5730 |
| tube detection algorithm | 5740 |
| downstream unheated region | 5230D |
| heated region | 5230H |
| upstream unheated region | 5230U |
| example wick condition determination algorithm | 5610A |
| example wick condition determination algorithm step 1 | 5610A1 |
| example wick condition determination algorithm step 2 | 5610A2 |
| example wick condition determination algorithm step 3 | 5610A3 |
| example wick condition determination algorithm step 4 | 5610A4 |
| example wick condition determination algorithm step 5 | 5610A5 |
| example wick condition determination algorithm step 6 | 5610A6 |
| example wick condition determination algorithm | 5610B |
| example wick condition determination algorithm step 1 | 5610B1 |
| example wick condition determination algorithm step 2 | 5610B2 |
| example wick condition determination algorithm step 3 | 5160B3 |
| example wick condition determination algorithm step 4 | 5160B4 |
| example wick condition determination algorithm step 5 | 5610B5 |
| example wick condition determination algorithm step 6 | 5610B6 |
| example wick condition determination algorithm step 7 | 5610B7 |
| example wick condition determination algorithm | 5610C |
| example wick condition determination algorithm step 1 | 5610C1 |
| example wick condition determination algorithm step 2 | 5610C2 |
| example wick condition determination algorithm step 3 | 5610C3 |
| example wick condition determination algorithm step 4 | 5610C4 |
| example wick condition determination algorithm step 5 | 5610C5 |
| example wick condition determination algorithm step 6 | 5610C6 |
| example wick condition determination algorithm step 7 | 5610C7 |
| example plausibility check algorithm | 5620A |
| example plausibility check algorithm step 1 | 5620A1 |
| example plausibility check algorithm step 2 | 5620A2 |
| example plausibility check algorithm step 3 | 5620A3 |
| example plausibility check algorithm step 4 | 5620A4 |
| example plausibility check algorithm step 5 | 5620A5 |
| example plausibility check algorithm step 6 | 5620A6 |

The invention claimed is:

1. A humidifier for increasing absolute humidity of a flow of air to be delivered to a patient's airways by a respiratory therapy device, the humidifier comprising:
   a humidifier housing forming a humidification chamber, the humidifier housing comprising:
      an air inlet configured to receive the flow of air from a pressure device;
      an air outlet configured to deliver the flow of air to a patient interface from the humidifier with added humidity; and
      a flow path for the flow of air from the air inlet, through the humidification chamber, and to the air outlet;
   a reservoir configured to retain a first volume of water;
   a humidifier wick positioned within the humidification chamber and configured to retain a second volume of water, and the humidifier wick having a profiled shape to substantially enclose, in a radial direction, at least a portion of the flow path;
   a delivery mechanism configured to deliver a flow of water from the reservoir to the humidifier wick;
   a heating element positioned in thermal communication with the humidifier wick to heat the humidifier wick to vaporise the second volume of water to add absolute humidity to the flow of air;
   an air flow baffle configured to lengthen at least a portion of the flow path through the humidification chamber; and
   a wick frame positioned within the portion of the flow path enclosed by the humidifier wick and in contact with the humidifier wick to maintain thermal communication between the humidifier wick and the heating element to promote heat transfer from the heating element to the humidifier wick;
   wherein the humidifier wick is removable from the humidification chamber, and
   wherein the humidifier wick is anisotropically constructed such that the humidifier wick has a rate of wicking that is greater in a first direction than in a second direction.

2. The humidifier as claimed in claim 1, wherein the second direction is a direction of the flow of air.

3. The humidifier as claimed in claim 1, wherein the flow path enclosed by the humidifier wick is substantially cylindrical.

4. The humidifier as claimed in claim 1, wherein the humidifier wick comprises one or more of: a corrugated, a dimpled, a perforated, a porous, a woven, a knitted, a textured, and a sintered surface.

5. The humidifier as claimed in claim 1, wherein the humidifier wick comprises one or more of: paper, hydrophilic fibres, and cellulose fibres.

6. The humidifier as claimed in claim 1, wherein the humidifier wick comprises a heated region and an unheated region.

7. The humidifier as claimed in claim 6, wherein the unheated region comprises an upstream unheated region located upstream of the heated region.

8. The humidifier as claimed in claim 6, wherein the unheated region comprises a downstream unheated region located downstream of the heated region.

9. The humidifier as claimed in claim 1, wherein the wick frame further comprises the air flow baffle.

10. The humidifier as claimed in claim 1, wherein the heating element comprises a resistive electrical track disposed on a circuit board.

11. The humidifier as claimed in claim 10, wherein the resistive electrical track comprises one or more strands of resistive wire forming a plurality of loops around a surface of the humidifier chamber.

12. The humidifier as claimed in claim 1, wherein the delivery mechanism is configured to deliver the flow of water to the humidifier wick through a plurality of fluid connections.

13. The humidifier as claimed in claim 1, further comprising one or more temperature sensors configured to measure one or more temperatures at the humidifier wick.

14. The humidifier as claimed in claim 13, wherein a plurality of temperature sensors are located along a direction of the flow of air.

15. The humidifier as claimed in claim 1, further comprising a sensor configured to indicate a saturation condition of the humidifier wick.

16. The humidifier as claimed in claim 15, wherein a temperature sensor is located at a periphery of the humidifier wick furthest from a water feed inlet to indicate the saturation condition.

17. The humidifier as claimed in claim 15, further comprising a controller configured to stop or slow delivery by the delivery mechanism upon indication of the saturation condition.

18. The humidifier as claimed in claim 1, wherein the wick frame comprises a wick locator configured to contact the humidifier wick and maintain the wick frame in position relative to the humidifier wick.

19. A system for providing a supply of air to the entrance to the airways at a pressure that is continuously positive with respect to atmosphere and constant through a respiratory cycle of a patient to treat Obstructive Sleep Apnea (OSA) with Continuous Positive Airway Pressure (CPAP), the system comprising:
   the humidifier as claimed claim 1; and
   a respiratory therapy device comprising a pressure device to generate the supply of air at the pressure in a range from about 4 cmH$_2$O to about 30 cmH$_2$O,
   wherein the pressure device is connected to the air inlet to direct the supply of air to the humidifier for humidification.

20. The system of claim 19, further comprising:
   a patient interface configured to form a seal with the patient's face around the entrance to the airways in use; and
   an air circuit in fluid communication with the air outlet to provide the supply of air from the humidifier to the patient interface.

* * * * *